United States Patent [19]
Stella et al.

[11] Patent Number: 6,046,177
[45] Date of Patent: *Apr. 4, 2000

[54] SULFOALKYL ETHER CYCLODEXTRIN BASED CONTROLLED RELEASE SOLID PHARMACEUTICAL FORMULATIONS

[75] Inventors: Valentino J. Stella; Roger A. Rajewski; Venkatramana M. Rao, all of Lawrence, Kans.; James W. McGinity, Austin, Tex.; Gerold L. Mosher, Kansas City, Mo.

[73] Assignee: Cydex, Inc., Overland Park, Kans.

[*] Notice: This patent is subject to a terminal disclaimer.

[21] Appl. No.: 09/229,513

[22] Filed: Jan. 13, 1999

Related U.S. Application Data

[63] Continuation-in-part of application No. 08/851,006, May 5, 1997, Pat. No. 5,874,418.

[51] Int. Cl.$^7$ .................. A61K 31/735; C07H 13/12; C08B 37/16

[52] U.S. Cl. .................. 514/58; 514/778; 514/964; 514/965; 536/103

[58] Field of Search .................. 514/58, 778, 964, 514/965; 536/103

[56] References Cited

U.S. PATENT DOCUMENTS

| | | |
|---|---|---|
| 3,426,011 | 2/1969 | Parmerter et al. . |
| 4,535,152 | 8/1985 | Szejtli et al. . |
| 4,727,064 | 2/1988 | Pitha . |
| 4,774,329 | 9/1988 | Friedman . |
| 4,869,904 | 9/1989 | Uekama et al. . |
| 4,946,686 | 8/1990 | McClelland et al. . |
| 5,134,127 | 7/1992 | Stella et al. . |
| 5,874,418 | 2/1999 | Stella et al. .............. 514/58 |

FOREIGN PATENT DOCUMENTS

| | | |
|---|---|---|
| 2197941 | 8/1997 | Canada . |
| 0251459 | 1/1988 | European Pat. Off. . |
| 195 13 659 A1 | 9/1996 | Germany . |
| 58-172311A2 | 10/1983 | Japan . |
| 59-084821A2 | 5/1984 | Japan . |
| 62-149628A2 | 7/1987 | Japan . |
| 64-40567A2 | 2/1989 | Japan . |
| 2 290 964 | 1/1996 | United Kingdom . |
| WO 94/06416 | 3/1994 | WIPO . |
| WO 94/14421 | 7/1994 | WIPO . |
| WO 95/01781 | 1/1995 | WIPO . |

OTHER PUBLICATIONS

Kaneto Uekama, Kazutaka Matsubara, Kentaro Abe, Yasuhide Horiuchi, Fumitoshi Hirayama, and Nobuo Suzuki, "Design and In Vitro Evaluation of Slow–Release Dosage Form of Pirentanide: Utility of β–Cyclodextrin: Cellulose Derivative Combination as a Modified–Release Drug Carrier," *Journal of Pharmaceutical Sciences*, vol. 79, No. 3, Mar. 1990, pp. 244–248.

O.I. Corrigan and C.T. Stanley, "Dissolution Properties of Phenobarbitone–β–Cyclodextrin Systems," *Pharm. Acta. Hel.*, vol. 56, No. 7 (1981), pp. 204–208.

A. Martini, C. Torricelli, L. Muggetti, R. DePonti, "Use of Dehydrated Beta–Cyclodextrin As Pharmaceutical Excipient," *Proceed. Intern.–Symp. Control. Rel. Bioact. Mater.*, 20 (1993), Controlled Release Society, Inc., pp. 304–305.

A. Gürsoy, M. Türkoglu, B. Senyücel, F. Kalkan, and I. Okar, "Evaluation of Tableted Microspheres of Dipyridamole," *Drug Development and Industrial Pharmacy*, 21(4) (1995), pp. 503–507.

H.O. Ammar, M. Ghorab, S. A. El–nahhas, S. M. Omar and M. M. Ghorab, "Improvement of some pharmaceutical properties of drugs by cyclodextrin complexation," *Pharmazie*, vol. 51 (1996), pp. 42–51.

Kristiina Järvinen, Tomi Järvinen, Diane O. Thompson and Valentino J. Stella, "The effect of a modified β–cyclodextrin, SBE4–β–CD, on the aqueous stability and ocular absorption of pilocarpine," *Current Eye Research* (1994).

V. J. Stella, H. K. Lee, D. O. Thompson, "The effect of SBE4–β–CD on i.m. prednisolone pharmacokinetics and tissue damage in rabbits: Comparison to a co–solvent solution and a water–soluble prodrug," *International Journal of Pharmaceutics*, vol. 120 (1995), pp. 197–204.

V. J. Stella, H. K. Lee, D. O. Thompson, "The effect of SBE4–β–CD on i.v. methylprednisolone pharmacokinetics in rats: Comparison to a co–solvent solution and two water–soluble prodrugs," *International Journal of Pharmaceutics*, vol. 120 (1995), pp. 189–195.

C. X. Song, V. Labhasetwar, R. J. Levy, "Controlled release of U–97983 from double–layer biodegradable matrices: effect of additives on release mechanism and kinetics," *Journal of Controlled Release*, vol. 45 (1997), pp. 177–192.

Valentino J. Stella and Roger A. Rajewski, "Cyclodextrins: Their Future in Drug Formulation and Delivery," *Pharmaceutical Research*, vol. 14, No. 5 (1997), pp. 556–567.

K. Uekama, F. Hirayama, and T. Irie, "New Functions of Peracylated β–Cyclodextrins as Sustained–Release Drug Carriers," Proceedings of the Eighth International Symposium on Cyclodextrins (1996), pp. 413–418.

(List continued on next page.)

*Primary Examiner*—Gary L. Kunz
*Attorney, Agent, or Firm*—Rick Matos; Akin, Gump, Strauss, Hauer & Feld, L.L.P.

[57] ABSTRACT

Sulfoalkyl ether cyclodextrin (SAE-CD) based controlled release pharmaceutical formulations are provided by the present invention. The present solid pharmaceutical formulations consist of a core comprising a physical mixture of one or more SAE-CD derivatives, an optional release rate modifier, a therapeutic agent, a major portion of which is not complexed to the SAE-CD, and an optional release rate modifying coating surrounding the core. The present formulations are advantageously easier to prepare than other SAE-CD based formulations in the art yet provide similar or improved effectiveness. The SAE-CD derivative is used to modify the bioavailability and/or rate of bioabsorption of therapeutic agents. Multi-layered, osmotic pump, coated, and uncoated tablet, minitablet, pellet, micropellet, particle, powder, and granule dosage forms are disclosed herein.

95 Claims, 29 Drawing Sheets

OTHER PUBLICATIONS

Tomi Järvinen, Kristiina Järvinen, Nancy Schwarting, and Valentino J. Stella, "β–Cyclodextrin Derivatives, SBE4–β–CD and HP–β–CD, Increase the Oral Bioavailability of Cinnarizine in Beagle Dogs," *Journal of Pharmaceutical Sciences*, vol. 84, No. 3, Mar. 1995, pp. 295–299.

Kazuto Okimoto, Masatoshi Miyake, Norlo Ohnishi, Roger A. Rajewski, Valentino J. Stella, Tetsumi Irie, and Kaneto Uekama, Design and Evaluation of an Osmotic Pump tablet (OPT) for Prednisolone, a Poorly Water Soluble Drug, Using $(SBE)_{7m}$–β–CD, *Pharmaceutical Research*, vol. 15, No. 1 (1998), pp. 1562–1568.

P. Mura, G. P. Bettinetti, A. Liguori, G. Bramanti, "Improvement of Clonazepam Release from a Carbopol Hydrogel," *Pharm. Acta Helv*, vol. 67, No. 9–10 (1992), pp. 282–288.

M. Chino, T. Kasama, Y. Noguchi, A. Ueda, and Y. Koyama, "Sustained–Release of Drugs from Cyclodextrin–Containing Hydrogels," Proceed. Intern. Symp. Control. Rel. Bioact. Mater., vol. 19 (1992), pp. 98–99.

Paolo Gionchedi, Lauretta Maggi, Aldo La Manna and Ubaldo Conte, "Modification of the Dissolution Behaviour of a Water–insoluble Drug, Naftazone, for Zero–order Release Matrix Preparation," *J. Pharm. Pharmacol.* vol. 46 (1994), pp. 476–480.

Kazuto Okimoto, Roger A. Rajewski, Kaneto Uekama, Janan A. Jona, and Valentino J. Stella, "The Interaction of Charged and Uncharged Drugs with Neutral (HP–β–CD) and Anionically Charged (SBE7–β–CD) β–Cyclodextrins," *Pharmaceutical Research*, vol. 13, No. 2 (1996), pp. 256–264.

Fumitoshi Hirayama, "Inclusion Ability of Hydrophobic Cyclodextrin Derivatives and Their Application as Controlled–Release Drug Carrier," *Yakugaku Kenkyu No Shinpo* (1990), (6), 90–98.

J. J. Torres–Labanderia, J. Blanco–Méndez and J. L. Vila–Jato, "Biopharmaceutical stability of the glibornuride/β–cyclodextrin inclusion complex after one year of storage," *S.T.P. Pharma. Sciences* 4(3), 1994, pp. 235–239.

F.J. Otero–Espinar, S. Anguiano–Igea, N. García–González, J.L. Vila–Jato and J. Blanco–Méndez, "Oral bioavailability of naproxen–β–cyclodextrin inclusion compound," *International Journal of Pharmaceutics*, 75 (1991), pp. 37–44.

Hideaki Yajima, Jun Sumaoka, Sachiko Miyama, and Makoto Komiyama, "Lanthanide Ions for the First Non–Enzymatic Formation of Adenosine 3''5''Cyclic Monophosphate from Adenosine Triphosphate under Physiological Conditions,", *Biochem*, 115 (1994), pp. 1038–1039.

M. T. Esclusa–Díaz, M. Gayo–Otero, M. B. Pérez–Marcos, J. L. Vila–Jato, J. J. Torres–Labandeira, "Preparation and evaluation of ketoconazole–β–cyclodextrin multicomponent complexes," *International Journal of Pharmaceutics*, 142 (1991), pp. 183–187.

Noriyuki Muranushi, Mariko Yoshida, Haruki Kinoshita, Fumiaki Hirose, Takayo Fukuda, Masami Doteuchi and Hideo Yamada, "Studies on benexata–CD: Effect of inclusion compound formation on the antiulcer activity of benexate, the effective ingredient of benexate–CD," *Folia pharmacol. Japon.* 91 (1988), pp. 377–383.

D. Peri, C. M. Wyandt, R. W. Cleary, A. H. Hikal and A. B. Jones, "Inclusion Complexes of Tolnaftate with –β–Cyclodextrin and Hydroxypropyl–β–Cyclodextrin," *Drug Development and Industrial Pharmacy*, 20(8) (1994), pp. 1401–1410.

PHYSICAL MIXTURE TABLETS

FREEZE-DRIED MIXTURE TABLETS

PHYSICAL MIXTURE TABLETS

FREEZE-DRIED MIXTURE TABLETS

SULFOALKYL ETHER CYCLODEXTRIN BASED CONTROLLED RELEASE SOLID PHARMACEUTICAL FORMULATIONS

CROSS-REFERENCE TO EARLIER FILED APPLICATIONS

This application is a continuation-in-part of U.S. application Ser. No. 08/851,006 filed May 5, 1997 which is now U.S. Pat. No. 5,874,418 issued Feb. 23, 1999.

FIELD OF THE INVENTION

This invention relates to controlled release cyclodextrin-based solid pharmaceutical formulations. More specifically, it relates to controlled release sulfoalkyl ether cyclodextrin (SAE-CD) based formulations wherein a major portion of the therapeutic agent is not complexed with the SAE-CD.

BACKGROUND OF THE INVENTION

Cyclodextrin/drug complexes are typically formed prior to their use in pharmaceutical formulations. U.S. Pat. No. 5,134,127 (the '127 Patent) to Stella et al. relates to sulfoalkyl ether cyclodextrin (SAE-CD) derivatives. The SAE-CD derivatives are proposed to be used as solubilizing agents for poorly water soluble or water insoluble drugs in various pharmaceutical dosage forms. The '127 Patent relates to compositions and formulations containing a drug complexed to a SAE-CD derivative to form clathrate/drug complexes or inclusion complexes thereof. Pharmaceutical formulations contemplated therein relate to those that include the clathrate complex and a pharmaceutically acceptable carrier. All of the formulations disclosed in the '127 patent require the preformation of an Drug/SAE-CD complex prior to preparation of the formulation.

Cyclodextrin (CD)/drug clathrate complexes are generally prepared separately prior to placement in a desired pharmaceutical formulation. Processes to prepare such formulations include steps that require much process monitoring and control and as such may complicate the formulation process. Efforts have been made to formulate cyclodextrins with poorly water soluble drugs together as physical mixtures and as inclusion complexes. Muranushi et al. (*Nippon Yakurigaky Zasahi* (1988), 91(6), 377–383) compared the dissolution profiles for neat benexate, benexate/cyclodextrin physical mixture and benexate-cyclodextrin complex. They reported the significantly increased solubility of benexate when prepared in the complexed vs. physical mixture or neat forms.

Similar results were reported by J. J. Torres-Labandeira et al. (*STP Pharma. Sci.* (1994), 4(3), 235–239) wherein the bioavailability of glibomuride-β-cyclodextrin complex was found to be two to three fold better than that of the glibomuride/β-cyclodextrin physical mixture. D. Peri et al. (*Drug. Dev. Ind. Pharm.* (USA) (1994), 20(4) 1401–1410) also reported that the drug-β-cyclodextrin complex showed improved dissolution over the physical mixture or free drug for tolnaftate. When naproxen and β-cyclodextrin were tested, the respective inclusion complex was found to have a six to nine fold increased solubility at five minutes over that of the physical mixture. (Otero-Espinar et al., *Int. J. Pharm.* (Netherlands) (1991), 75(1), 37–44).

Further evidence that the drug-β-cyclodextrin inclusion complex generally possesses a significantly better, dissolution profile than the corresponding physical mixture was reported by Lin et al. (*Int. J. Pharm.* (Netherlands) (1989), 56(3), 249–259) when β-cyclodextrin complexes and physical mixtures of acetaminophen, indomethacin, piroxicam and warfarin were tested. Esclusa-Diaz et al. (*Int. J. Pharm.* (Netherlands) (1996), 142(2) 183–187) also reported that the ketoconazole-β-cyclodextrin complex had a significantly better solubility than the corresponding physical mixture.

U.S. Pat. No. 4,946,686 to McClelland et al. discloses but does not exemplify another application of drug/cyclodextrin physical mixtures. This composition was designed solely for controlled release of a drug wherein solubility modulating units were present as slow release particles dispersed throughout a mixture of drug excipients. All of the components were then surrounded by a microporous water insoluble wall.

Okimoto et al. (*Pharmaceutical Research*, (1998) 15(10), 1562–1568), disclose an osmotic pump tablet containing prednisolone which is a poorly water soluble drug and the SAE-CD $(SBE)_{7M}$-β-CD. The osmotic pump tablet is prepared by kneading prednisolone and the cyclodextrin in the presence of water resulting in complexation of a significant portion, if not a major portion, of the prednisolone. A core containing the drug and cyclodextrin is coated with a semipermeable membrane containing a pore former to provide the osmotic pump tablet. The reported results indicate that a sustained release profile is provided by the osmotic pump tablet so long as the semipermeable membrane is present. Okimoto et al. further disclose that the SAE-CD can be used as a solubilizing agent and as an osmotic agent.

Giunchedi et al. (*J. Pharm. Pharmacol.*, (1994), 46. 476–480), disclose the preparation of a zero order release formulation containing the water insoluble drug naftazone β-cyclodextrin and hypromellose. The method of preparing this formulation resulted in the formation of a significant amount of preformed drug/cyclodextrin complex which measurably altered the morphology and characteristics of both the drug and the cyclodextrin.

Chino et al. (*Proceed. Intern. Symp. Control Rel. Bioact. Mater.*, (1992) 19. 98–99) disclose the preparation of a sustained release formulation containing a drug, a cyclodextrin and a hydrogel wherein the cyclodextrin and hydrogel were either conjugated together or mixed together prior to formation of the final formulation. In each example, the drug 5-FU was complexed with the cyclodextrin moiety during preparation of the formulation.

Mura et al. (*Pharm. Acta Helv.*, (1992) 67(9–10), 282–288) disclose formulations incorporating methyl β-cyclodextrin in combination with clonazepam into a solid composition wherein the drug and cyclodextrin are either complexed or uncomplexed prior to being dispersed or dissolved in a gel matrix. Mura et al. report that the methyl-β-cyclodextrin improves the flux rate of clonazepam from these gels through a lipophilic membrane comprising cellulose nitrate impregnated with lauryl alcohol.

Uekama et al. (*J. Pharm. Sci.*, (1990), 79(3n): 244–248) disclose a slow release dosage form of piretanide which is a bi-layered tablet having a first rapid releasing layer and a second slow releasing layer wherein the first rapidly releasing layer comprises β-cyclodextrin complexed with the piretanide.

Corrigan and Stanley (*Pharm. Acta Helv.* (1981) 56(7): 204–208) disclose controlled release formulations comprising phenobarbitone and β-cyclodextrin as eiter a preformed complex or physical mixture. Corrigan and Stanley report that the preformed complex performs substantially better than the physical mixture in terms of providing a reasonable controlled dissolution of the drug.

Martini (*Proceed. Intern. Symp. Control. Rel. Bioact. Mater.*, (1993), 20: 304–305 disclose the use of β-cyclodextrin to improve the bioavailability of drugs having a very low water solubility but a good absorption rate through biological membranes. The Martini formulation comprises a physical mixture of the β-cyclodextrin with the drug temazepam as either a physical mixture or preformed complex. In only one of several examples did Martini et al. obtain a physical mixture formulation having a dissolution profile comparable to that of the preformed complex formulation.

Elger et al. in European Patent Application Ser. No. 251,459 A discloses a controlled release pharmaceutical composition which comprises a drug, a water-soluble polydextrose or cyclodextrin, and a fatty alcohol or polyalkylene glycol wherein the drug and cyclodextrin can be present as a physical mixture or inclusion complex.

Thus, the art teaches that a drug-cyclodextrin preformed complex will generally have significantly better solubility, dissolution profile and bioavailability than its respective physical mixture. In the pharmaceutical industry, simplified processes are preferred over complex ones, and, with regard to cyclodextrin-containing and, specifically, SAE CD-containing compositions, a need continues to exist for simplified compositions and processes for their preparation. A need continues to exist in the pharmaceutical arts for a pharmaceutical formulation containing a drug/cyclodextrin physical mixture that possesses a dissolution profile, bioavailability and solubility similar to those characteristic of the respective drug-cyclodextrin complex.

SUMMARY OF THE INVENTION

As used herein the terms "a" or "an" are taken to mean one or more unless otherwise specified.

The present invention seeks to overcome the disadvantages inherent in known solid pharmaceutical formulations containing a therapeutic agent/cyclodextrin physical mixture. The invention regards simplified sulfoalkyl ether cyclodextrin-containing solid pharmaceutical compositions and formulations, and methods for their preparation for the sustained, delayed or controlled delivery of therapeutic agents. The pharmaceutical formulations herein are advantageously prepared by simplified processes not requiring the pre-formation of SAE-CD complexes with the therapeutic agents prior to preparation of the formulations. The formulations comprise an optional film coating surrounding a solid core which comprises a release rate modifier, a therapeutic agent/sulfoalkyl ether cyclodextrin physical mixture that when exposed to water or body fluids forms a therapeutic agent/sulfoalkyl ether cyclodextrin complex. The therapeutic agent/sulfoalkyl ether cyclodextrin physical mixture-containing pharmaceutical formulation will possess a solubility, dissolution profile and/or bioavailability which approximates that of the respective inclusion complex.

The present sustained release formulations can comprise an uncoated core containing a sustained release matrix, a core coated by a semipermeable membrane optionally containing a pore former, and/or an osmotic device formulation. In one embodiment, the release of SAE-CD from the formulation is independent of the ratio of therapeutic agent/cyclodextrin in the physical mixture. In another embodiment, the release of drug from the controlled release formulation of the invention is dependent upon the ratio of drug/cyclodextrin wherein the smaller the ratio, the faster the drug release and the larger the ratio, the slower the drug release from the formulation of the invention. In another embodiment, the release of drug is substantially independent of the particle size of the SAE-CD used in the formulation.

In another embodiment, the release rate modifier is present in an amount sufficient to make the release of drug from the formulation dependent upon the molecular weight or viscosity of the release rate modifier. In another embodiment, the release rate modifier is present in an amount sufficient to make the release of drug substantially independent of the molecular weight or viscosity of the release rate modifier. In another embodiment, increasing the drug:cyclodextrin ratio reduces the release rate of the drug and increases the release rate of the SAE-CD. In another embodiment, the release rate of drug is substantially equal to the release rate of cyclodextrin from the formulation when the drug/SAE-CD ratio is approximately equal to 1:1 to 3:1 or about 2.3:1. In another embodiment, increasing the ratio of release rate modifier to drug decreases the release rate of drug from the formulation. In another embodiment, increasing the ratio of release rate modifier to cyclodextrin decreases the release rate of cyclodextrin.

Accordingly, in one aspect, the present invention provides a solid pharmaceutical formulation comprising a film coating and a solid core, wherein the film coating comprises a film forming agent and a pore forming agent, and the solid core comprises a pharmaceutically acceptable carrier and a physical mixture of a therapeutically effective amount of a therapeutic agent and a sulfoalkyl ether cyclodextrin (SAE-CD), wherein a major portion of the therapeutic agent is not complexed to the SAE-CD.

The formulations of the present invention are simple compositions made by a simplified process. The present invention also permits the preparation of a wide range of dosage forms having unique characteristics.

In one embodiment, the sulfoalkyl ether cyclodextrin is a compound of the formula (I):

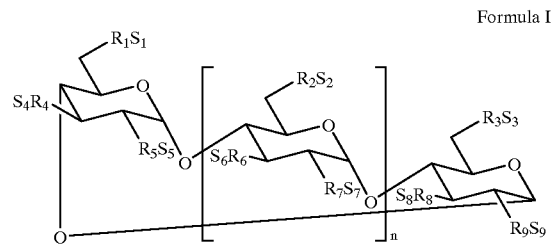

Formula I wherein:

n is 4, 5 or 6;

$R_1$, $R_2$, $R_3$, $R_4$, $R_5$, $R_6$, $R_7$, $R_8$ and $R_9$ are each, independently, —O— or a —O—(C2–C6)—$SO_3$- group, wherein at least one of $R_1$ and $R_2$ is independently a —O—(C2–C6 alkylene)—$SO_3$-group, preferably a —O—$(CH_2)_m SO_3$- group, wherein m is 4, (e.g. —$OCH_2CH_2CH_2SO_3$— or —$OCH_2CH_2CH_2SO_3$—); and $S_1$, $S_2$, $S_3$, $S_4$, $S_5$, $S_6$, $S_7$, $S_8$ and $S_9$ are each, independently, a pharmaceutically acceptable cation which includes, for example, $H^+$, alkali metals (e.g. $Li^+$, $Na^+$, $K^+$), alkaline earth metals (e.g., $Ca^{+2}$, $Mg^{+2}$), ammonium ions and amine cations such as the cations of (C1–C6)-alkylamines, piperidine, pyrazine, (C1–C6)-alkanolamine and (C4–C8)cycloalkanolamine.

The film coating serves to control the release of the therapeutic agent and the SAE-CD from the solid core. The film forming agent is the major component of the film coating and generally serves to slow the release of therapeutic agent and/or SAE-CD. A wide variety of film forming agents are contemplated. The pore forming agent serves to increase the permeability of the film coating by either forming pores or providing regions of enhanced water permeability in the film formed by the film forming agent.

In another aspect, the present invention is a simplified process for the preparation of sulfoalkyl ether cyclodextrin derivative-containing solid pharmaceutical formulations. Thus, the invention provides a process for the preparation of a SAE-CD containing pharmaceutical solid dosage form comprising the steps of:

forming a solid core comprising a physical mixture of a sulfoalkyl ether cyclodextrin derivative of the formula (I), a pharmaceutical carrier and an effective amount of a therapeutic agent, a major portion of which is not complexed to the sulfoalkyl ether cyclodextrin derivative; and coating said solid core with a film coating comprising a film forming agent and a pore forming agent to provide a pharmaceutically acceptable solid dosage form.

The process of the present invention does not require that a therapeutic agent/sulfoalkyl ether cyclodextrin complex be preformed in a dosage form prior to administration of the dosage form. Thus, a major portion of the therapeutic agent will remain uncomplexed in the final dosage form. The presence of a pore forming agent in the coating permits this formulation to deliver a therapeutic agent by diffusion through the coating.

Yet another aspect of the invention is a method of modifying the bioavailability and/or rate of bioabsorption of therapeutic agents. Thus, in one embodiment, the present invention provides a method of modifying the bioavailability or rate of bioabsorption of a therapeutic agent comprising the steps of:

providing a sulfoalkyl ether cyclodextrin and a therapeutic agent, a major portion of which is not complexed with the sulfoalkyl ether cyclodextrin, and administering to a patient the therapeutic agent and sulfoalkyl ether cyclodextrin, said sulfoalkyl ether cyclodextrin modifying the bioavailability or rate of bioabsorption of said therapeutic agent.

The sulfoalkyl ether cyclodextrin and therapeutic agent are preferably but need not be in the same dosage forms. It is only necessary that the SAE-CD and therapeutic agent become complexed after administration to a patient. A suitable dosage form comprising both the SAE-CD and the therapeutic agent will permit hydration of the therapeutic agent-SAE-CD physical mixture while in the dosage form to ensure proper formation of the therapeutic agent:SAE-CD complex. A wide range of therapeutic agents, including water soluble, hydrophilic and poorly water soluble, hydrophobic therapeutic agents, are used in some embodiments of the present formulations.

Pharmaceutical formulations described by the invention may further include one or more additional adjuvants and/or active ingredients chosen from those known in the art including flavors, diluents, colors, binders, fillers, glidants, lubricants, anti-static agents, buffers, antioxidants, preservatives, surfactants, disintegrants, bioadhesives, penetration enhancers, protease inhibitor stabilizers and compaction vehicles.

Still another embodiment of the invention provides a controlled release solid pharmaceutical formulation which is capable of delivering a therapeutic agent at a controlled rate even in the absence of a released rate modifying coat surrounding the core. Accordingly, in one embodiment, the invention is a controlled release solid pharmaceutical formulation consisting essentially of a core comprising a physical mixture of:

a therapeutic agent;
at least one sulfoalkyl ether cyclodextrin;
at least one release rate modifier; and
at least one pharmaceutically acceptable excipient;
wherein,
a major portion of the therapeutic agent is not complexed with the sulfoalkyl ether cyclodextrin; and
the therapeutic agent is released from the core at a controlled rate in the absence of a release rate modifying coat surrounding the core.

In the present embodiment, at least one of the sulfoalkyl ether cyclodextrin and the release rate modifier is responsible for the release of the therapeutic agent at a controlled rate. This controlled release formulation can further comprise one or more coats which further modify the delivery of the therapeutic agent so as to make the formulation a delayed release, targeted release, timed release, sustained release, or a even more carefully controlled release system.

Another embodiment of the invention provides a controlled release pharmaceutical formulation comprising a release rate modifying coat that does not require a pore forming agent. Accordingly, another embodiment of the invention includes a controlled release solid pharmaceutical formulation comprising:

a core comprising a physical mixture of a therapeutic agent and at least one sulfoalkyl ether cyclodextrin, wherein a major portion of the therapeutic agent is not complexed with the sulfoalkyl ether; and a coating surrounding said core and consisting of one or more film forming agents;

wherein, said therapeutic agent is released from said core at a controlled rate in the absence of a pore forming agent in said coating.

In this particular embodiment of the invention, the core can further comprise a release rate modifier which is capable of modifying the rate at which the therapeutic agent is released from the core. When the coating is a semipermeable membrane with a passageway therethrough, the formulation of the invention is an osmotic pump device.

Still another embodiment of the invention provides a multi-layered controlled release pharmaceutical formulation which does not require the preformation of a therapeutic agent/cyclodextrin complex. Accordingly, in the present embodiment, the invention is a multi-layered controlled release solid pharmaceutical formulation comprising at least two layers selected from:

at least one first layer comprising a physical mixture of a therapeutic agent and a sulfoalkyl ether cyclodextrin; and at least one different second layer comprising a release rate modifier;

wherein,
said first and second layers are juxtaposed;
said therapeutic agent is released from said core at a controlled rate; and
a major portion of said therapeutic agent is not complexed with said sulfoalkyl ether cyclodextrin.

According to the present embodiment, the formulation can comprise two or more different layers and will preferably comprise a first layer containing at least the therapeutic agent and sulfoalkyl ether surrounded by two second layers containing at least a release rate modifier.

Another aspect of the invention provides a multi-layered combined rapid and controlled release solid pharmaceutical formulation comprising:

at least one controlled release first layer comprising a physical mixture of a first therapeutic agent, a release rate modifier and a sulfoalkyl ether cyclodextrin for releasing said first therapeutic agent at a controlled rate into a first environment of use; and at least one rapid release second layer comprising a preformed complex of a second therapeutic agent and a sulfoalkyl ether cyclodextrin for releasing said second therapeutic agent substantially immediately into a second environment of use;

wherein, said first and second layers are juxtaposed; and a major portion of said first therapeutic agent is not complexed with said sulfoalkyl ether cyclodextrin.

Still another aspect of the invention provides combination rapid and controlled release solid pharmaceutical formulation comprising a physical mixture of:

a first group of particles comprising a physical mixture of a first therapeutic agent, a release rate modifier and a sulfoalkyl ether cyclodextrin for releasing said first therapeutic agent at a controlled rate into a first environment of use; and a second group of particles comprising an inclusion complex of a second therapeutic agent and a sulfoalkyl ether cyclodextrin for releasing said second therapeutic agent rapidly into a second environment of use.

In yet another embodiment of the invention, the controlled release formulation is an osmotic pump that delivers drug in controlled manner by employing diffusion of the drug across a membrane and osmosis of the drug through a passageway in the membrane. The combined diffusional and osmotic controlled delivery of drug can be achieved with an osmotic pump comprising:

a core comprising a physical mixture of a sulfoalkyl ether cyclodextrin, a therapeutic agent and a pharmaceutically acceptable carrier; and a membrane surrounding said core and comprising a film forming agent and a pore forming agent, said membrane having a passageway therethrough for communicating said core to an environment of use;

wherein, a first portion of said therapeuic agent diffuses through said membrane and a second portion of said therapeutic agent passes through said passageway; and a major portion of said therapeutic agent is not complexed with said sulfoalkyl ether cyclodextrin.

The membrane of the osmotic pump has a predetermined composition and/or thickness that is varied to control the delivery of therapeutic agent. In one embodiment, the membrane has a thickness and is of a composition that enhances diffusion of the therapeutic agent through the membrane. In another embodiment, the membrane has a thickness and is of a composition that enhances osmosis of the therapeutic agent through a passageway in the membrane.

While each of the preceding pharmaceutical formulations according to the invention comprise a pharmaceutical composition containing a physical mixture of a therapeutic agent and a sulfoalkyl ether cyclodextrin wherein a major portion of the therapeutic agent is not complexed with the sulfoalkyl ether cyclodextrin, the present formulations can further comprise additional compositions containing a complex of the therapeutic agent and the sulfoalkyl ether cyclodextrin. Accordingly, each of the preceding formulations can comprise a first composition containing the drug and cyclodextrin in uncomplexed form and a second composition containing the drug and cyclodextrin in complexed form. It will be understood by the artisan of ordinary skill that the second composition containing the drug/cyclodextrin complex is either a rapid release or controlled release formulation but will preferably be used as a rapid release formulation to provide for immediate release of the therapeutic agent thereby rapidly raising the plasma level of the therapeutic agent in a patient being administered the formulation.

Upon review of the present disclosure the artisan of ordinary skill will understand that the ratio of sulfoalkyl ether cyclodextrin to drug is also used to control the delivery of the drug.

Other features, advantages and embodiments of the invention will be apparent to those of ordinary skill in the art from the following description, examples and appended claims.

BRIEF DESCRIPTION OF THE DRAWINGS

The following drawings form part of the present specification and are included to further illustrate certain aspects of the invention. The invention can be better understood by reference to one or more of the drawings in combination with the detailed description of the specific embodiments presented herein.

DETAILED DESCRIPTION OF THE INVENTION

Figure 1:
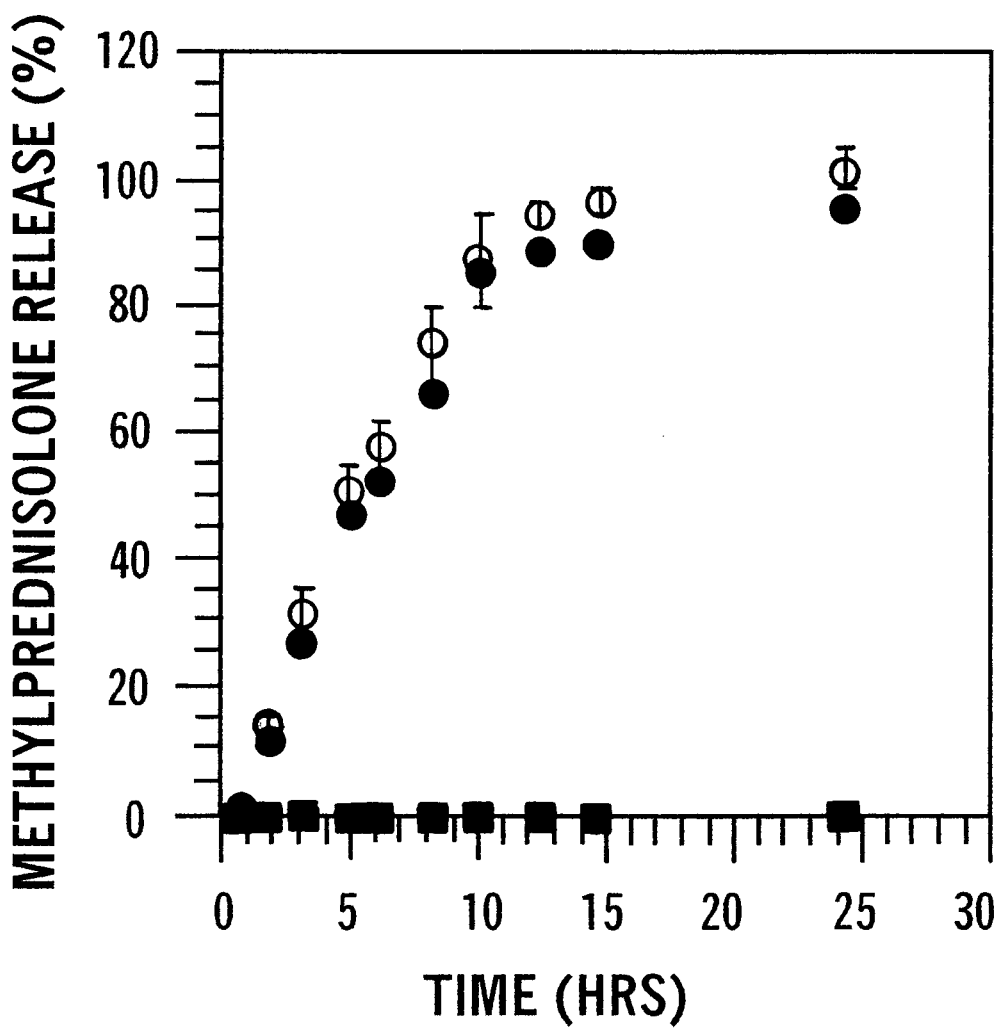
FIG. 1. Release profiles for methyprednisolone and $SBE_7\beta$-CD-containing formulations.
Figure 1:
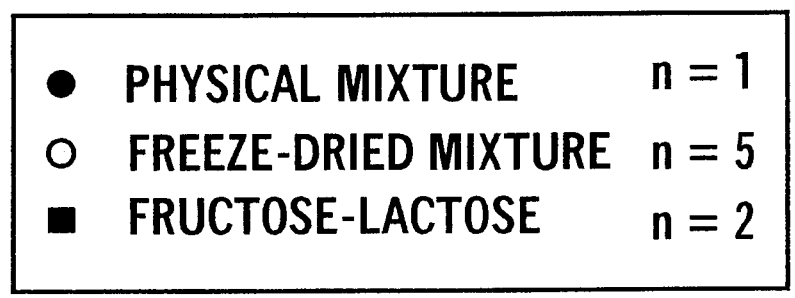

The present invention overcomes the disadvantages inherent in known therapeutic agent/cyclodextrin physical mixture-containing pharmaceutical formulations by providing a formulation that is easy to prepare and has a therapeutic agent solubility, dissolution profile and/or bioavailability that approximates that of its respective therapeutic agent/cyclodextrin complex-containing pharmaceutical formulation. The present invention employs sulfoalkyl ether cyclodextrin (SAE-CD) derivatives in preparing a wide range of pharmaceutical formulations as herein described. The present formulations are used for rapid, controlled, delayed, timed, pulsatile and sustained delivery of a wide range of therapeutic agents. The formulations can also be included in a wide variety of dosage forms as herein described.

Sulfoalkyl Ether Cyclodextrin Derivatives

The terms "alkylene" and "alkyl," as used herein (e.g., in the —O—(C2–C6-alkylene)$SO_3$-group or in the alkylamines), include linear, cyclic, and branched, saturated and unsaturated (i.e., containing one double bond) divalent alkylene groups and monovalent alkyl groups, respectively. The term "alkanol" in this text likewise includes both linear, cyclic and branched, saturated and unsaturated alkyl components of the alkanol groups, in which the hydroxyl groups may be situated at any position on the alkyl moiety. The term "cycloalkanol" includes unsubstituted or substituted (e.g., by methyl or ethyl) cyclic alcohols.

The present invention provides compositions containing a mixture of cyclodextrin derivatives, having the structure set out in formula (I), where the composition overall contains on the average at least 1 and up to 3 n+6 alkylsulfonic acid moieties per cyclodextrin molecule. The present invention also provides compositions containing a single type of cyclodextrin derivative, or at least 50% of a single type of cyclodextrin derivative.

The present cyclodextrin derivatives are either substituted at least at one of the primary hydroxyl group (i.e., at least one of $R_1$ to $R_3$ is a substituent), or they are substituted at both the primary hydroxyl group and at the 3-position hydroxyl group (i.e., both at least one of $R_1$ to $R_3$ and at least one of $R_4$, $R_6$ and $R_8$ are a substituent). Substitution at the 2-position hydroxyl group, while theoretically possible, on the basis of the inventors' studies, does not appear to be substantial in the products of the invention.

The cyclodextrin derivatives of the present invention are obtained as purified compositions, i.e., compositions containing at least 95 wt. % of cyclodextrin derivative(s) with the substitution occurring at least on the primary hydroxyl group of the cyclodextrin molecule (i.e. $R_1$, $R_2$ or $R_3$ of formula (I)). In a preferred embodiment, purified compositions containing at least 98 wt. % cyclodextrin derivative(s) are obtained.

In some of the compositions of the invention unreacted cyclodextrin has been substantially removed, with the remaining impurities (i.e., <5 wt. % of composition) being inconsequential to the performance of the cyclodextrin derivative-containing composition.

The cyclodextrin derivatives used herein are generally prepared as described in U.S. Pat. No. 5,134,127, the entire disclosure of which is incorporated herein by reference. This preparation process may comprise dissolving the cyclodextrin in aqueous base at an appropriate temperature, e.g., 70° to 80° C., at the highest concentration possible. For example, to prepare the cyclodextrin derivatives herein, an amount of an appropriate alkyl sultone, corresponding to the number of moles of primary CD hydroxyl group present, is added with vigorous stirring to ensure maximal contact of the heterogeneous phase.

The various SAE-CD derivatives evaluated include $SBE_4\beta$, $SBE_7\beta$, $SBE_{11}\beta$, and $SBE_4\gamma$ which correspond to SAE-CD derivatives of the formula I wherein n=5, 5, 5 and 6; m is 4; and there are 4, 7, 11 and 4 sulfoalkyl ether substituents present, respectively. It has been found that these SAE-CD derivatives increase the solubility of poorly water soluble drugs to varying degrees. For example, the table below summarizes the binding constant and solubility observed with several SAE-CDs (0.1 M at 25° C.) and methylprednisolone.

| SAE CD type | Binding Constant | Solubility (mg/mL) |
|---|---|---|
| $SBE_4\beta$ | 700 | 5.62 |
| $SBE_7\beta$ | 710 | 5.95 |
| $SBE_{11}\beta$ | 960 | 6.73 |
| $SBE_4\gamma$ | 2600 | 14.74 |

In another embodiment, the present invention employed dipyridamole (DP) which is a basic drug (pka=6.28) having poor aqueous solubility of its free base (3.6 μg/mL at 25° C.) and low and variable bioavailability. $SBE_7\beta$-CD was found to increase DP solubility dramatically. The table below summarizes the solubility of DP in the presence and absence of $SBE_7\beta$-CD at different pH values.

| pH | $SBE_7\beta$-CD Conc. (M) | DP Solubility (μg/ml) |
|---|---|---|
| 7.0 | 0 | 3.56 |
| 7.0 | 0.1 | 504 |
| 4.0 | 0 | 1990 |
| 4.0 | 0.1 | 16000 |

While the above embodiments exemplify some of the SAE-CD derivatives contemplated by the invention, they should not be considered as limiting the full scope of coverage to which the invention is entitled.

Sulfoalkyl Ether Cyclodextrin-Containing Pharmaceutical Formulation

In order to obtain a cyclodextrin pharmaceutical formulation having acceptable solubility, dissolution profile and bioavailability characteristics, it is generally accepted in the art that a clathrate or an inclusion complex of a cyclodextrin and a therapeutic agent must generally be preformed separately prior to preparation of a pharmaceutical formulation containing the same. However, the present inventors have found that separate preformation of the SAE-CD: therapeutic agent complex is unnecessary.

SAE-CD containing pharmaceutical formulation of the invention will comprise an SAE-CD derivative of the formula (I), as described above, a pharmaceutical carrier, a therapeutic agent and, optionally, additional adjuvants and active ingredients where a major portion of the therapeutic agent is not complexed with the SAE-CD derivative.

Since it is intended that only a major portion of the therapeutic agent included in the present formulation will not be complexed with the SAE-CD, it is possible that some therapeutic agent/SAE-CD complex will be present. The presence of SAE-CD: therapeutic agent complex in the present formulation may or may not be intentional, i.e., the complex can be prepared separately according to the Stella et al. patent and then included in the formulation or the complex may have been formed during the preparation of the present formulation.

By "therapeutic agent/SAE-CD complex" is generally meant a clathrate or inclusion complex of a sulfoalkyl ether cyclodextrin derivative of the formula (I) and a therapeutic agent. The ratio of therapeutic agent:SAE-CD present in the complex can vary and can be in the range of about 1:2 to about 2:1, on a molar basis, respectively, and preferably about 1:1. In another embodiment of the dosage forms described herein, the ratio of therapeutic agent: SAE-CD is in the range of about 2:1 to about 1:100 on a molar basis, preferably about 1:1 to about 1:20 and more preferably about 2:1 to about 1:10 on a molar basis. Thus, the SAE-CD will generally be, but need not be, present in excess of the therapeutic agent. The amount of excess will be determined by the intrinsic solubility of the agent, the expected dose of the agent, and the binding constant for inclusion complexation between the specific drug (agent) and the specific SAE-CD.

By "complexed" is meant "being part of a clathrate or inclusion complex with", i.e., a complexed therapeutic agent is part of a clathrate or inclusion complex with a sulfoalkyl ether cyclodextrin derivative. By "major portion" is meant at least about 50% by weight of the therapeutic compound. Thus, a formulation according to the present invention will contain a therapeutic agent of which more than about 50% by weight is not complexed with an SAE-CD. In various embodiments, preferably greater than 60% by weight, more preferably greater than 75% by weight, even more preferably greater than 90% by weight, and most preferably greater than 95% by weight of the therapeutic agent will remain uncomplexed with an SAE-CD while in the pharmaceutical formulation.

By "physical mixture" is meant a mixture of a drug and an SAE-CD that has been formed by physically mixing the drug and the SAE-CD together in such a manner as to minimize the formation of a drug/SAE-CD inclusion complex.

It is intended that the therapeutic agent will begin to complex with the SAE-CD upon administration of a dosage form containing the composition of the invention to a patient and exposure of the composition to body fluids. For example, when a capsule containing powders of therapeutic agent and SAE-CD is administered orally to a patient, the capsule will dissolve, thus permitting gastric juice to contact the therapeutic agent and SAE-CD, and a therapeutic agent/SAE-CD complex will form. A suitable dosage form will permit the physical mixture to become hydrated prior to release from the dosage form to ensure proper complex formation.

The ratio of therapeutic agent:SAE-CD present in the formulation will depend on a number of factors, such as, the intrinsic solubility of the agent, the expected dose of the agent, and the binding constant for inclusion complexation between the specific drug (agent) and the specific SAE-CD. These factors combined will determine the amount of SAE-CD needed in the dosage form and therefore the ratio of SAE-CD: therapeutic agent.

The molecular weight of most SAE-CDs is about 2,000, most therapeutic agents have molecular weights in the range of 200–500, and most drugs form 1:1 inclusion complexes with SAE-CDs. Because of these molecular weight differences, the amount of SAE-CD needed will generally be minimally about 1–10 times the amount of agent on a weight basis and can be even higher. This assumes that one mole of CD will solubilize one mole of drug and that the binding constant between the agent and the CD is infinitely high. For most solid dosage forms for human administration, it is best to have tablets that are less than one gram in total weight, and because of the need for other excipients within the tablet formulation, the tablet will preferably contain less than 500 mg of CD. Based on this simple assumption, therefore, the amount of drug formulated with the SAE-CD will generally be less than 50 mg. Since most drugs will not have an infinitely high binding constant with SAE-CDs, the total dose of drug that can generally be formulated with the SAE-CD is <50 mg.

More specifically, agents can form weak through very strong inclusion complexes with SAE-CDs. A very weak inclusion complex would be one where the binding constant is less than about 500 M$^{-1}$; a weak constant would be one where the binding constant is about 500 to about 1000 M$^{-1}$; a moderate binder would have a binding constant of about 1,000 to about 5,000 M$^{-1}$; a strong binder would be one with a binding constant of about 5,000 to about 20,000 M$^{-1}$; and a very strong binder would have a binding constant of greater than about 20,000 M$^{-1}$.

The relative increase in the solubility of a poorly soluble drug in the presence of SAE-CDs is a product of the binding constant and the molar concentration of SAE-CD present. For a very weakly bound drug, a ratio of 100:1, on a molar basis, between SAE-CD and agent might be necessary. If this is the case, the amount of drug in the formulation might have to be as low as 1 mg. If the binding constant between SAE-CD and the agent is very strong, then a ratio of about 1:1 could be permitted. In such a case, a drug dosage as high as 50 mg can be used provided the intrinsic solubility of the drug is suitable. Consider a drug with a binding constant of 10,000 M$^{-1}$, a binding constant that is realistic for a number of drugs. In the presence of 0.1 M SAE-CD, the solubility of the drug would be increased about 1,000 fold over the solubility in the absence of the SAE-CD. If the intrinsic solubility of the drug is about 1 ng/ml, then only a solubility of about 1 µg/ml will be possible in the presence of 0.1 M SAE-CD, however, if the intrinsic solubility of the drug is about 10 µg/ml, then a solubility of about 10 mg/ml might be possible in the presence of about 0.1 M SAE-CD.

Various therapeutic agent/SAE-CD physical mixture-containing pharmaceutical formulations are contemplated by the present invention: osmotic pump tablet, layered tablet, coated tablet, coated pellets, powder for reconstitution, capsules, coated granules and hot-melt extruded films.

The coated tablets, granules and pellets of the invention comprise an optional film coating and a solid core. The film coating comprises a film coating agent and an optional pore forming agent. The film coating can also comprise plural film forming agents and optionally pore forming agents, e.g. combinations of film forming agents are used in some embodiments of the film coating.

The terms "film forming agent" and "release controlling agent" are used interchangeably herein and are intended to include polymeric compounds (of natural, synthetic, semi-synthetic or genetically engineered sources) which will form a film coating around the solid core of the formulation and control the release or slow down the release rate of therapeutic agent or SAE-CD from said core. The film forming agents contemplated by the invention are further described and, for particular embodiments, exemplified herein.

Figure 2A:
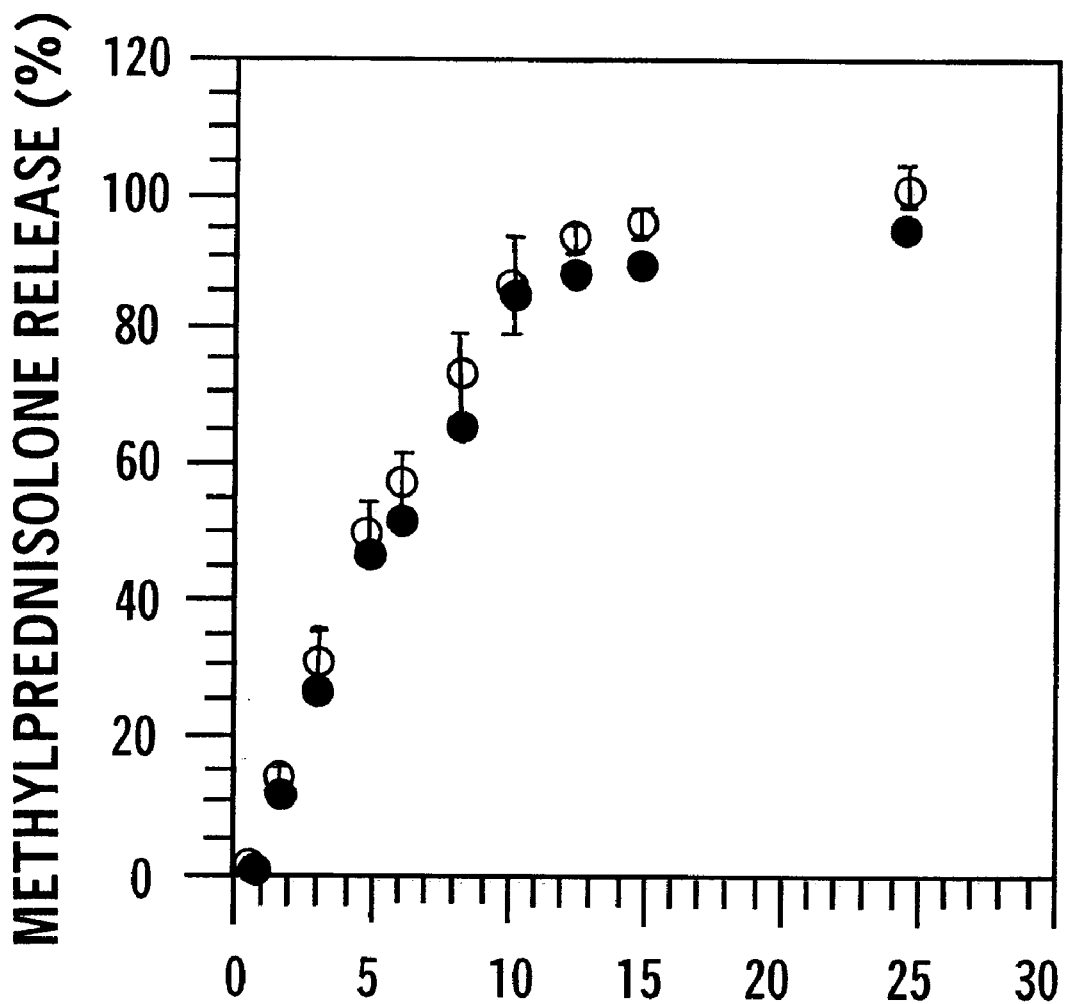
FIGS. 2a and 2b. Release profiles for methyprednisolone and $SBE_7\beta$-CD-containing physical mixture and freeze-dried complex formulations.
Figure 2B:
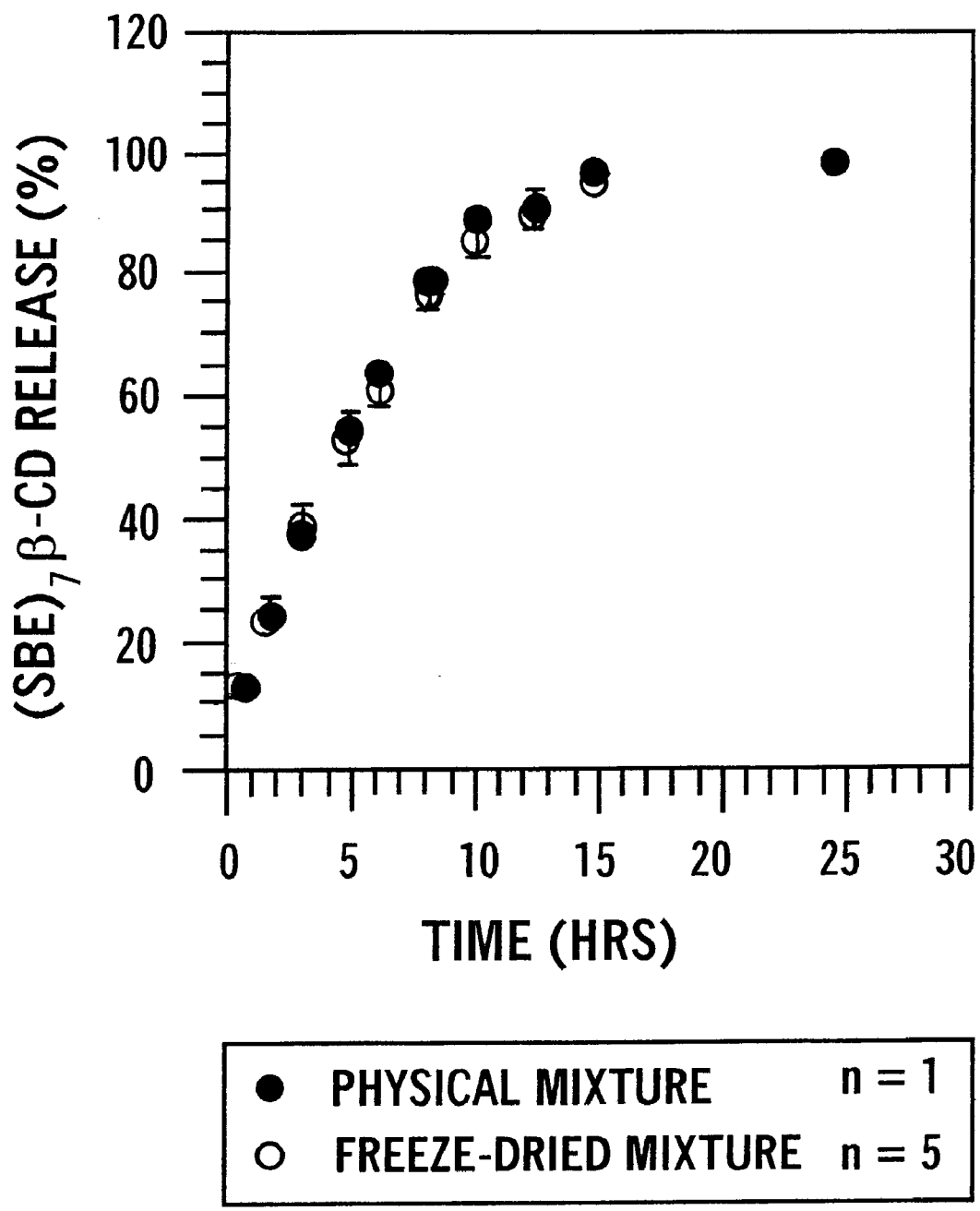

FIG. 1, which procedure is detailed in Example 1, depicts the release profiles for two methylprednisolone (MP) containing osmotic pump tablets which differ only in the complexation of the SAE-CD and the therapeutic agent. Two compositions, the first containing methylprednisolone/SBE$_7$β-CD physical mixture and the second containing methylprednisolone-SBE$_7$β-CD complex, were formulated into controlled release osmotic pump tablets according to Example 1. The MP and SBE$_7$β-CD (present in a 1:7 molar ratio) along with a pharmaceutical carrier were compressed into a solid core which was spray coated with a mixture of ethylcellulose, PEG3350, PEG400 and ethanol to form a 140 µm thick film coating around the solid core. The dissolution profile was determined using USP dissolution apparatus II (100 rpm, 37° C.) and an HPLC assay for methylprednisolone (MP). A fluorimetric assay employing 2,6-toluidino naphthalene sulfonate (2,6-TNS) was developed for quantitating the SAE-CD. The first formulation, indicated in FIG. 1 by the hollow circles, contains the separately preformed MP-SBE$_7$β CD freeze-dried complex. The second formulation, indicated by the filled in circles, contains a major portion of uncomplexed MP as a physical mixture with SBE$_7$β-CD. The third formulation, indicate by the squares, contains a physical mixture of lactose, fructose and MP. It is evident by the similarity of the curves corresponding to the preformed complex and the physical mixture, that the latter has a release profile similar to or substantially similar to the former. It should be noted that, for this particular dosage form, the MP and SBE$_7$β-CD had substantially the same release profiles. The results are depicted in FIGS. 2a and 2b for MP and SBE$_7$β-CD, respectively.

Figure 8:
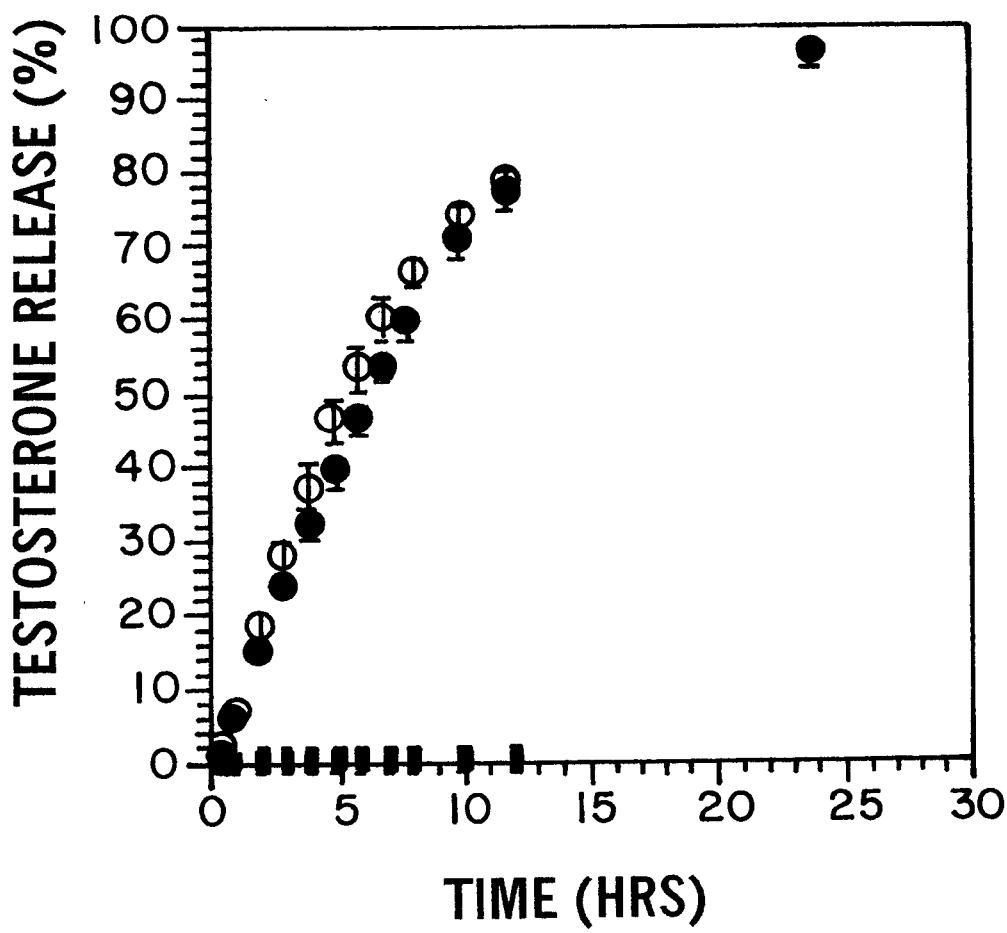
FIG. 8. Release profile for testosterone/$SBE_7\beta$-CD controlled release tablet formulations.

When the therapeutic agent was testosterone (TST), the physical mixture formulation of SBE$_7$β-CD and TST exhibited the same release profile as the respective freeze dried mixture. (FIG. 8) The solid core of the tablet comprised a 1:1 molar ratio of TST and SBE$_7$β-CD. The film coating of this tablet comprised sorbitol, PEG 400 and cellulose acetate. The release profiles of the physical mixture and complex formulation were compared to that of a baseline TST/fructose-lactose formulation.

Figure 3A:
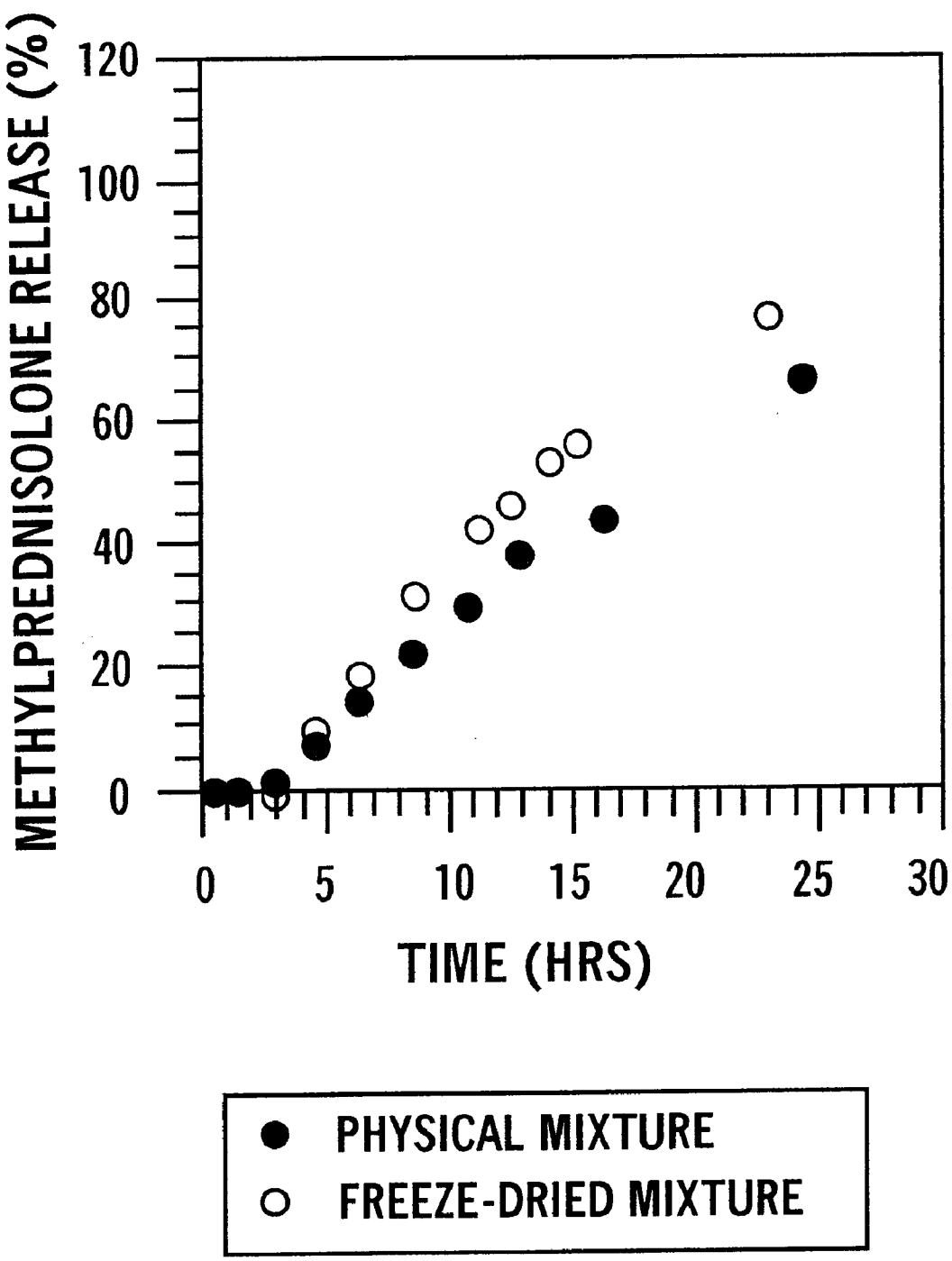
FIGS. 3a and 3b. Methyprednisolone (MP) and $SBE_7\beta$-CD release profiles from physical mixture and freeze-dried complex formulations having a 200µ film coating.
Figure 3B:
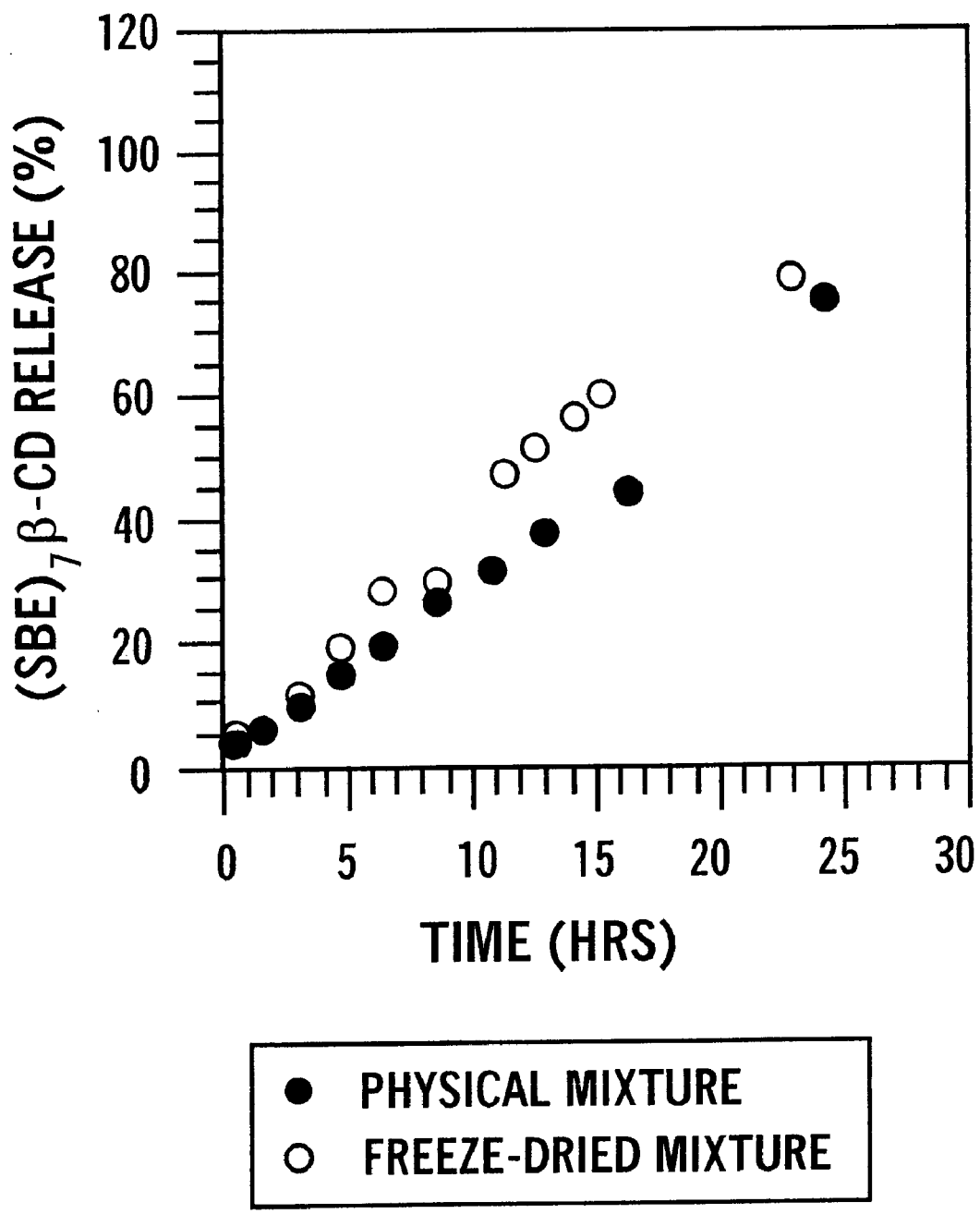
Figure 4A:
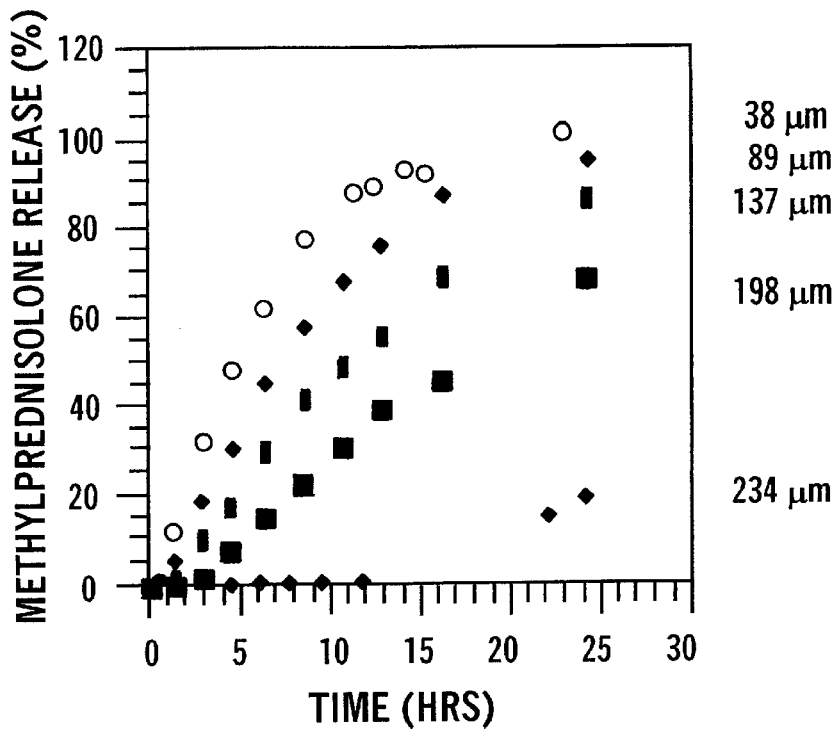
FIGS. 4a and 4b. Effect of film thickness upon MP and $SBE_7\beta$-CD release profiles in a film coated tablet formulation.
Figure 4B:
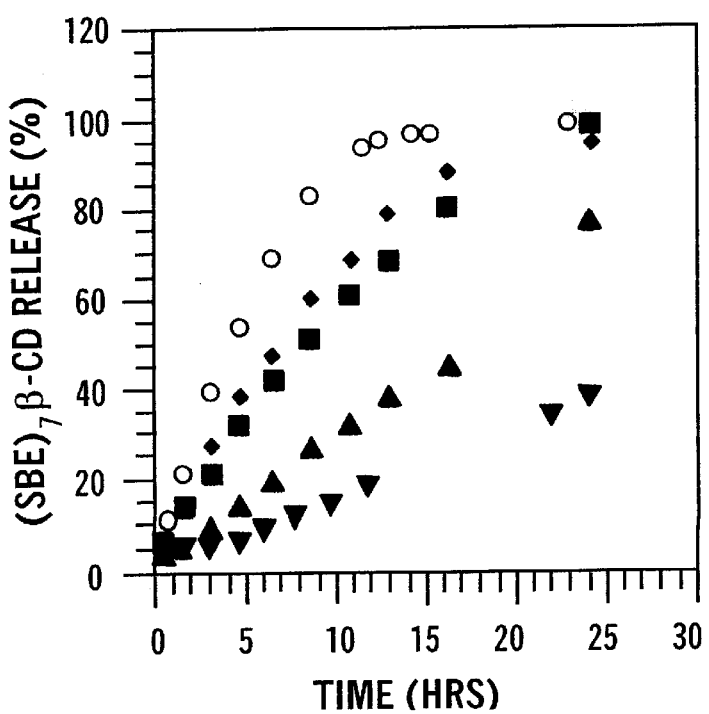
Figure 5:
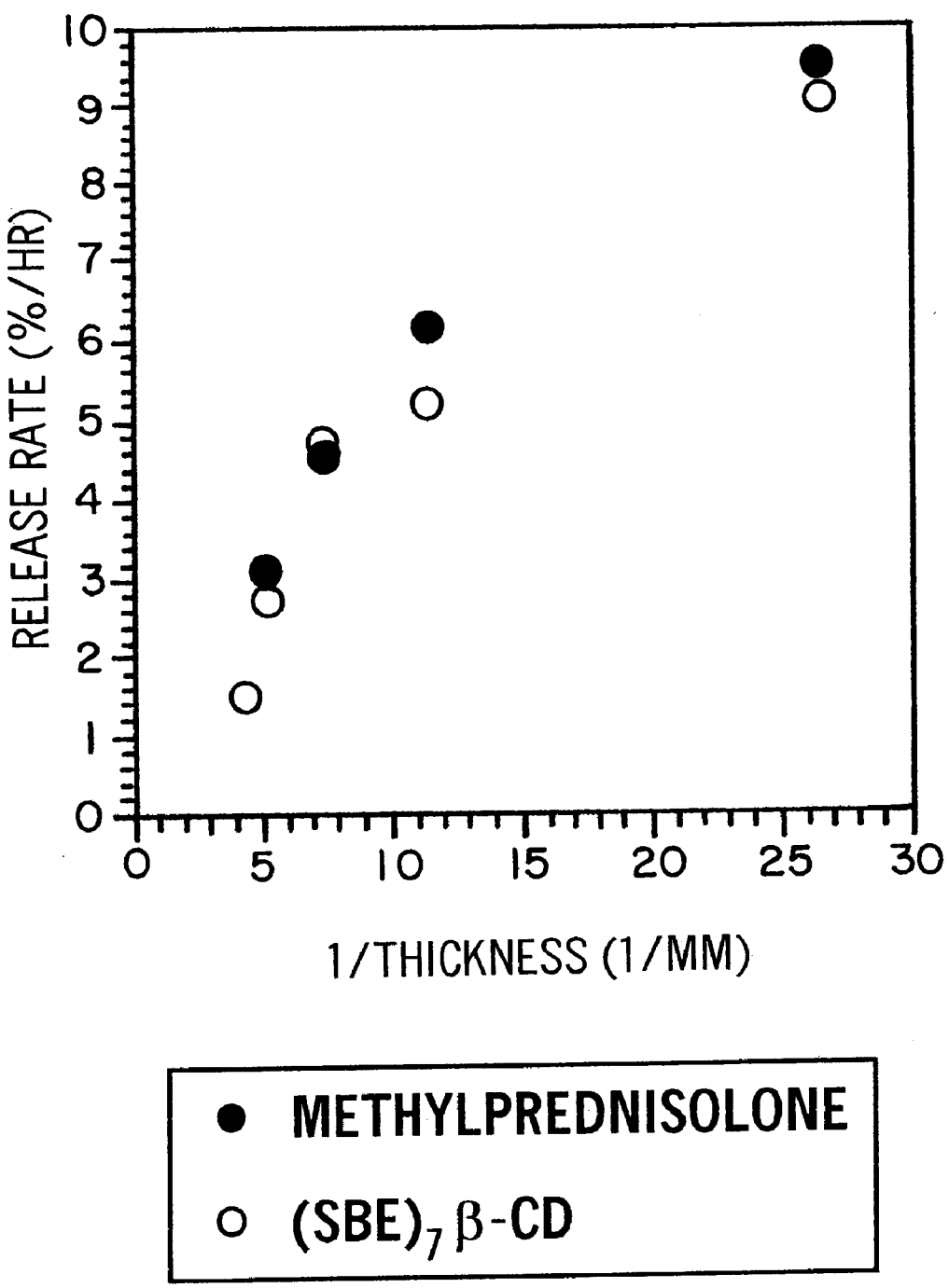
FIG. 5. Relationship between release rate and the inverse of film thickness for MP and $SBE_7\beta$-CD from a physical mixture tablet formulation.

When the thickness of the film coating, or membrane, surrounding the tablet core, which comprised either a physical mixture or a freeze dried complex of MP and SBE$_7$β-CD, was increased to 200 µm, a slight difference was noted in the release profiles of the physical mixture versus the freeze dried complex; however, the SBE$_7$β-CD did have a release profile substantially similar to that of the MP. The results are depicted in FIGS. 3a and 3b for MP and SBE$_7$β-CD, respectively. Additional exemplary film coated tablets having film thicknesses of 38, 89, 137, 198 and 234 µm were prepared and evaluated as above. The results depicted in FIGS. 4a and 4b indicated that SBE$_7$β-CD exhibited substantially the same release profile as MP in each of the dosage forms. In the 234 µm film embodiment, the freeze-dried complex appeared to release SBE$_7$β-CD faster than MP; however, when the release rate data for the physical mixture embodiments of FIGS. 4a and 4b was plotted against the inverse of the film thickness, the results indicated that the SBE$_7$β-CD had a release profile substantially similar to the MP (FIG. 5).

Figure 10:
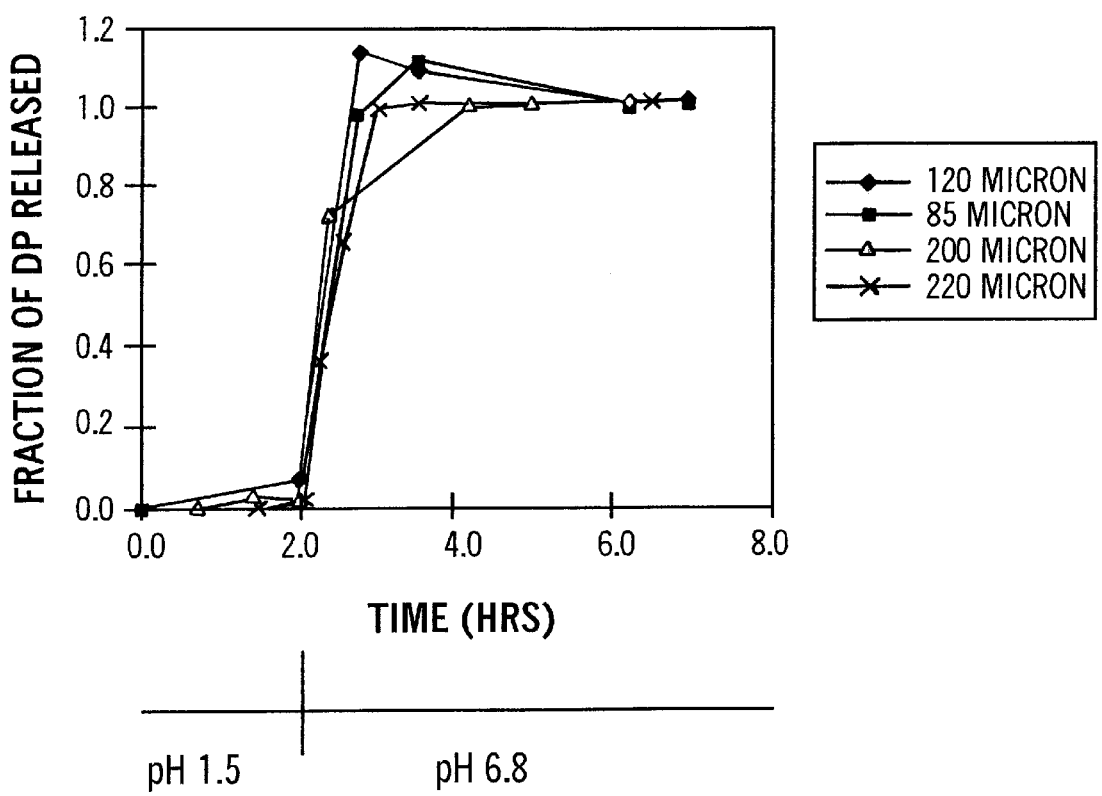
FIG. 10. Effect of film thickness on DP release through EUDRAGIT™-L and urea membrane from a tablet core comprising DP and $SBE_7\beta$-CD physical mixture.

Film thickness need not have a significant impact upon the release profile of a given dosage form. FIG. 10 depicts the effect that film thickness has upon a delayed release formulation comprising an EUDRAGIT™-L/urea film coating and a dipyridamole/SBE$_7$β-CD physical mixture solid core. The results indicate that, for this embodiment, the release profile for DP is independent of film thickness but dependent upon solution pH.

Figure 11:
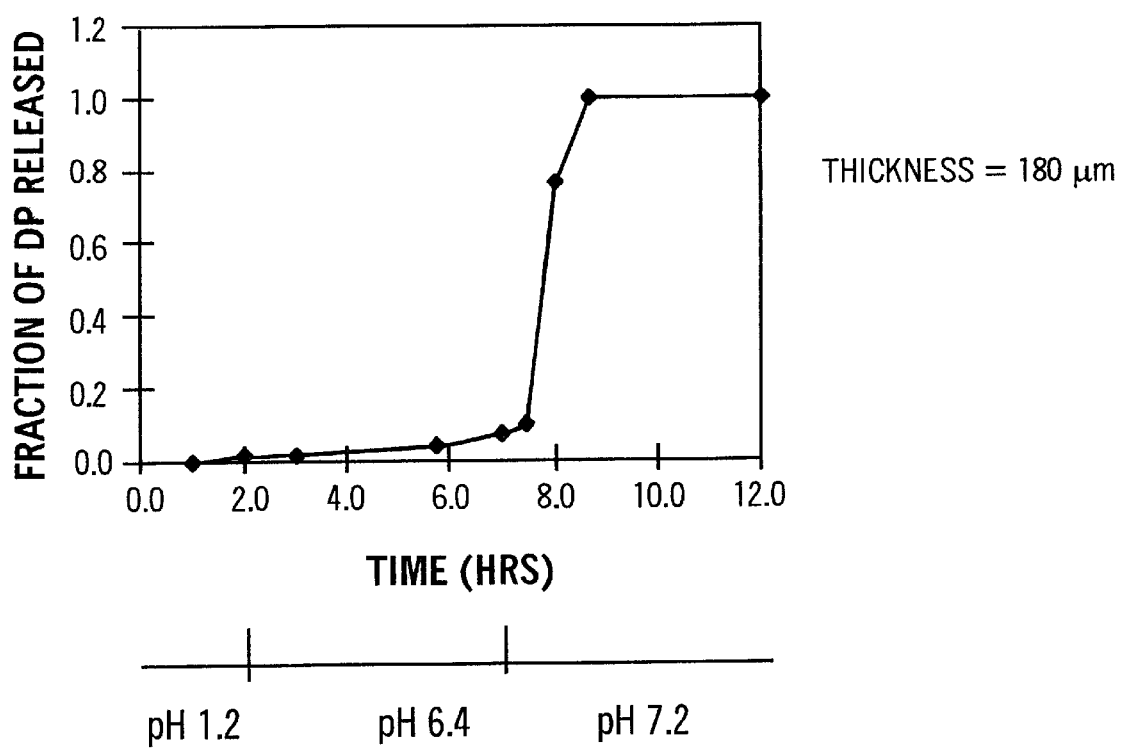
FIG. 11. Release profile for DP through a 180 µm thick EUDRAGIT™-S and urea film coating surrounding a tablet core comprising a physical mixture of DP and $SBE_7\beta$-CD.

By changing the film coating composition to EUDRAGIT™-S and urea, a delayed release formulation releasing DP at about pH 7.2 rather than at about 6.8 can be made (FIG. 11). The more basic pH corresponds to that found in the lower small intestine or the large intestine of a patient. Accordingly, one can prepare a delayed release formulation for enteric or colorectal release of a therapeutic agent comprising a solid core and a film coating, the solid core comprising a therapeutic agent and an SAE-CD and the film coating comprising a film forming agent which is a polymer with pH dependent solubility.

Figure 6:
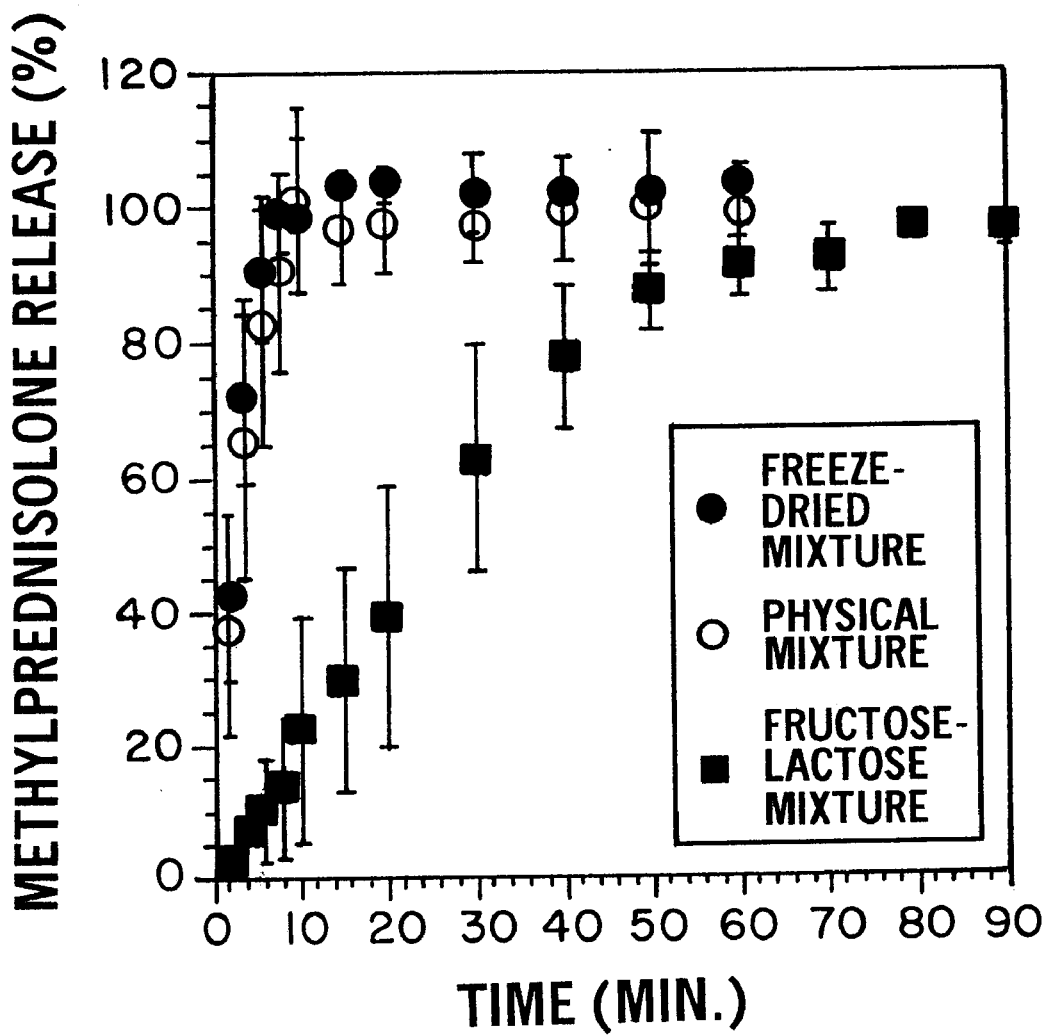
FIG. 6. Effect of $SBE_7\beta$-CD upon the MP release from an uncoated tablet core comprising either a freeze-dried complex or the physical mixture. A control wherein $SBE_7\beta$-CD is absent is also depicted.
Figure 7A:
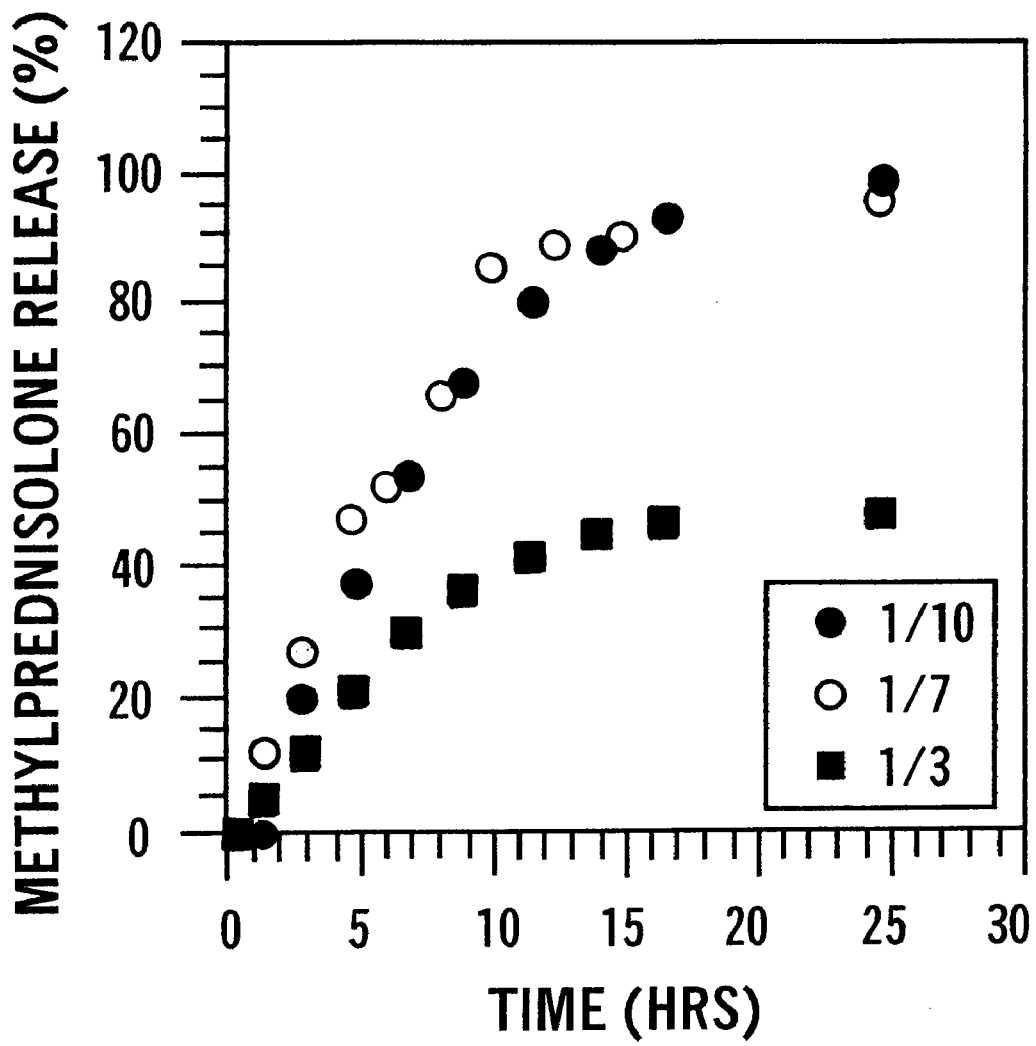
FIGS. 7a and 7b. Impact of the molar ratio of MP/$SBE_7\beta$-CD upon the MP release from film coated tablet cores comprising a physical mixture or a freeze-dried complex.
Figure 7B:
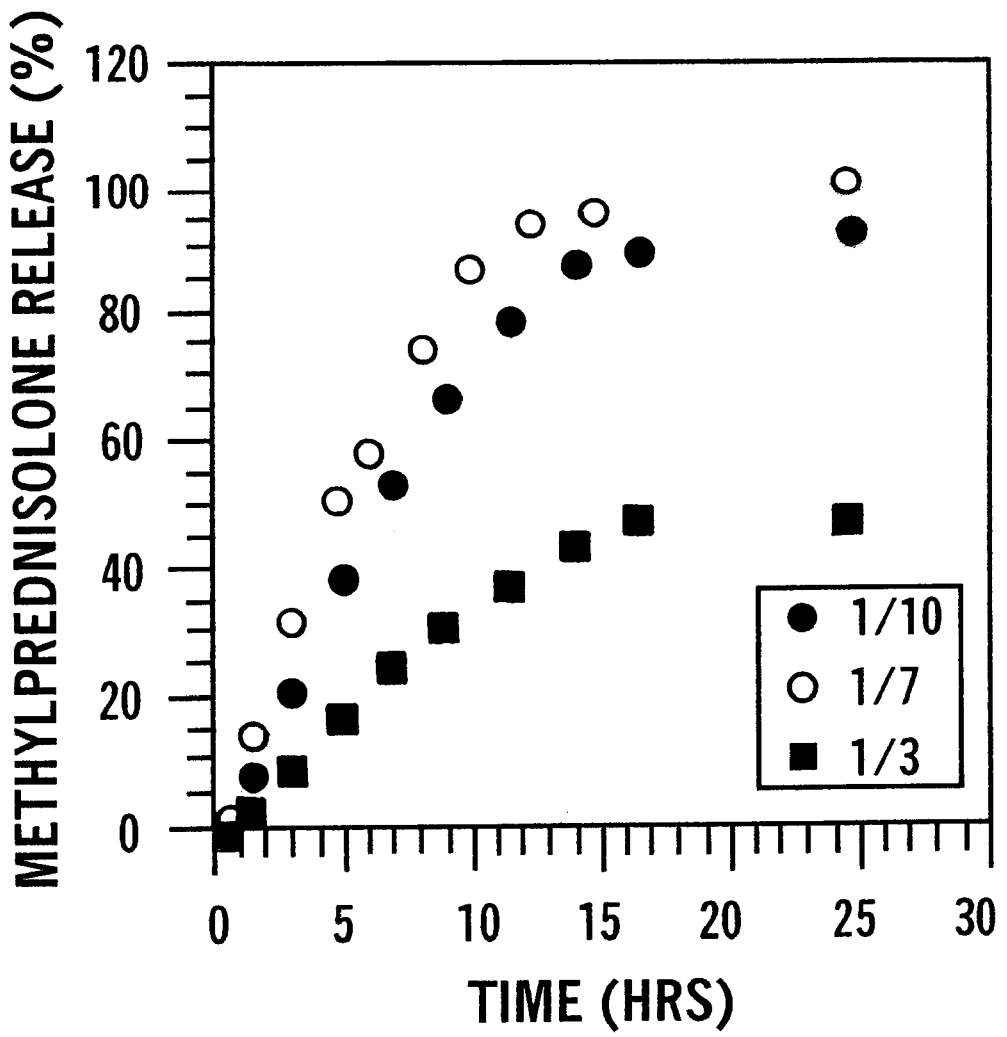
Figure 7C:
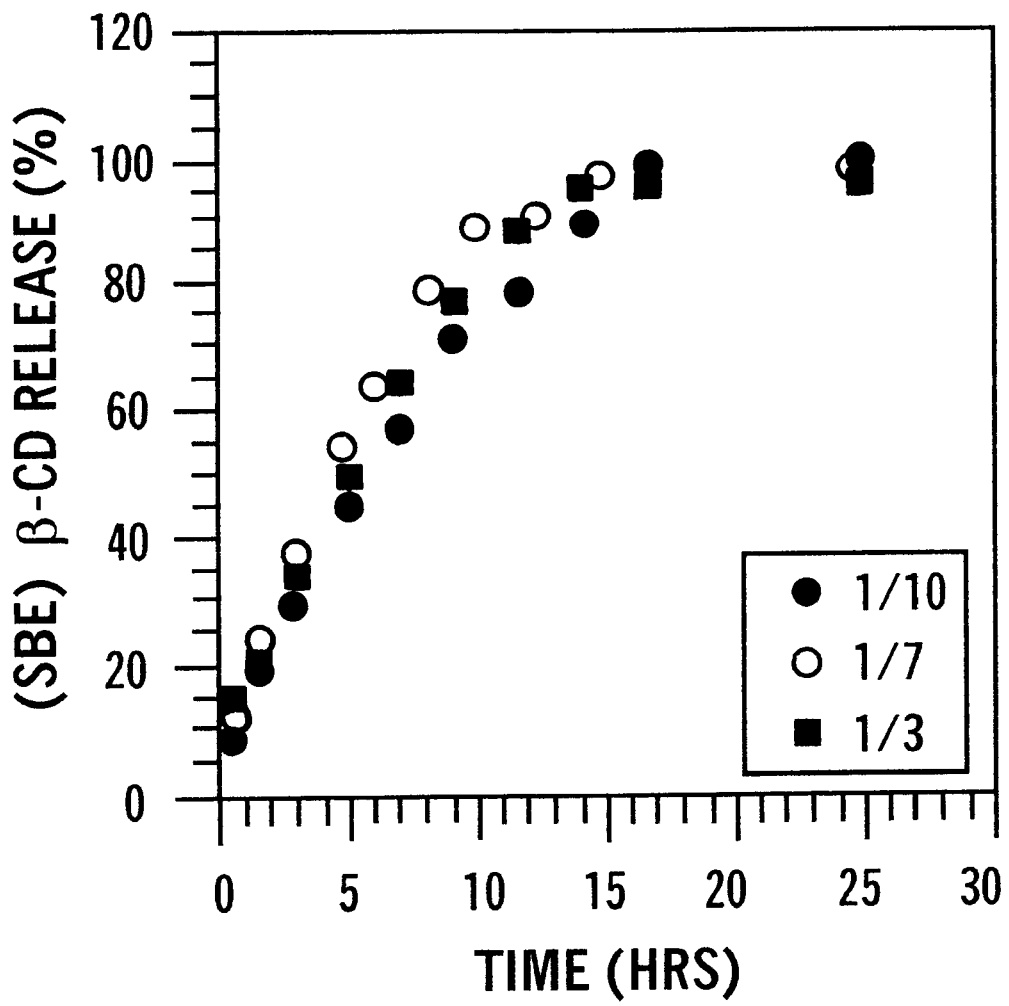
FIGS. 7c and 7d. Effect of MP/$SBE_7\beta$-CD molar ratio upon the release profile for $SBE_7\beta$-CD from film coated tablet cores comprising a physical mixture or a freeze-dried complex.
Figure 7D:
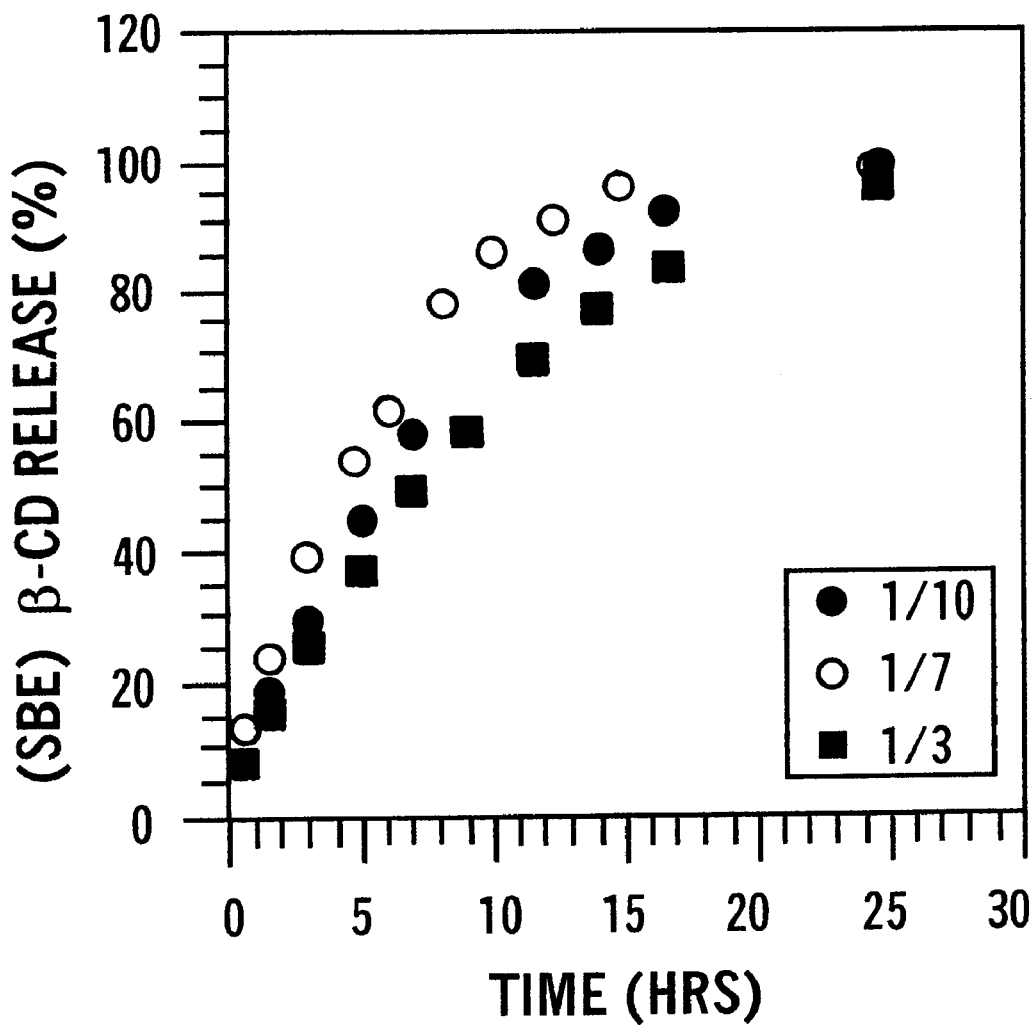

The film surrounding the solid core will affect the release of MP and SBE$_7$β-CD. In the embodiments of the invention wherein the film surrounding the core is absent, the core comprised of a physical mixture of SBE$_7$β-CD and MP can have the same or substantially the same release characteristics as a core comprised of a complex of the same. FIG. 6 depicts the release profile of MP from solid cores comprising the freeze dried complex (darkened circles), a physical mixture (hollow circles) and a fructose lactose-MP physical mixture (squares). In this example, the fructose-lactose mixture serves as an osmotic rather than solubilizing agent. The physical mixture exhibits substantially the same release profiles as the complex.

The molar ratio of MP/SBE7,B-CD can affect the release profile of a given dosage form. FIGS. 7a–7d depict the release profile of MP and SBE$_7$β-CD from film coated tablets comprising MP and SBE$_7$β-CD as a physical mixture (FIGS. 7a and 7c), and a freeze dried complex (FIG. 7b and 7d), where the MP/SBE$_7$β-CD mole ratios are 1/10, 1/7 and 1/3 (w/w). The results indicate that decreasing the relative amount of SBE$_7$β-CD decreases the observed release profile for MP. Thus, dosage forms having different release profiles are also prepared by controlling the MP/SBE$_7$β-CD ratio. The results also indicate that the physical mixture and the freeze dried complex have substantially the same release characteristics.

Figure 9:
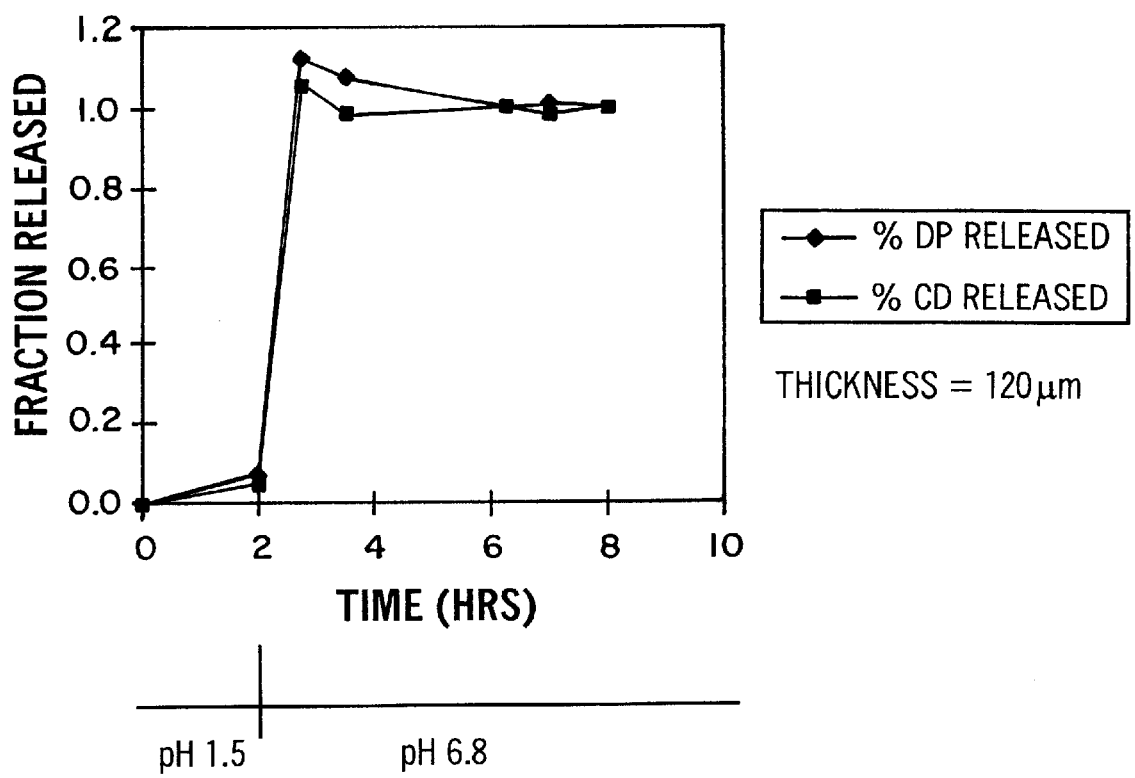
FIG. 9. Release profile for a delayed release formulation of dipyridamole (DP) from an EUDRAGIT™-L and urea membrane (120 µm thick) coated tablet core comprising a physical mixture of DP and $SBE_7\beta$-CD.

The film coating employed can comprise a polymer with a pH dependent solubility. FIG. 9 depicts the release profile for a delayed release formulation comprising a tablet core and film coating. The tablet core comprises a physical mixture of SBE$_7$β-CD and dipyridamole (DP). The film coating (150 μm) comprises EUDRAGIT™-L which exhibits pH dependent solubility. When the pH of the solution in which the tablet was immersed was raised from 1.5 to 6.8 after two hours, the SBE$_7$β-CD and DP displayed substantially the same release profile. The two hour delay corresponds to a dosage form which would release a major portion of the DP in the ileum or jejunum of a patient.

Figure 12:
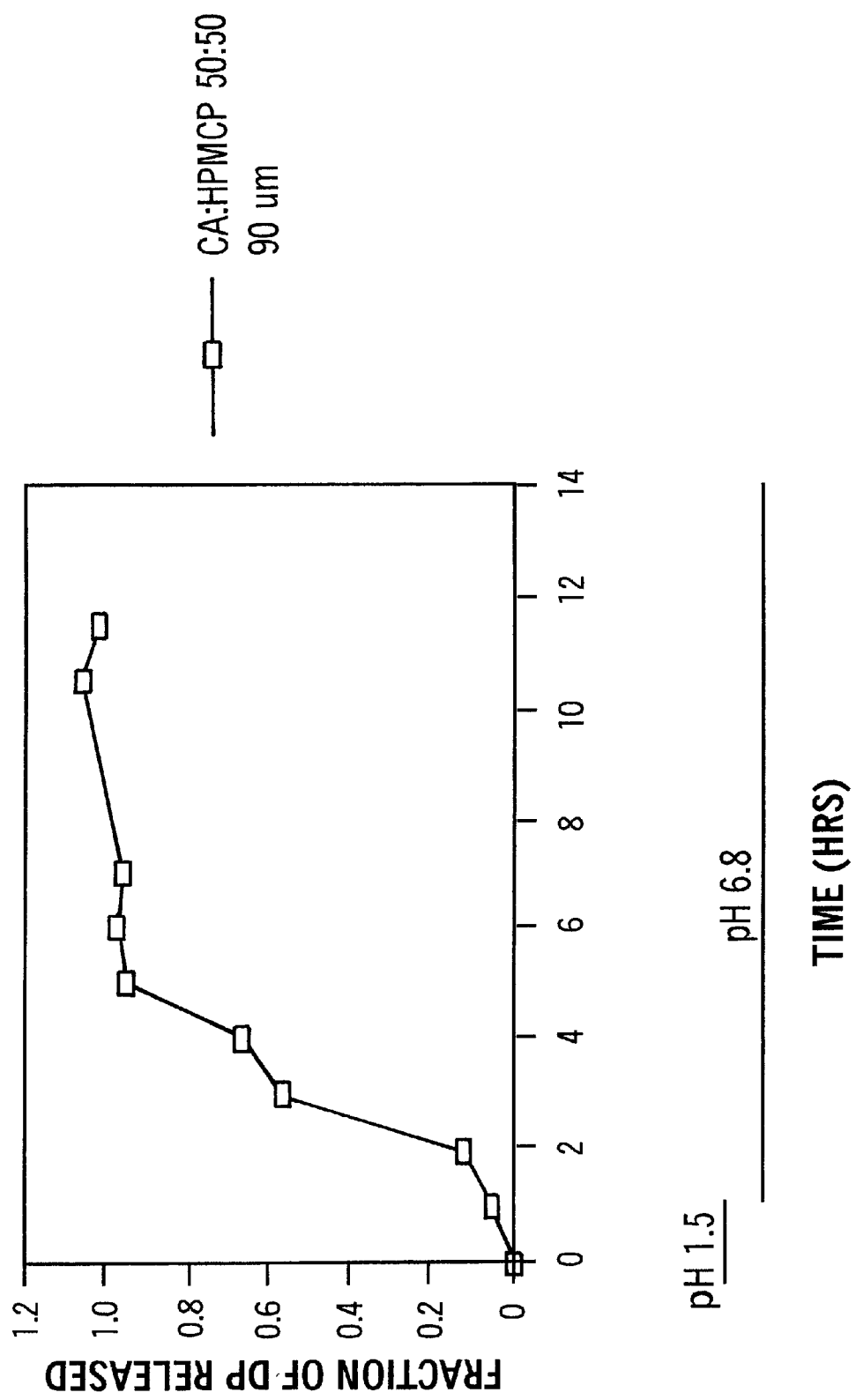
FIG. 12. Release profile for DP from a tablet core comprising a physical mixture of DP and $SBE_7\beta$-CD coated with a 90 µm thick cellulose acetate (CA) and hydroxypropyl methylcellulose phthalate (HPMCP) film.

The film coatings or membranes of the invention can comprise a combination of film forming agents. FIG. 12 depicts one embodiment of the invention wherein the film coating comprises a 1:1 mixture of cellulose acetate (CA) and hydroxypropyl methylcellulose phthalate (HPMCP), and the solid core comprises SBE$_7$β-CD and DP. This combination of film forming agents provides a formulation having a combined delayed and controlled release of therapeutic agent.

Figure 13:
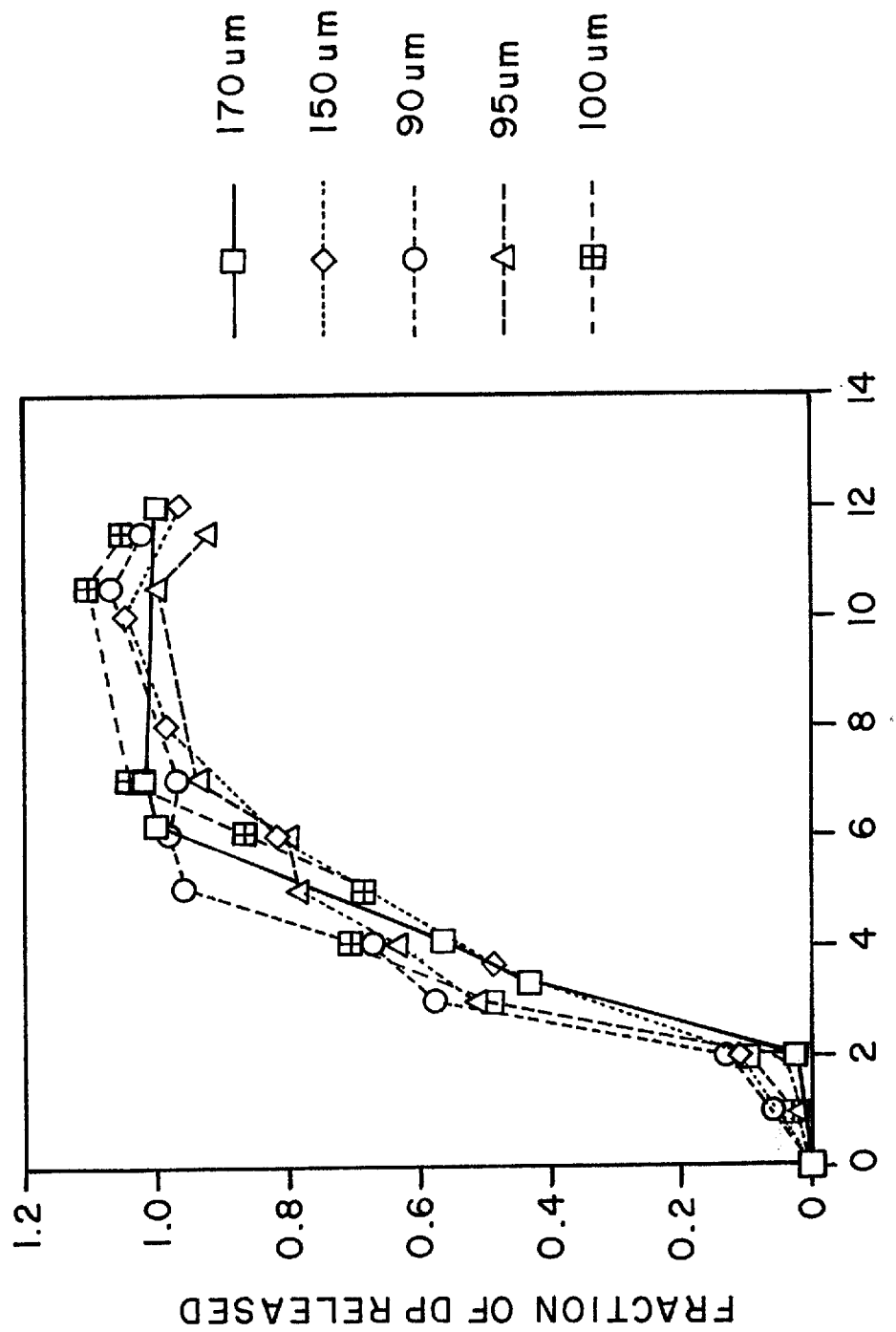
FIG. 13. Impact of film thickness upon DP release from a tablet comprising a physical mixture of DP and $SBE_7\beta$-CD surrounded by a CA and HPMCP (50:50) film.

Varying the film thickness from 90 μm to 170 μm did not appear to substantially affect the release profile of DP using film forming agents having a pH dependent solubility. Thus, in this embodiment, the invention provides a delayed and controlled release pharmaceutical formulation having a release profile that is only marginally dependent upon film thickness. (FIG. 13)

Figure 14:
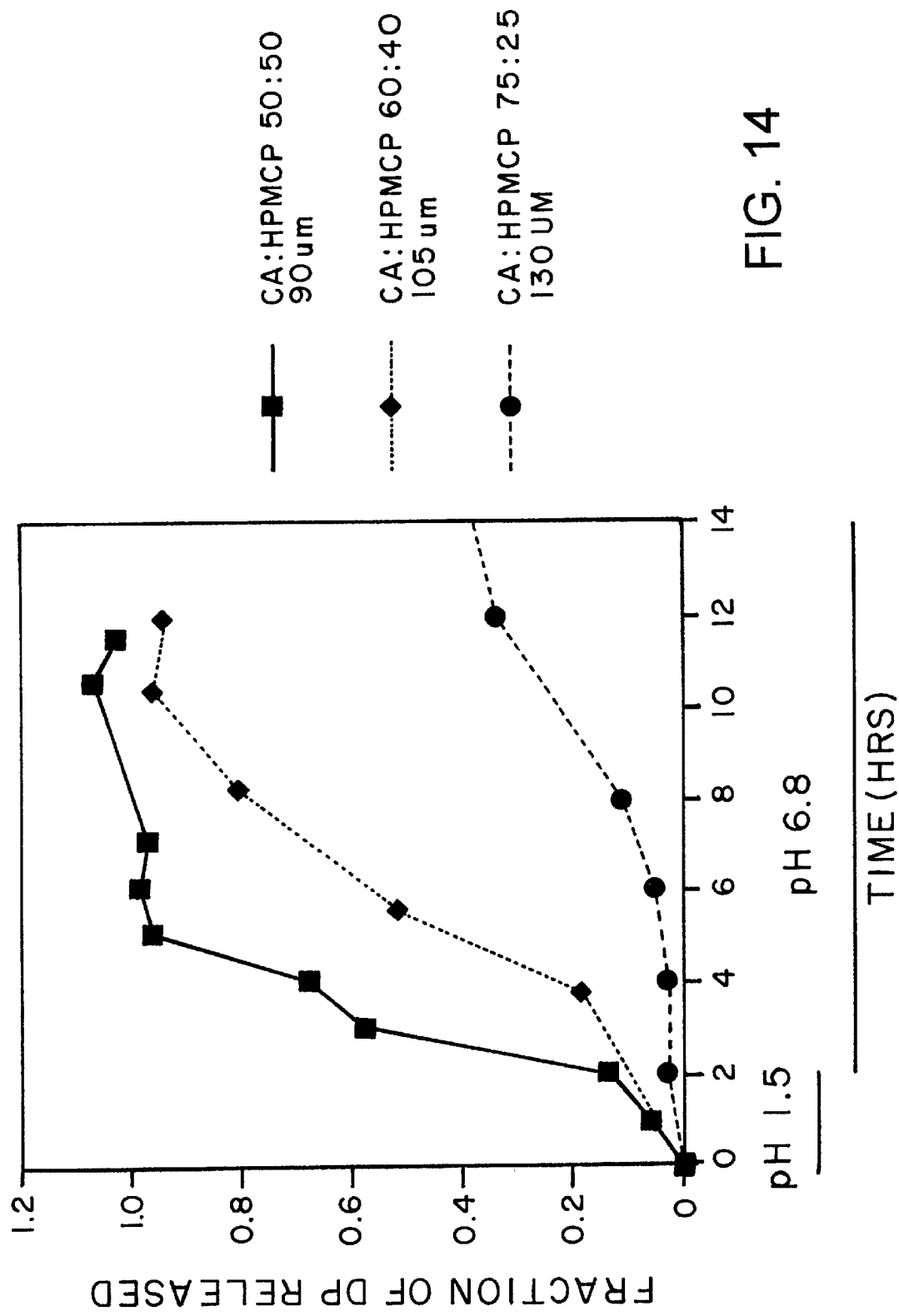
FIG. 14. Release profiles for DP from tablet formulations having a combined delayed and controlled release profile and the effect of film thickness and film composition thereupon.

Particular embodiments of the invention are made to exhibit delayed release, combined delayed and controlled release and/or controlled release. In the embodiment of FIG. 14, a DP/SBE$_7$β-CD containing tablet core was coated with a CA: HPMCP present in a variety of ratios and film thicknesses. The delayed release embodiment, indicated by the squares, comprised a 90 μm film coating which comprised a 1:1 ratio of CA: HPMCP. The combined delayed and controlled release embodiment, indicated by the diamonds, comprised a 105 μm film coating which comprised a 6:4 ratio of CA: HPMCP. Thus, by altering the ratio of CA:HPMCP, one can control the relative contribution of controlled and delayed release to the overall release profile of the dosage form.

It should be noted that in the absence of an SAE-CD according to the present invention, a suitable drug release profile will not be obtained for the therapeutic agents exemplified herein. For example, a tablet core comprising DP, citric acid and fructose-lactose surrounded by a CA:HP-MCP (50:50) 120 μm thick film, no release of DP was obtained. In a further example wherein the same tablet core was surrounded by an EUDRAGIT™-L and urea (50:50) 120 μm thick film, incomplete release of DP was observed.

Accordingly, the present invention is also a pharmaceutical formulation having a delayed release, controlled release or combined delayed and controlled release profile comprising a tablet core and a film coating around the tablet core, the tablet core comprising a physical mixture of a therapeutic agent and a SAE-CD, and the film coating comprising a combination of film forming agents.

Additional osmotic pump tablets were prepared according to Example 2 and their dissolution characteristics evaluated. These tablets included a DP/SAE-CD-containing tablet core surrounded by film coating comprising one or more of the following: cellulose acetate, ethyl cellulose, wax, EUDRAGIT™ E100, EUDRAGIT™ RS, and EUDRAGIT™ RL, EUDRAGIT™ L, EUDRAGIT™ S, cellulose acetate phthalate, hydroxypropyl methylcellulose phthalate and HPMC acetate succinate. The pore forming agent evaluated included poly(ethylene glycol) 3350 (PEG 3350), sorbitol, sucrose, polyols, xylitol, mannitol, carbohydrates, sugars, lactose, maltose, dextrose, water soluble cyclodextrins, and urea. Other compounds suitable as film forming agents include cellulose acetate butyrate, cellulose acetate propionate, cellulose propionate, HPMC, carrageenan, cellulose nitrate, hydrophilic cellulosic agents, hydroxypropylcellulose, methylcellulose, hydroxyethylcellulose, ethylcellulose, polyvinyl acetate and latex dispersions, poly-acids, enteric polymers, polysaccharides, acacia, tragacanth, guar gum, gelatin, proteins, albumin, polylactic acid, biodegradable polymers, polyglutamic acid and combinations thereof.

Figure 15:
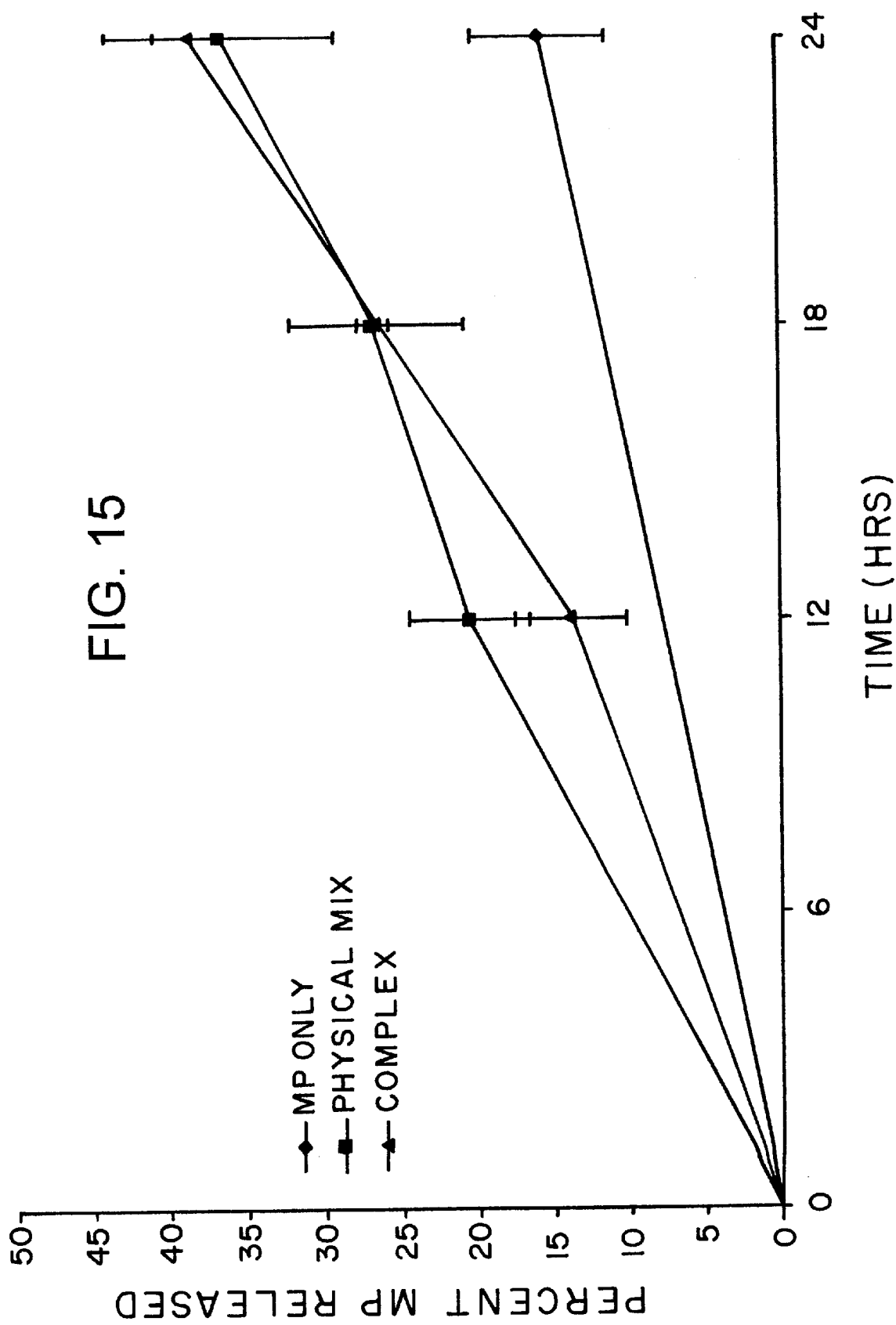
FIG. 15. Release profile for methylprednisolone (MP) from tablet formulations comprising a physical mixture and preformed complex of MP and $SBE_7\beta$-CD surrounded by a coating comprising a composition of EUDRAGIT™ RS30D and EUDRAGIT™ RL30D but no pore forming agent.

As previously mentioned, it is not required that a pharmaceutical formulation according to the invention comprise a coated core wherein the coat comprises a film forming agent and a pore forming agent. In the example of FIG. 14, the rate of release and the total amount released of DP is controlled by both film thickness and film composition whereby increasing the amount of CA with respect to the HPMCP resulted in an overall decrease in the rate of delivery of DP and a decrease in the overall amount of DP released. However, in the example of FIG. 15, MP is released from a tablet formulation comprising a coat consisting of a film forming agent, a plasticizer, and an antiadherent, but no pore forming agent. In this formulation, the coat comprises a combination of Eudragit™ RS and Eudragit™ RL in a 9 to 1 weight ratio and the coating on the core of the tablet comprises approximately 5 wt.% of the total weight of the tablet. Accordingly, the present invention also provides controlled release pharmaceutical formulations consisting essentially of a core surrounded by a coat which comprises a film forming agent wherein the coat controls the rate of delivery of the drug even absent a pore forming agent in the coating.

Figure 16:
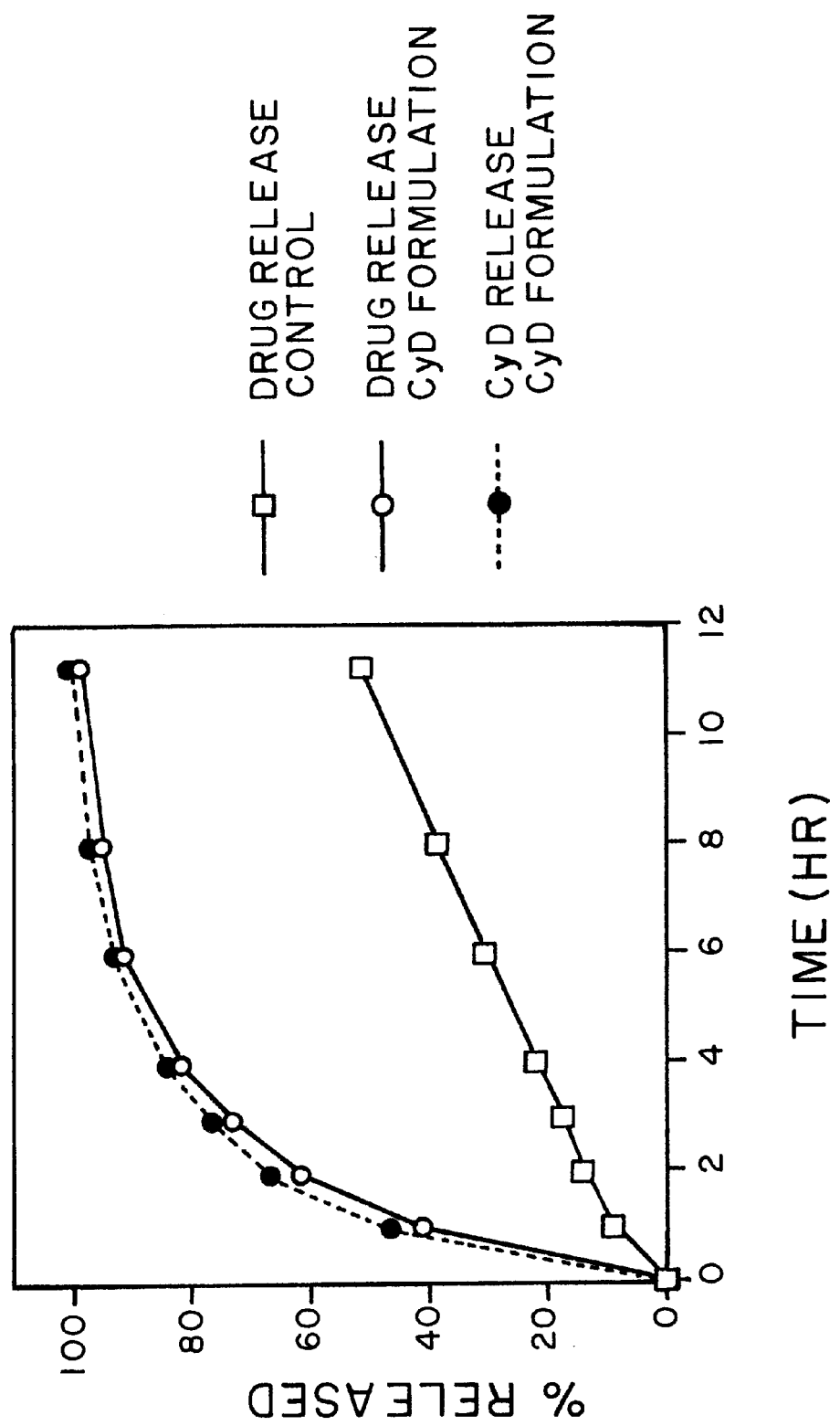
FIG. 16. Release profiles for prednisolone (PD) from tablet formulations having a core comprising a physical mixture of PD and $SBE_7\beta$-CD and a rate modifier, wherein the tablet is uncoated.

At least one aspect of the invention provides a controlled delivery solid pharmaceutical formulation consisting essentially of an uncoated core wherein the core comprises a controlled release matrix which includes a release rate modifier, a therapeutic agent, and a sulfoalkyl ether cyclodextrin. Unlike other embodiments of the present invention, this particular embodiment can provide the controlled release of the poorly water soluble drug prednisolone (PD) absent a release rate modifying coat. In the example of FIG. 16, the release rate modifier is hydroxypropyl methylcellulose (HPMC). In the absence of the cyclodextrin, only approximately 50% by weight of the PD is released after eleven hours; however, addition of the SAE-CD effects a greater than 90% delivery of the drug in approximately six hours and substantially complete delivery of the drug in eleven hours.

Figure 17:
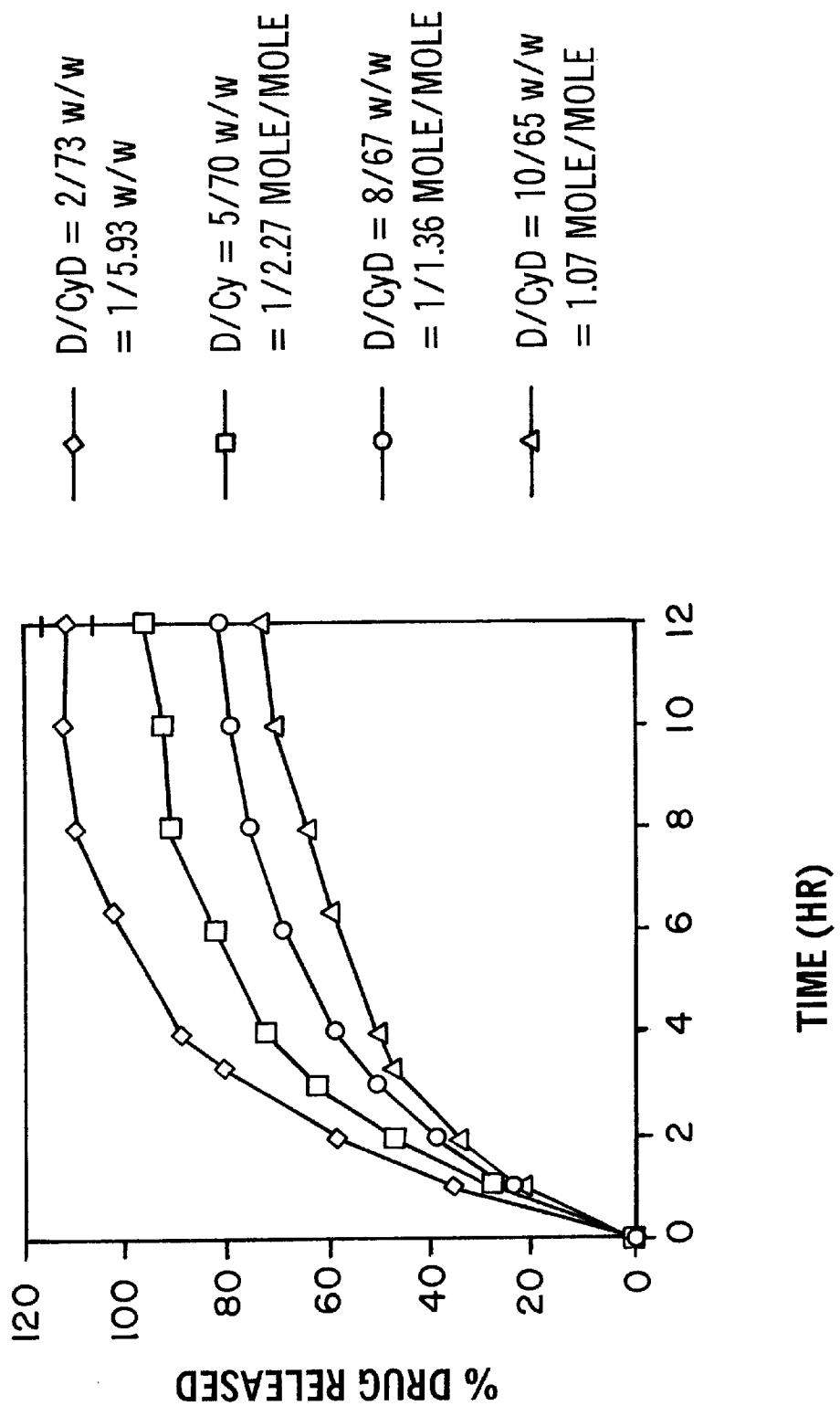
FIG. 17. Release profiles for PD from tablet formulations consisting essentially of cores having different ratios of cyclodextrin to therapeutic agent.

The effect of changing the ratio of therapeutic agent to sulfoalkyl ether cyclodextrin is exemplified in FIG. 17 wherein the amount of prednisolone and HMPC in an uncoated core is kept constant while the amount of $SBE_7\beta$-CD and lactose monohydrate are varied. Specifically, the PD is kept constantly at 5% by weight of the formulation and the HMPC is kept constant at approximately 25% by weight of the formulation. The cyclodextrin and lactose amounts are varied such that they will comprise approximately 70% by weight of the formulation in the exemplary formulations of FIG. 17. Generally as the amount of SAE-CD is decreased and the amount of lactose is increased in the formulation, the rate of delivery of the PD and the overall amount of PD delivered decrease and the rate of delivery of the SAE-CD increases. Stated otherwise, as the PD/SAE-CD ratio is increased, the release rate of the drug is decreased, and the release rate of the SAE-CD is increased. Accordingly, one embodiment of a controlled release pharmaceutical formulation according to the invention includes an uncoated core comprising an SAE-CD, a therapeutic agent, and a release rate modifier. Exemplary formulations include those formulations wherein approximately 40% of the drug, preferably 60% of the drug, more preferably 80% of the drug, is delivered within four hours and 60% of the drug, preferably 80% of the drug, and more preferably 90% of the drug, resepectively is delivered within eight hours after administration of the formulation.

Figure 18:
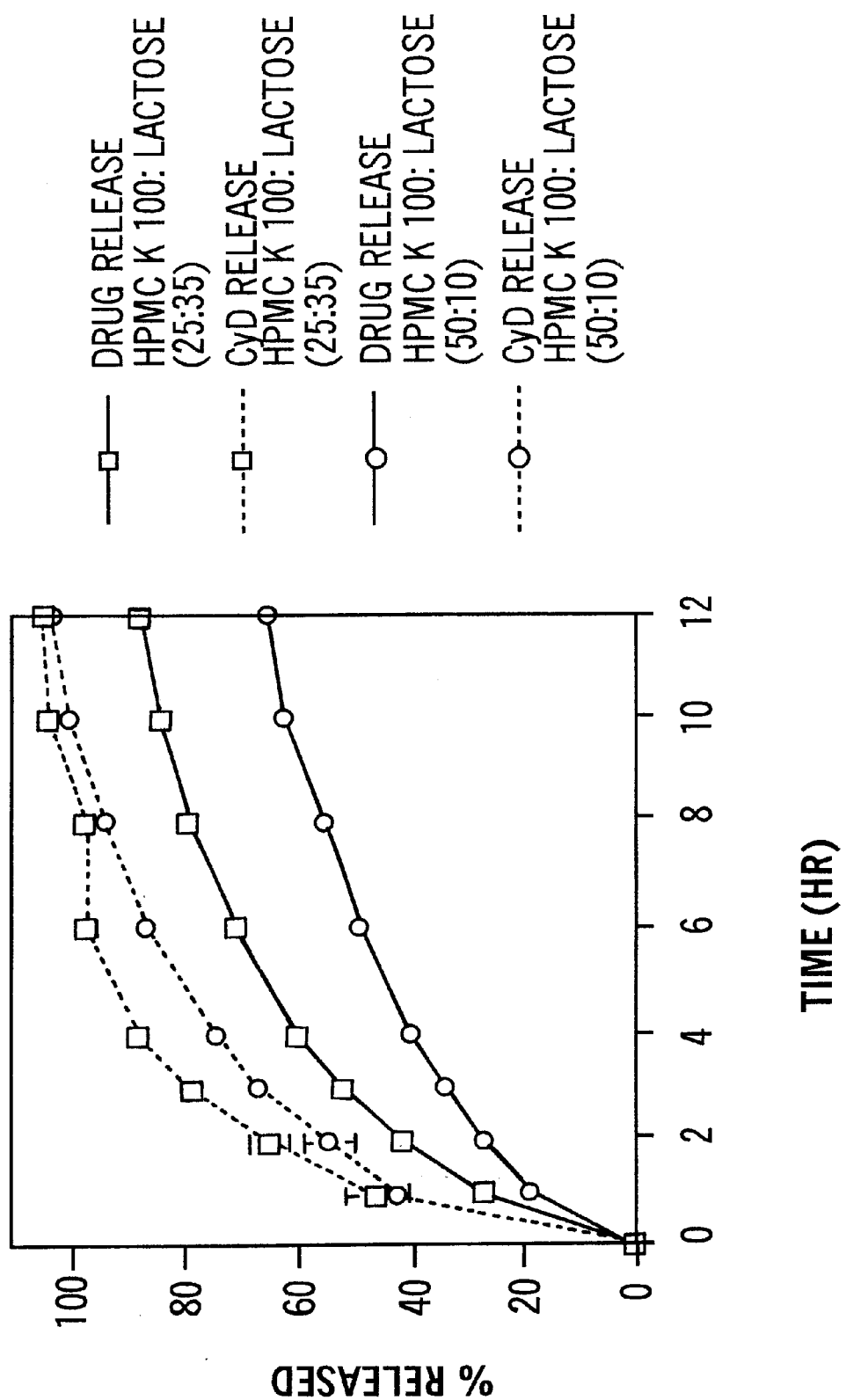
FIG. 18. Release profiles for PD from tablet formulations comprising uncoated cores containing constant amounts of cyclodextrin and PD but different amounts of rate modifier.

In the controlled release formulation according to the invention wherein the core is uncoated, the ratio of release rate modifier to either one or both of the therapeutic agent or SAE-CD will have an impact upon the rate of delivery of the drug and the overall amount of drug delivered. Accordingly, FIG. 18 depicts release profiles for various formulations wherein the amount of drug and cyclodextrin in the formulation have been kept constant and the amount of release rate modifier (HPMC) and diluent (lactose) have been varied. Generally, as the ratio of release rate modifier to drug is increased, the release rate of the drug is decreased, and as the ratio of release rate modifier to cyclodextrin is increased, the release rate of the cyclodextrin is decreased. In the specific example of FIG. 18, in this embodiment, when the ratio of release rate modifier to drug is approximately 10:1, approximately 40–50% of the drug will be released in about six hours after administration and approximately 55–60% of the drug will be released 12 hours after administration. When the ratio of release rate modifier to drug is approximately 5:1, the formulation will release approximately 65–75% of the drug after about six hours and approximately 75–90% of the drug 12 hours after administration. PD comprises 5% by weight of the formulation, SAE-CD comprises 35% by weight of the formulation, and increasing the amount of HPMC in the formulation is varied from 25% by weight to 50% by weight.

Figure 19:
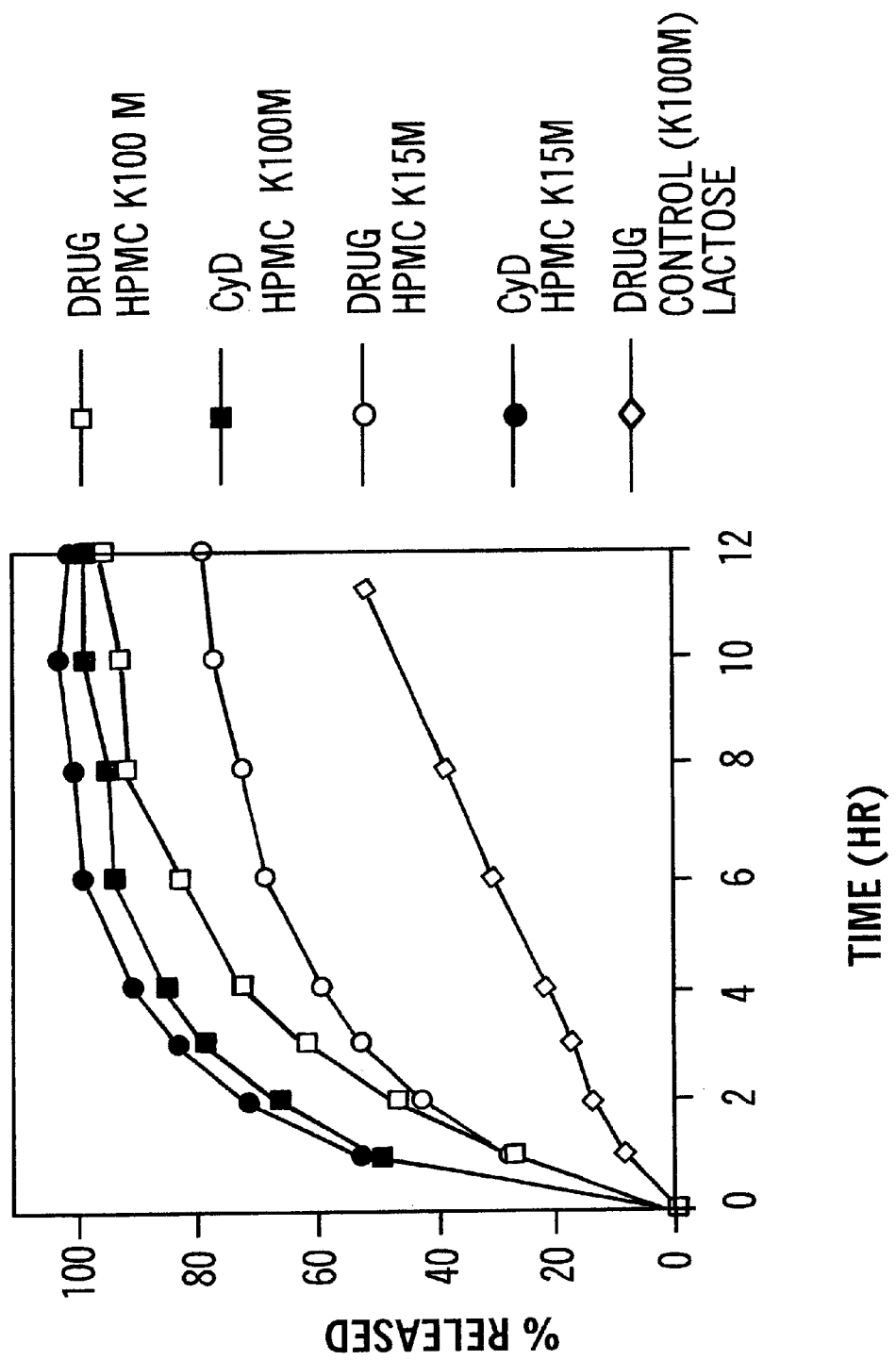
FIG. 19. Release profiles for PD from tablet formulations containing uncoated cores comprising release modifiers having different viscosity and solubility characteristics as well as formulations containing different drug to rate modifier polymer ratio.

The embodiments of the formulation according to the invention which comprise an uncoated core for releasing a drug at a controlled rate are generally affected by the molecular weight and/or the viscosity of a release rate modifier used to comprise the core. It is generally accepted that an increase in viscosity for a polymer can correspond to an increase in the molecular weight of the polymer, an increase in the branching of the polymer or an increase in the degree of substitution of the polymer. For example, FIG. 19 depicts an uncoated core formulation wherein the core comprises 5% by weight of PD, 70% by weight of SAE-CD and 25% by weight of HPMC. The HPMC includes either HPMC K100M (having a viscosity of 100,000 cps) or HMPC K15M (having a viscosity of 15,000 cps). As the viscosity of the release rate modifier is increased, the rate of release of the PD is increased. The control sample which includes HPMC K100M and no cyclodextrin releases approximately 30% by weight of the PD in six hours and approximately 50% by weight of the PD in eleven hours. Surprisingly, as the 1. viscosity of the HPMC is increased from 15,000 to 100,000, the rate of delivery of the PD and the overall amount of PD delivered increases; whereas, the rate of delivery of the cyclodextrin and the overall amount of the cyclodextrin delivered decreases. This behavior is quite unexpected as it is generally expected in the art that the rate of delivery of components in a controlled release matrix will decrease as the viscosity of the release rate modifier increases. Accordingly, this embodiment of the invention provides a controlled release formulation wherein the release rate modifier is present in an amount sufficient to render the release rate of the drug dependent upon the viscosity of the release rate modifier.

Figure 20:
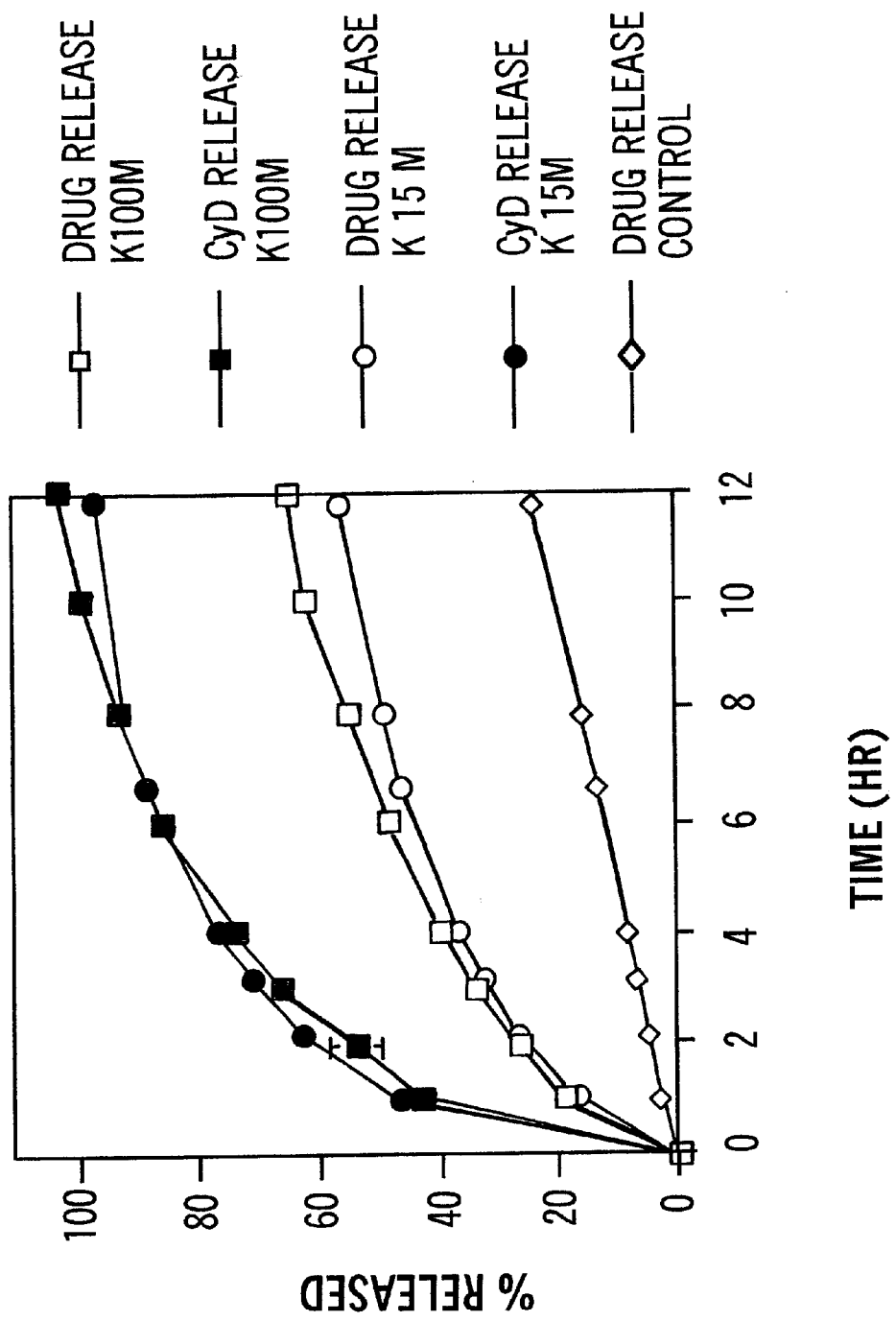
FIG. 20. Release profiles for PD from tablet formulations containing uncoated cores comprising release modifiers having different viscosity and solubility characteristics as well as formulations containing different drug to rate modifier polymer ratio.
Figure 21:
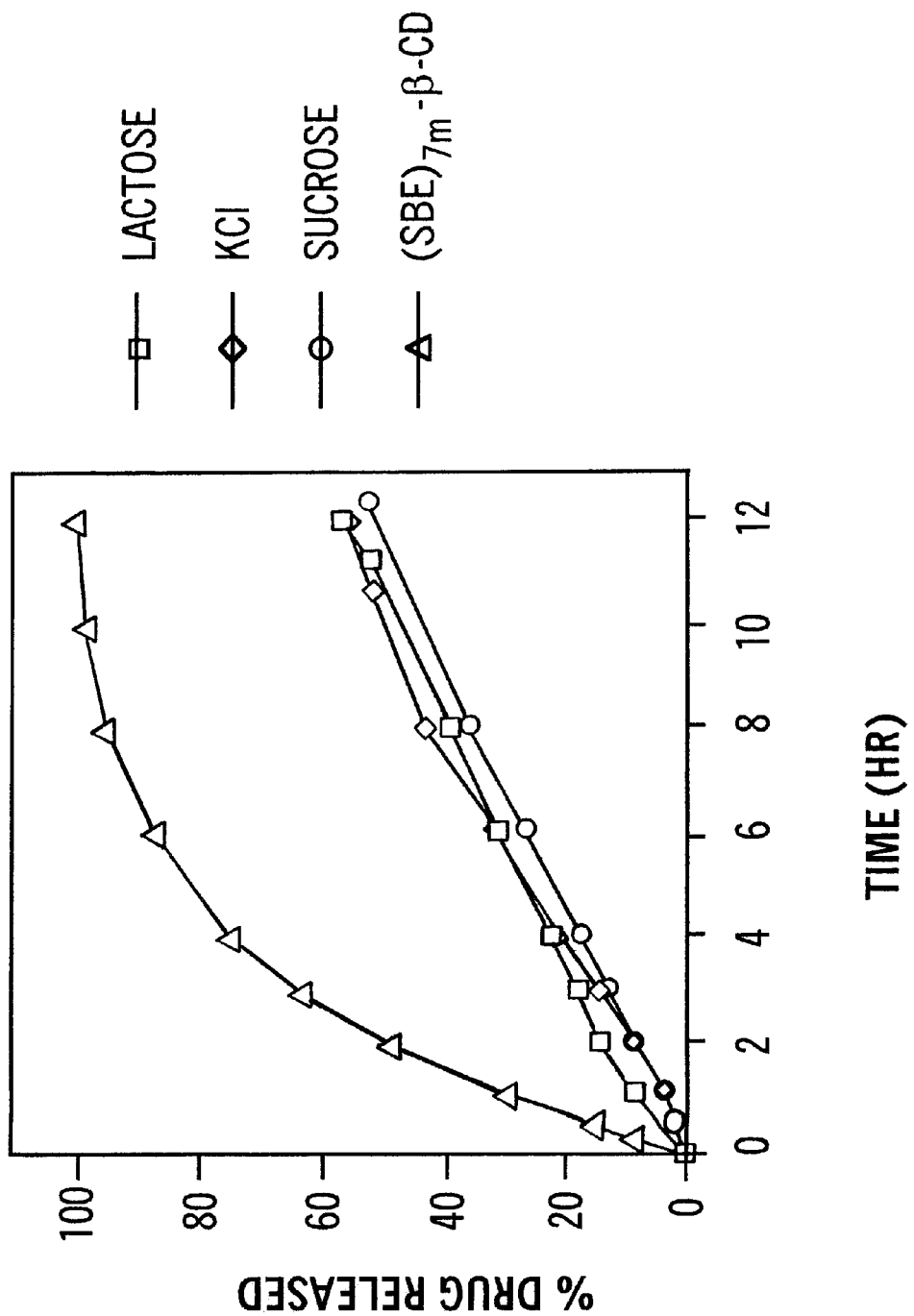
FIG. 21. Release profiles for PD from tablet formulations having a core comprising a physical mixture of PD, a rate modifier and one of $SBE_7\beta$-CD, KCl, sucrose or lactose, wherein the tablet is uncoated.
Figure 22:
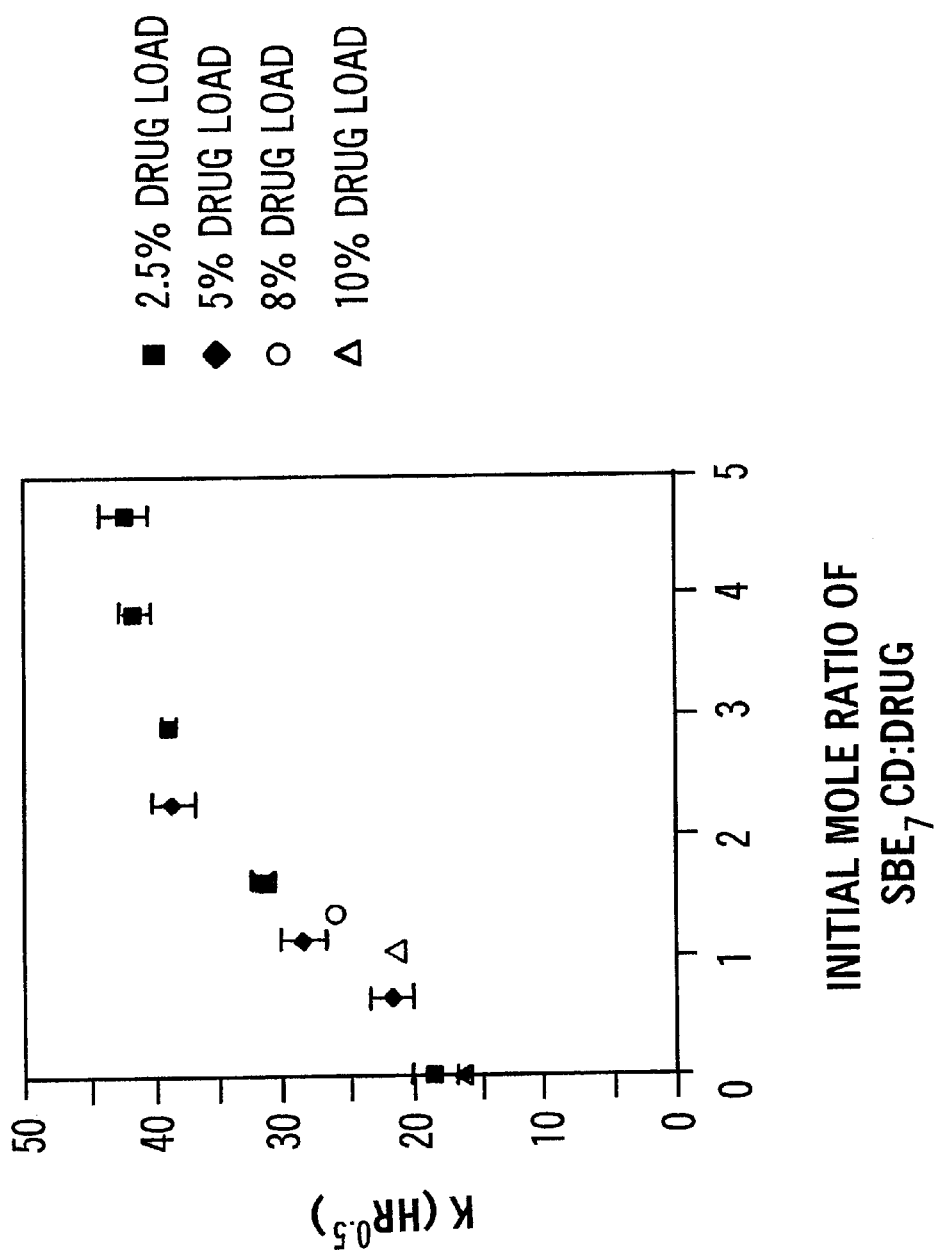
FIG. 22. Release rate profiles for PD from tablet formulations wherein the ratio of drug: $SBE_7\beta$-CD is varied.

FIG. 20 includes release profiles for uncoated controlled release core formulations comprising 5% by weight of PD, 35% by weight of SAE-CD, 50% by weight of HPMC and 10% by weight of lactose wherein the HPMC viscosity has been increased from 15,000 to 100,000 cps. In this particular example, which includes a high concentration of HPMC relative to the cyclodextrin and the drug, the rate of delivery and the overall amount delivered of the drug and SAE-CD appear to be substantially independent of the viscosity of the HPMC. Accordingly, the controlled release uncoated core formulation according to the invention can provide release of a therapeutic agent wherein about 60% of the therapeutic agent has been released within about four hours and about 80% of the drug has been released within about 10 hours or wherein about 80% of the formulation has been released within about 4 hours and greater than 90% of the formulation has been released within about 10 hours. The invention can also provide a controlled release uncoated formulation wherein approximately 40% of the drug is released within four hours and approximately 50% of the drug is released within 8 hours. Stated otherwise, one embodiment of the formulation comprises a release rate modifier present in an amount sufficient to render the release rate of the drug substantially independent of the viscosity of the release rate modifier.

FIGS. 19 and 20 indicate that when higher concentrations of the release rate modifier are present in the formulation, the release rate of the drug in the formulation will be substantially independent of the viscosity of the release rate modifier; whereas, when lower concentrations of the release rate modifier are present in the core, the release rate of the drug from the core will be substantially dependent upon the viscosity of the release rate modifier. Stated otherwise, increasing the amount of release rate modifier in the core generally decreases the dependence of the release rate of the drug upon the molecular weight or viscosity of the release rate modifier.

Another aspect of the invention provides a multi-layered controlled release solid pharmaceutical formulation or dosage form comprising at least a first layer comprising a physical mixture of a therapeutic agent and an SAE-CD and at least a second layer comprising a release rate modifier. In this embodiment as with all the others of the present invention, a major portion of the therapeutic agent is not complexed with the SAE-CD. The components of the at least first and second layers will cooperate to provide a controlled delivery of the therapeutic agent. In the present embodiment, the formulation can comprise two, three, four or more layers which are compressed individually, simultaneously, sequentially or otherwise to form a formulation have a desired release profile of the therapeutic agent. In a preferred embodiment, the multi-layered formulation will comprise a middle first layer comprising a therapeutic agent and SAE-CD sandwiched between two second layers, each comprising a release rate modifier. The first and second layers according to the invention can comprise additional pharmaceutical excipients and components known to those of ordinary skill in the art.

While it is an object of the invention to provide controlled release solid pharmaceutical formulations comprising a combination of a SAE-CD and therapeutic agent wherein a major portion of the therapeutic agent is not complexed with the SAE-CD, the present formulations can further include additional compositions wherein the therapeutic agent is complexed with the SAE-CD. For example, one embodiment of the invention can comprise a core containing a first composition and a second composition, wherein the first composition comprises a physical mixture of an SAE-CD and a therapeutic agent, wherein a major portion of the therapeutic agent is not complexed with the SAE-CD, and the second composition comprises a preformed complex of the SAE-CD and the therapeutic agent.

Figure 23A:
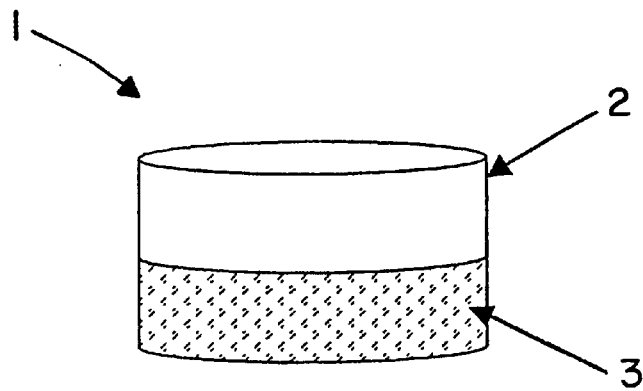
FIG. 23a depicts a first embodiment of a two-layered tablet according to the invention.
Figure 23B:
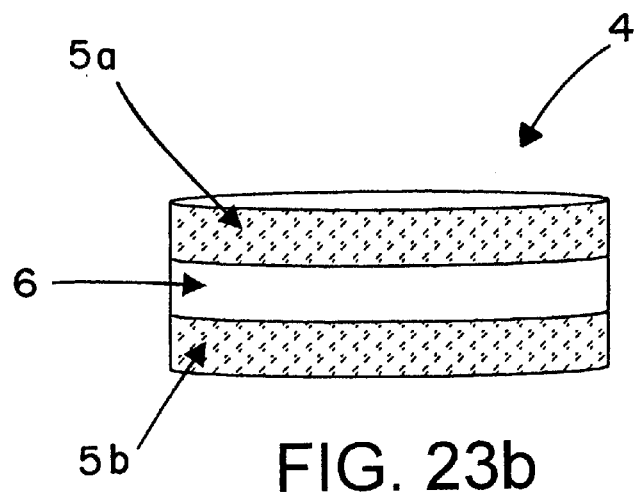
FIG. 23b depicts a first embodiment of a three-layered tablet according to the invention.

Example 8 details a method of preparing an exemplary embodiment of a multi-layered tablets according to the invention comprising at least one immediate release layer adjacent a controlled release layer. FIG. 23a depicts a bilayered tablet (1) comprising an immediate release layer (3) containing a predetermined amount of drug and SAE-CD, together present as a physical mixture, and a rapid release matrix and a controlled release layer (2) containing a predetermined amount of a physical mixture of a drug, an SAE-CD and a release rate modifier. The immediate release layer readily disintegrates and releases the drug into the surrounding milieu following administration to the patient or addition of the tablet to a dissolution medium. FIG. 23b depicts a three-layered tablet wherein a controlled release layer (6), prepared as described in Example 8, is sandwiched between two immediate release layers (5a, 5b), prepared as described in Example 8. Note that the immediate release layers of FIG. 23b comprise a preformed indomethacin/SAE-CD complex. The bi-layered and three-layered tablets can be coated with a finish, enteric or controlled release coating if desired.

In another embodiment, the multi-layered controlled release formulation comprises at least first, second and third layers wherein the first layer contains a first composition comprising a physical mixture of an SAE-CD and a therapeutic agent, wherein a major portion of the therapeutic agent is not complexed with the SAE-CD, the second layer contains a second composition comprising a preformed complex of the SAE-CD and a therapeutic agent, and the third layer comprises a release rate modifier. In this particular embodiment, the third layer can cover either one or both of the first and second layers.

Figure 24:
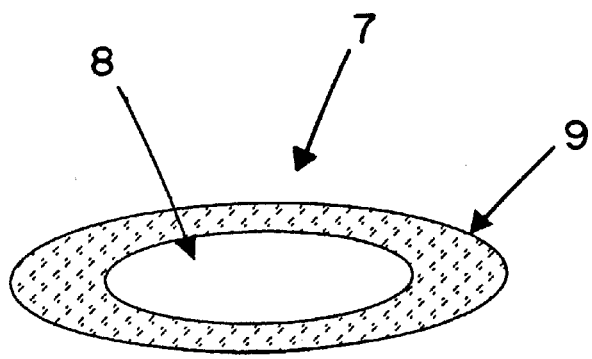
FIG. 24 depicts a second embodiment of a controlled-release tablet according to the invention.

FIG. 24 depicts another embodiment of the controlled release formulation (7) of the invention wherein a controlled release core (8), containing a physical mixture of drug and SAE-CD, is surrounded by a compression coating (9) containing a preformed complex of drug and SAE-CD.

The controlled release formulations of the invention also include physical mixture particulate or granular formulations wherein a first group of particles contains a physical mixture of a first therapeutic agent, a first sulfoalkyl ether cyclodextrin and a release rate modifier and a second group of particles contains an inclusion complex of a first therapeutic agent and a second sulfoalkly ether cyclodextrin. The first group of particles will preferably deliver the first therapeutic agent in a controlled manner, and the second group of particles will preferably deliver the second therapeutic agent in a rapid manner. The first and second therapeutic agents can be the same or different. Likewise, the first and second sulfoalkyl ether cyclodextrins can be the same or different. The particulates will preferably include additional pharmaceutically acceptable excipients. If a delayed and controlled delivery of the second therapeutic agent is desired, the particles of the second group will be coated with a delayed release coating. The delayed release can be pH, erosion, or solubility controlled. Delayed release coatings include those described herein as well as other coatings known to those of ordinary skill in the art.

Osmotic pump formulations made according to the examples below will generally comprise a semipermeable coating surrounding a core comprising a physical mixture of a therapeutic agent, an SAE-CD, and a pharmaceutically acceptable carrier, wherein a major portion of the therapeutic agent is not complexed with the SAE-CD and the membrane has a passageway therethrough for communicating the core to an environment of use. The core can also include an osmagent and pharmaceutically acceptable excipients. The semipermeable membrane can include one or more pore forming agents to render the membrane porous thereby permitting diffusion of therapeutic agent through the membrane and resulting in a dual function osmotic pump.

In the examples detailed below wherein a formulation comprises a film coating around a core, the film can also include a passageway therethrough for communicating the core to an environment of use. For example, a passageway is formed in the film by drilling with a laser or drill bit. If the film is porous, i.e. permits diffusion of a drug therethrough, and also includes a passageway, the formulation will deliver drug by combined osmotic and diffusional means. If the film is semipermeable, i.e. does not permit diffusion of a drug therethrough, and includes a passageway, the formulation will deliver drug by osmotic means.

The term "osmagent" means a compound or group of compounds that generate an osmotic pressure across the membrane of an osmotic pump when included within the core of the osmotic pump and when exposed to water imbibed from an environment of use. Such osmotic agents include, for example, salts, water soluble compounds, sugars and other such agents known to those of ordinary skill in the art. The SAE-CD and other hydrophilic or ionized compounds or polymers can also serve as osmagents.

Figure 25:
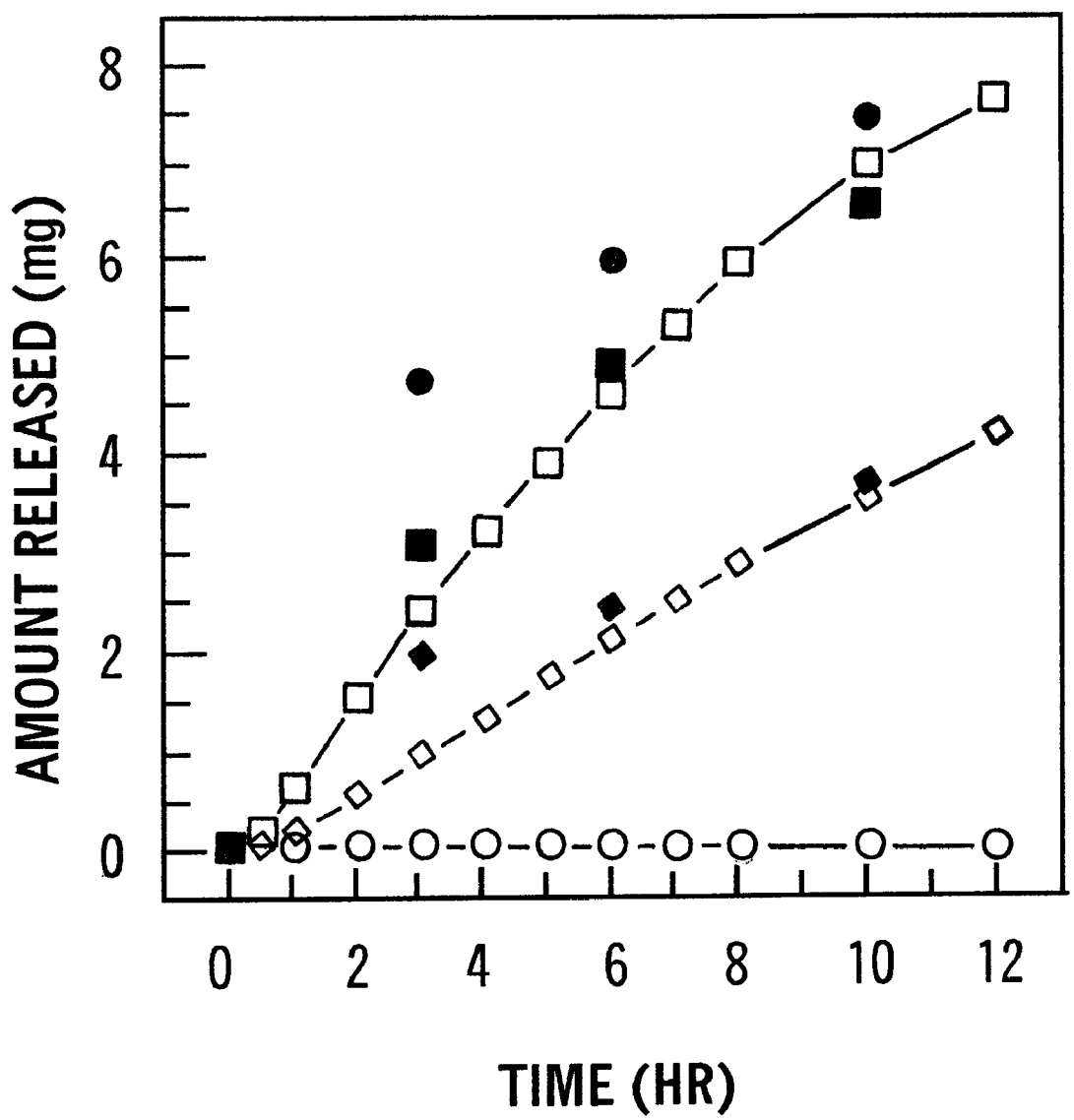
FIG. 25 depict release profiles for testosterone (TS) and excipients from various osmotic pumps, one of which is prepared according to the invention.

Example 11 describes the preparation of an osmotic pump which delivers testosterone (TS) into an environment of use by combined diffusional and osmotic means. FIG. 25 depicts the comparative release profiles of TS, sugar, hydroxypropyl-β-cyclodextrin (HP-β-CD) and (SBE)$_{7m}$-β-CD from various osmotic pump formulations. The first formulation contained a physical mixture of TS (○) and a mixture of sugar (●, lactose and fructose, 1/1); the second formulation contained TS (□) and (SBE)$_{7m}$-β-CD (■); and the third formulation contained TS (◇) and HP-P-CD (◆).

The results indicate that the osmotic pump containing (SBE)$_{7m}$-β-CD released a greater amount of TS and at a more acceptable rate than the osmotic pumps containing the sugar mixture or HP-β-CD.

The advantageous properties of the present formulation permit one to prepare drug delivery devices having a combined and controlled diffusional and osmotic delivery of drug. These devices are prepared by varying the amount of pore forming agent or the ratio of hydrophilic polymer to hydrophobic polymer in the semipermeable membrane and/or by varying the thickness of the semipermeable membrane in the device. In a preferred embodiment, the film thickness will be sufficient to reduce the rate of drug release by diffusion with respect to the rate of drug release by osmosis such that a therapeutic agent/SAE-CD inclusion complex formed in the core of the device will be delivered predominantly by osmosis.

In another preferred embodiment, a therapeutic agent will be delivered to a major degree by diffusion across a membrane and to a minor degree by osmosis through a passageway in the membrane. This type of combined and controlled delivery device is prepared by decreasing membrane thickness and increasing the porosity of the membrane, i.e. increasing the amount of pore forming agent relative to the amount of film forming agent.

In yet another preferred embodiment, a therapeutic agent will be delivered to a major degree by osmosis through a passageway in a membrane and to a minor degree by diffusion across the membrane. This type of combined and controlled delivery is prepared by increasing membrane thickness, reducing membrane porosity, i.e. by reducing the amount of or eliminating the pore forming agent in the membrane, and/or increasing the diameter of the passageway through the pore.

The layers, membranes or coats in the various embodiments of the present pharmaceutical compositions and formulations are generally applied as films or via compression. A film is generally formed by applying a solution, suspension or emulsion to an existing core or solid and removing the liquid portion to form a substantially dry film. A compression coating is generally made by compressing a second pharmaceutical composition onto a first pharmaceutical composition.

The term "pore forming agent" as used herein describes an agent that aids in the formation of pores in the film coating of the invention or improves the water permeability of the film. Such pore forming agents include, for example, carbohydrates such as lactose, dextrose, fructose, sucrose, mannose; a-hydroxy acids such as citric acid, tartaric acid, fumaric acid, succinic acid, glycolic acid, lactic acid, combinations thereof and their salts; halide counterions such as bromide, fluoride, iodide and chloride; divalent metal cations such as magnesium and calcium; anionic agents such as phosphates, sulfates, sulfonates, nitrates, bicarbonates, combinations thereof and their salts; cellulosics such as HPC, HPMC, hydroxyethylcellulose, methylcellulose; poly(ethylene oxide); poly(vinyl pyrrolidone); gums and gelling agents such as guar, xanthan gum, alginic acid, acacia, tragacanth, combinations thereof and their salts; clays such as montmorillonite clay, bentonite, Veegum, kaolin clay; miscellaneous ones such as kieselguhr, magnesium silicate, bentone, hectorite, PLURONICS™, hydrophilic surfactants; polyols such as sorbitol, mannitol, xylitol; proteins such as albumin, collagen, gelatin; water soluble amino acids; disintegrants such as starch, sodium starch glycolate, croscarmellose; and water soluble organic compounds; and combinations thereof. Pore forming agents which are water permeable will generally improve the permeability of the film.

The formulations of the invention are intended to form an SAE-CD complex when exposed to bodily fluids. In particular embodiments, the dosage forms of the invention will permit hydration of the SAE-CD/therapeutic agent physical mixture prior to release of the therapeutic agent to aid complex formation.

Method of Modifying Bioavailability and Rate of Bioabsorption

For poorly water soluble, hydrophobic drugs with poor bioavailability, the present invention advantageously provides a method of enhancing water solubility and modifying bioavailability and/or rate of bioabsorption in a patient. For water soluble, hydrophilic drugs with extremely high bioavailability, the present invention provides a method of modifying the rate of bioabsorption in a patient.

By the terms "poorly water soluble" and "hydrophobic" is meant a therapeutic agent having a solubility in neutral water less than about 1 mg/ml at 20° C. By "water soluble" and "hydrophilic" is meant a therapeutic agent having a solubility in neutral water greater than about 1 mg/mL at 20° C.

In some embodiments, the method of the present invention for modifying the bioavailability or rate of absorption of a therapeutic agent comprises the steps of providing a combination of a therapeutic agent and a sulfoalkyl ether cyclodextrin derivative, and administering the combination to a patient. By "modifying the bioavailability and/or rate of bioabsorption" is meant that the bioavailability and/or rate of bioabsorption of the therapeutic agent when administered in the combination with the SAE-CD will be different than (or modified with respect to) its bioavailability and/or rate of bioabsorption when administered alone.

In other embodiments, the present method comprises the steps of formulating together both the sulfoalkyl ether cyclodextrin derivative and the uncomplexed therapeutic agent, in a single pharmaceutically acceptable dosage form and administering the dosage form to a patient.

Without being held to the mechanism, it is believed the SAE-CD modifies the bioavailability and/or rate of absorption of the therapeutic agent by forming a clathrate or inclusion complex with it after being exposed to body fluids in a patient. The therapeutic agent/SAE-CD combination can be formulated in a variety of ways as described in detail below. It is only necessary that the SAE-CD be present in an amount sufficient to permit complexation with the therapeutic agent in a patient receiving the formulation.

General

The therapeutic agent which included in the present invention can possess a wide range of values for water solubility, bioavailability and hydrophilicity. Thus, the present invention contemplates any therapeutic agent which will form a clathrate or inclusion complex with a SAE-CD derivative of the formula a). Therapeutic agents to which the present invention is particularly suitable include poorly water soluble, hydrophobic therapeutic agents and water soluble, hydrophilic therapeutic agents. The formulations of the present invention are generally available in unit doses comprising less than about 500 mg, particularly less than about 150 mg, and more particularly less than about 50 mg of therapeutic agent. It will be understood by the artisan of ordinary skill that a therapeutic agent used in the formulations of the present invention is independently selected at each occurrence from any of the therapeutic agents disclosed herein.

The amount of therapeutic compound incorporated into the present formulations are selected according to known principles of pharmacy, clinical medicine and pharmacology. A therapeutically effective amount of therapeutic compound is specifically contemplated. By the term "therapeutically effective amount," it is understood that, with respect to, for example, pharmaceuticals, a pharmaceutically effective amount is contemplated. A pharmaceutically effective amount is the amount or quantity of a drug or pharmaceutically active substance which is sufficient to elicit the required or desired therapeutic response, or in other words, the amount which is sufficient to elicit an appreciable biological response when administered to a patient. As used with reference to a vitamin or mineral, the term "effective amount" means an amount at least about 10% of the United States Recommended Daily Allowance ("RDA") of that particular ingredient for a patient. For example, if an intended ingredient is vitamin C, then an effective amount of vitamin C would include an amount of vitamin C sufficient to provide 10% or more of the RDA. Typically, where the tablet includes a mineral or vitamin, it will incorporate higher amounts, preferably about 100% or more of the applicable RDA. The therapeutic compound is generally used in finely divided form, i.e. powder or granulate so as to increase the dissolution rate. It is preferable to use a finely powdered therapeutic compound to increase the dissolution rate, more preferably, the therapeutic compound being capable of allowing not less than 80%, desirably not less than 90%, of it to pass through a 100 mesh (150 microns) screen. The amount of therapeutic compound to be incorporated ranges usually from about 0.1 to 50%, preferably about 1 to 25% by weight based on the composition, and the ratio may be suitably modified depending on the therapeutic compound employed.

Examplary therapeutic agents include synthetic antibacterial agents of hardly water-soluble pyridone-carboxylic acid type such as benofloxacin, nalidixic acid, enoxacin, ofloxacin, amifloxacin, flumequine, tosfloxacin, piromidic acid, pipemidic acid, miloxacin, oxolinic acid, cinoxacin, norfloxacin, ciprofloxacin, pefloxacin, lomefloxacin, enrofloxacin, danofloxacin, binfloxacin, sarafloxacin, ibafloxacin, difloxacin and salts thereof. Other therapeutic agents include penicillin, tetracycline, cephalosporins and other antibiotics, antibacterial substances, antihistamines and decongestants, anti-inflammatories, antiparasitics, antivirals, local anesthetics, antifungal, amoebicidal, or trichomonocidal agents, analgesics, antiarthritics, antiasthmatics, anticoagulants, anticonvulsants, antidepressants, antidiabetics, antineoplastics, antipsychotics, antihypertensives and muscle relaxants. Representative antibacterial substances are beta-lactam antibiotics, tetracyclines, chloramphenicol, neomycin, gramicidin, bacitracin, sulfonamides, nitrofurazone, nalidixic acid and analogs and the antimicrobial combination of fludalanine/pentizidone. Representative antihistamines and decongestants are perilamine, chlorpheniramine, tetrahydrozoline and antazoline.

Representative anti-inflammatory drugs are cortisone, hydrocortisone, betamethasone, dexamethasone, fluocortolone, prednisolone, triamcinolone, indomethacin, sulindac and its salts and corresponding sulfide. A representative antiparasitic compound is ivermectin.

Representative antiviral compounds are acyclovir and interferon. Representative analgesic drugs are diflunisal, aspirin or acetaminophen. Representative antiarthritics are phenylbutazone, indomethacin, silindac, its salts and corresponding sulfide, dexamethasone, ibuprofen, allopurinol, oxyphenbutazone or probenecid. Representative antiasthma drugs are theophylline, ephedrine, beclomethasone dipropionate and epinephrine. Representative anticoagulants are bishydroxycoumarin, and warfarin. Representative anticonvulsants are diphenylhydantoin and diazepam. Representative antidepressants are amitriptyline, chlordiazepoxide perphenazine, protriptyline, imipramine and doxepin. Representative antidiabetics are insulin, somatostatin and its analogs, tolbutamide, tolazamide, acetohexamide and chlorpropamide. Representative antineoplastics are adriamycin, fluorouracil, methotrexate and asparaginase. Representative antipsychotics are prochlorperazine, thioridazine, molindone, fluphenazine, trifluoperazine, perphenazine, armitriptyline and trifluopromazine. Representative antihypertensives are spironolactone, methyldopa, hydralazine, clonidine, chlorothiazide, deserpidine, timolol, propranolol, metoprolol, prazosin hydrochloride and reserpine. Representative muscle relaxants are succinylcholine-chloride, danbrolene, cyclobenzaprine, methocarbamol and diazepam.

Some other examples of therapeutic agents include, but are not limited to, adiphenine, allobarbital, aminobenzoic acid, amobarbital, ampicillin, anethole, aspirin, azopropazone, azulene barbituric acid, beclomethasone, beclomethasone dipropronate, bencyclane, benzaldehyde, benzocaine, benzodiazepines, benzothiazide, betamethasone, betamethasone 17-valerate, bromobenzoic acid, bromoisovalerylurea, butyl-p-aminobenzoate, chloralhydrate, chlorambucil, chloramphenicol, chlorobenzoic acid, chlorpromazine, cinnamic acid, clofibrate, coenzyme A, cortisone, cortisone acetate, cyclobarbital, cyclohexyl anthranilate, deoxycholic acid, dexamethasone, dexamethasone acetate, diazepam, digitoxin, digoxin, estradiol, flufenamic acid, fluocinolone acetonide, 5-fluorouracil, flurbiprofen, griseofulvin, guaiazulene, hydrocortisone, hydrocortisone acetate, ibuprofen, indican, indomethacin, iodine, ketoprofen, lankacidin-group antibiotics, mefenamic acid, menadione, mephobarbital, metharbital, methicillin, metronidazole, mitomycin, nitrazepam, nitroglycerin, nitrosureas, paramethasone, penicillin, pentobarbital, phenobarbital, phenobarbitone, phenyl-butyric acid, phenyl-valeric acid, phenytoin, prednisolone, prednisolone acetate, progesterone, propylparaben, proscillaridin, prostaglandin A series, prostaglandin B series, prostaglandin E series, prostaglandin F series, quinolone antimicrobials, reserpine, spironolactone, sulfacetamide sodium, sulfonamide, testosterone, thalidomide, thiamine dilaurylsulphate, thiamphenicolpalmitate, thiopental, triamcinolone, VIAGRA™, vitamin A, vitamin D3, vitamin E, vitamin K3, and warfarin.

The therapeutic compound(s) contained within the pharmaceutical formulation are formulated as its pharmaceutically acceptable salts when necessary. As used herein, "pharmaceutically acceptable salts" refer to derivatives of the disclosed compounds wherein the therapeutic compound is modified by making acid or base salts thereof. Examples of pharmaceutically acceptable salts include, but are not limited to, mineral or organic acid salts of basic residues such as amines; alkali or organic salts of acidic residues such as carboxylic acids; and the like. The pharmaceutically acceptable salts include the conventional non-toxic salts or the quaternary ammonium salts of the parent compound formed, for example, from non-toxic inorganic or organic acids. For example, such conventional non-toxic salts include those derived from inorganic acids such as hydrochloric, hydrobromic, sulfuric, sulfonic, sulfamic, phosphoric, nitric and the like; and the salts prepared from organic acids such as amino acids, acetic, propionic, succinic, glycolic, stearic, lactic, malic, tartaric, citric, ascorbic, pamoic, maleic, hydroxymaleic, phenylacetic, glutamic, benzoic, salicylic, sulfanilic, 2-acetoxybenzoic, fumaric, toluenesulfonic, methanesulfonic, ethane disulfonic, oxalic, isethionic, and the like.

The pharmaceutically acceptable salts of the present invention are synthesized from the parent therapeutic compound which contains a basic or acidic moiety by conventional chemical methods. Generally, such salts are prepared-for example, by reacting the free acid or base forms of these compounds with a predetermined amount of the appropriate base or acid in water or in an organic solvent, or in a mixture of the two. Generally, nonaqueous media are preferred. Lists of suitable salts are found in Remington's Pharmaceutical Sciences, 18th ed., Mack Publishing Company, Easton, Pa., 1990, chp. 40, the disclosure of which is hereby incorporated by reference.

The phrase "pharmaceutically acceptable" is employed herein to refer to those compounds, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

As used herein, the term "active ingredient" can also be defined as a flavoring agent, a sweetening agent, a vitamin, a mineral and other such compounds for pharmaceutical applications. The present formulation can also contain adjuvants such as coloring agents, disintegrants, lubricants, bioadhesives and others known to those of ordinary skill in the art.

Disintegrants include starches such as corn starch, potato starch, pregelatinized and modified starches thereof, cellulosic agents such as Ac-di-sol, montmorrilonite clays, cross-linked PVP, sweeteners, bentonite and VEEGUM™, microcrystalline cellulose, alginates, sodium starch glycolate, gums such as agar, guar, locust bean, karaya, pectin and tragacanth. In particular embodiments, a tablet of the invention will not dissolve too rapidly so as to permit hydration the SAE-CD/therapeutic agent physical mixture therein.

Protease inhibitors which can be included in the present formulations include, by way of example and without limitation, antipain, leupeptin, chymostatin, amistatin and puromycin.

Penetration enhancers which can be included in the present formulations include, by way of example and without limitation, calcium chelators such as EDTA, methylated β-cyclodextrin, and polycarboxylic acids; surfactants such as sodium lauryl sulfate, sodium dodecyl sulfate, carnitine, carnitine esters, and tween; bile salts such as sodium taurocholate; fatty acids such as oleic and linoleic acid; and non-surfactants such as AZONE™ and dialkyl sulfoxides.

Flavors incorporated in the composition may be chosen from synthetic flavor oils and flavoring aromatics and/or natural oils, extracts from plants, leaves, flowers, fruits and so forth and combinations thereof. These may include cinnamon oil, oil of wintergreen, peppermint oils, clove oil, bay oil, anise oil, eucalyptus, thyme oil, cedar leave oil, oil of nutmeg, oil of sage, oil of bitter almonds and cassia oil. Also useful as flavors are vanilla, citrus oil, including lemon, orange, grape, lime and grapefruit, and fruit essences, including apple, pear, peach, strawberry, raspberry, cherry, plum, pineapple, apricot and so forth. Flavors which have been found to be particularly useful include commercially available orange, grape, cherry and bubble gum flavors and mixtures thereof. The amount of flavoring may depend on a number of factors, including the organoleptic effect desired. Particularly preferred flavors are the grape and cherry flavors and citrus flavors such as orange.

Materials to be incorporated in the present formulation can be pretreated to form granules. This process is known as granulation. As commonly defined, "granulation" is any process of size enlargement whereby small particles are gathered together into larger, permanent aggregates to yield a free-flowing composition having a suitable consistency. Such granulated compositions may have consistency similar to that of dry sand. Granulation may be accomplished by agitation in mixing equipment or by compaction, extrusion or agglomeration.

As used in this disclosure, the term "vitamin" refers to trace organic substances that are required in the diet. For the purposes of the present invention, the term "vitamin(s)" include, without limitation, thiamin, riboflavin, nicotinic acid, pantothenic acid, pyridoxine, biotin, folic acid, vitamin B12, lipoic acid, ascorbic acid, vitamin A, vitamin D, vitamin E and vitamin K. Also included within the term "vitamin" are the coenzymes thereof. Coenzymes are specific chemical forms of vitamins. Coenzymes include thiamine pyrophosphates (TPP), flavin mononucleotide (FMM), flavin adenine dinucleotide (FAD), Nicotinamide adenine dinucleotide (NAD), Nicotinamide adenine dinucleotide phosphate (NADP), Coenzyme A (CoA), pyridoxal phosphate, biocytin, tetrahydrofolic acid, coenzyme B12, lipoyllysine, 11-cis-retinal, and 1,25-dihydroxycholecalciferol. The term "vitamin(s)" also includes choline, carnitine, and alpha, beta, and gamma carotenes.

As used in this disclosure, the term "mineral" refers to inorganic substances, metals, and the like required in the human diet. Thus, the term "mineral" as used herein includes, without limitation, calcium, iron, zinc, selenium, copper, iodine, magnesium, phosphorus, chromium and the like, and mixtures thereof.

The term "dietary supplement" as used herein means a substance which has an appreciable nutritional effect when administered in small amounts. Dietary supplements include, without limitation, such ingredients as bee pollen, bran, wheat germ, kelp, cod liver oil, ginseng, and fish oils, amino-acids, proteins and mixtures thereof. As will be appreciated, dietary supplements may incorporate vitamins and minerals.

A bioadhesive can also be included in the present formulation. A bioadhesive is defined as a material that adheres to a biological surface such as mucous membrane or skin tissue. A bioadhesive will adherently localize a dosage form onto mucous membrane. The preferred bioadhesive is fibrous or particulate, water swellable but water insoluble. The appropriate ratio of bioadhesive to other components will provide strong bioadhesion. Bioadhesive polymers used in this invention include, for example, hydrophilic and water-dispensable polymers, have free carboxylic groups and a relatively high base binding capacity. These polymers as well as hydrophilic cellulosics are polycarboxylated vinyl polymers and polyacrylic acid polymers. Some hydrophilic polysaccharide gums such as guar gum, locust bean gum, psyllium seed gum, and the like are also suitable for use in the formula. The ratio by weight of bioadhesive to active ingredient may be quite broad. In practice, the weight ratio of bioadhesive to active ingredient is generally about 1:10 to about 10:1.

The SAE-CD containing pharmaceutical formulation of the invention may require particular hydrophobic or hydrophilic binders in order to obtain suitable product. Suitable hydrophobic binders include cellulose acetate butyrate, cellulose acetate propionate, cellulose propionate high molecular weight (200,000), cellulose propionate medium molecular weight (75,000), cellulose propionate low molecular weight (25,000), cellulose acetate, cellulose nitrate, ethylcellulose, polyvinyl acetate, and the like. Suitable hydrophilic binders include polyvinylpyrrolidone, vinyl alcohol polymer, polyethylene oxide, water soluble or water swellable cellulose and starch derivatives and others known to those of ordinary skill in the art.

Examples of other binders which can be added to the formulation include, for example, acacia, tragacanth, gelatin, starch, cellulose materials such as methyl cellulose and sodium carboxymethyl cellulose, alginic acids and salts thereof, polyethylene glycol, guar gum, polysaccharide, sugars, invert sugars, poloxomers (PLURONIC™ F68, PLURONIC™ F127), collagen, albumin, gelatin, cellulosics in nonaqueous solvents, pregelatinized starch, starch paste and combinations of the above and the like. Other binders include, for example, polypropylene glycol, polyoxyethylene-polypropylene copolymer, polyethylene ester, polyethylene glycol, polyethylene sorbitan ester, polyethylene oxide or combinations thereof and others known to those of ordinary skill in the art.

The melting and/or softening point temperatures of these binders usually rise with increase of their molecular weights. Binders having a melting or softening point temperature greater than about 150° C. may require use of a plasticizer during preparation of a suitable dosage form such that the binder melting or softening point temperature will be lowered below 150° C. The binder is generally in the form of a powder, granules, flakes or heat-molten liquid.

As used herein, the term "release rate modifier" refers to a substance which will modify the rate of release of the therapeutic agent from the pharmaceutical formulation according to the invention. The release rate modifier will assist in providing a controlled release of the therapeutic agent and can cooperate with other components in the formulation to provide either a delayed, sustained, timed, pH dependent, targeted, or further controlled delivery of the therapeutic agent. It will be understood that some of the binders mentioned herein can also be considered release rate modifiers.

As used herein, the term "plasticizer" includes all compounds capable of plasticizing a binder used in the invention. The plasticizer should be able to lower the melting temperature or glass transition temperature (softening point temperature) of the binder. Plasticizers, such as low molecular weight PEG, generally broaden the average molecular weight of the binder thereby lowering its glass transition temperature or softening point. Plasticizers also generally reduce the viscosity of a polymer. It is possible the plasticizer will impart some particularly advantageous physical properties to the formulation of the invention.

Plasticizers useful in the invention can include, by way of example and without limitation, low molecular weight polymers, oligomers, copolymers, oils, small organic molecules, low molecular weight polyols having aliphatic hydroxyls, ester-type plasticizers, glycol ethers, poly (propylene glycol), multi-block polymers, single block polymers, low molecular weight poly(ethylene glycol), citrate esters, triacetin, propylene glycol phthalate esters, phosphate esters, sebacate esters, glycol derivatives, fatty acid esters, and glycerin.

Such plasticizers can also be ethylene glycol, 1,2-butylene glycol, 2,3-butylene glycol, styrene glycol, diethylene glycol, dipropylene glycol, triethylene glycol, tetraethylene glycol and other poly(ethylene glycol) compounds, monopropylene glycol monoisopropyl ether, propylene glycol monoethyl ether, ethylene glycol monoethyl ether, diethylene glycol monoethyl ether, sorbitol lactate, ethyl lactate, butyl lactate, ethyl glycolate, dibutylsebacate, dimethylsebacate, di-2-ethylhexylsebacate, tricresyl phosphate, triethyl phosphate, triphenyl phosphate, acetylated monoglycerides, mineral oil, castor oil, glyceryl triacetate, butyl stearate, glycerol monostearate, butoxyethyl stearate, stearyl alcohol, cyclohexyl ethyl phthalate, cyclohexyl methyl dibutylphthalate, diethyl phthalate, dibutyl phthalate, diisopropyl phthalate, dimethyl phthalate, dioctyl phthalate, acetyl tributyl citrate, triethyl citrate, acetyl triethyl citrate, tributyl citrate and allyl glycolate. All such plasticizers are commercially available from sources such as Aldrich or Sigma Chemical Co. or Morflex, Inc. It is contemplated and within the scope of the invention, that a combination of plasticizers may be used in the present formulation.

The present pharmaceutical formulations generally comprise a solid core comprising sulfoalkyl ether cyclodextrin of the formula I, as described above, a pharmaceutically acceptable carrier, and a therapeutically effective amount of a therapeutic agent, a major portion of which is not complexed with the sulfoalkyl ether cyclodextrin. The solid core will be surrounded by a film coating. These formulations can be included in solid dosage forms such as, by way of example and without limitation, chewable bar, capsule, fiber, film, gel, granule, chewing gum, implant, insert, pellet, powder, tablet, tape, troche, pill, stick, strip and wafer.

Intended routes of administration include oral, peroral, buccal, nasal, implant, rectal, vaginal, sublingual, otic and urethral. The present formulation is generally administered with pharmaceutically acceptable carriers or diluents, the proportion and nature of which are determined by the solubility and chemical properties of the therapeutic agent selected, the chosen dosage form, and standard pharmaceutical practice. Solid oral forms may contain conventional excipients, for instance: lactose, sucrose, magnesium stearate, resins and like materials, flavoring, coloring, buffering, preserving, or stabilizing, agents. These formulations can also contain hygroscopic agents which can draw water into a tablet core. Such hygroscopic agents can include: water soluble electrolytes, small organic compounds, osmotic adjusting agents to increase the osmotic pressure within a dosage form and attract water.

As used herein, the term "patient" is taken to mean warm blooded animals such as mammals, for example, cats, dogs, mice, guinea pigs, horses, bovine cows, sheep and humans.

The term "unit dosage form" is used herein to mean a single or multiple dose form containing a quantity of the active ingredient and the diluent or carrier, said quantity being such that one or more predetermined units are normally required for a single therapeutic administration. In the case of multiple dose forms, such as liquids or scored tablets, said predetermined unit will be one fraction such as a half or quarter of a scored tablet of the multiple dose form. It will be understood that the specific dose level for any patient will depend upon a variety of factors including the indication being treated, the therapeutic agent employed, the activity of the therapeutic agent, severity of the indication, patient health, age, sex, weight, diet, and pharmacologic response, the specific dosage form employed and other such factors.

A variety of components or compounds can be used to aid in the preparation of suitable dosage forms for the present invention. Such components or compounds include, without limitation, an acidifying agent, alkalinizing agent, adsorbent, antifungal preservative, antioxidant, buffering agent, colorant, encapsulating agent, flavorant, stiffening agent, suppository base, sweetening agent, tablet antiadherent, tablet binder, tablet and capsule diluent, tablet coating agent, tablet direct compression excipient, tablet disintegrant, tablet glidant, tablet lubricant, tablet/capsule opaquant and tablet polishing agent.

As used herein, the term "acidifying agent" is intended to mean a compound used to provide acidic medium for product stability. Such compounds include, by way of example and without limitation, acetic acid, citric acid, fumaric acid, hydrochloric acid, and nitric acid and the like.

As used herein, the term "alkalinizing agent" is intended to mean a compound used to provide alkaline medium for product stability. Such compounds include, by way of example and without limitation, ammonia solution, ammonium carbonate, diethanolamine, monoethanolamine, potassium hydroxide, sodium borate, sodium carbonate, sodium hydroxide, triethanolamine, and trolamine and the like.

As used herein, the term "adsorbent" is intended to mean an agent capable of holding other molecules onto its surface by physical or chemical (chemisorption) means. Such compounds include, by way of example and without limitation, powdered and activated charcoal and the like.

As used herein, the term "preservative" is intended to mean a compound used to prevent the growth of microorganisms. Such compounds include, by way of example and without limitation, benzalkonium chloride, benzethonium chloride, benzyl alcohol, cetylpyridinium chloride, chlorobutanol, phenol, phenylethyl alcohol, phenylmercuric nitrate and thimerosal and the like.

As used herein, the term "antioxidant" is intended to mean an agent which inhibits oxidation and thus is used to prevent the deterioration of preparations by the oxidative process. Such compounds include, by way of example and without limitation, ascorbic acid, ascorbyl palmitate, butylated hydroxyanisole, butylated hydroxytoluene, hypophophorous acid, monothioglycerol, propyl gallate, sodium ascorbate, sodium bisulfite, sodium formaldehyde sulfoxylate and sodium metabisulfite and the like.

As used herein, the term "buffering agent" is intended to mean a compound used to resist change in pH upon dilution or addition of acid or alkali. Such compounds include, by way of example and without limitation, potassium metaphosphate, potassium phosphate, monobasic sodium acetate and sodium citrate anhydrous and dihydrate and the like.

As used herein, the term "colorant" is intended to mean a compound used to impart color to solid (e.g., tablets and capsules) pharmaceutical preparations. Such compounds include, by way of example and without limitation, FD&C Red No. 3, FD&C Red No. 20, FD&C Yellow No. 6, FD&C Blue No. 2, D&C Green No. 5, FD&C Orange No. 5, D&C Red No. 8, caramel, and ferric oxide, red and the like. Coloring agents can also include titanium dioxide, natural coloring agents such as grape skin extract, beet red powder, betacarotene, annato, carmine, turmeric, paprika and the like.

As used herein, the term "encapsulating agent" is intended to mean a compound used to form thin shells for the purpose of enclosing a drug substance or drug formulation for ease of administration. Such compounds include, by way of example and without limitation, gelatin, nylon, biodegradable polyesters, D,L-poly(lactic acid), polylactide-co 10 glycolic acid, cellulose acetate phthalate and the like.

As used herein, the term "flavorant" is intended to mean a compound used to impart a pleasant flavor and often odor to a pharmaceutical preparation. In addition to the natural flavorants, many synthetic flavorants are also used. Such compounds include, by way of example and without limitation, anise oil, cinnamon oil, cocoa, menthol, orange oil, peppermint oil and vanillin and the like.

As used herein, the term "sweetening agent" is intended to mean a compound used to impart sweetness to a preparation. Such compounds include, by way of example and without limitation, aspartame, dextrose, glycerin, mannitol, saccharin sodium, sorbitol and sucrose and the like.

As used herein, the term "tablet anti-adherents" is intended to mean agents which prevent the sticking of table formulation ingredients to punches and dies in a tableting machine during production. Such compounds include, by way of example and without limitation, magnesium stearate, corn starch, silicone dioxide, talc and the like.

As used herein, the term "tablet binders" is intended to mean substances used to cause adhesion of powder particles in table granulations. Such compounds include, by way of example and without limitation, acacia, alginic acid, carboxymethylcellulose sodium, compressible sugar (e.g., NuTab), ethylcellulose, gelatin, liquid glucose, methylcellulose, povidone and pregelatinized starch and the like.

As used herein, the term "tablet and capsule diluent" is intended to mean inert substances used as fillers to create the desired bulk, flow properties, and compression characteristics in the preparation of tablets and capsules. Such compounds include, by way of example and without limitation, dibasic calcium phosphate, kaolin clay, fructose, sucrose, dextrose, lactose, mannitol, microcrystalline cellulose, powdered cellulose, precipitated calcium carbonate, sorbitol, calcium sulfate, starch and the like.

As used herein, the term "tablet coating agent" is intended to mean a compound used to coat a formed tablet for the purpose of protecting against drug decomposition by atmospheric oxygen or humidity, to provide a desired release pattern for the drug substance after administration, to mask the taste or odor of the drug substance, or for aesthetic purposes. The coating may be of various types, including sugar coating, film coating, or enteric coating. Sugar coating is water-based and results in a thickened covering around a formed tablet. Sugar-coated tablets generally dissolve at the higher pH values of the intestines. A film coat is a thin cover around a formed tablet or bead. Unless it is an enteric coat, the film coat will dissolve in the stomach. An enteric coated tablet or bead will pass through the stomach and break up in the intestines. Some coatings that are water-insoluble (e.g., ethylcellulose) may be used to coat tablets and beads to slow the release of drug as the tablet passes through the gastrointestinal tract. Such compounds for coatings include, by way of example and without limitation, liquid glucose and sucrose are examples of sugar coating agents; hydroxyethyl cellulose, hydroxypropyl cellulose, hydroxypropyl methylcellulose, methylcellulose (e.g., Methocel) and ethylcellulose (e.g., Ethocel) are examples of film coating; and cellulose acetate phthalate and shellac (35% in alcohol, "pharmaceutical glaze") are examples of enteric coating and the like.

As used herein, the term "tablet direct compression excipient" is intended to mean a compound used in direct compression tablet formulations. Such compounds include, by way of example and without limitation, dibasic calcium phosphate (e.g., Ditab), phosphor spray dried, or anhydrous lactose, microcrystalline cellulose, (AVICEL™), dextran (EMDEX™), sucrose (NUTAB™) and others know to those of ordinary skill in the art.

As used herein, the term "tablet glidant" is intended to mean agents used in tablet and capsule formulations to reduce friction during tablet compression. Such compounds include, by way of example and without limitation, colloidal or fumed silica, magnesium stearate, cornstarch, and talc and the like.

As used herein, the term "tablet lubricant" is intended to mean substances used in tablet formulations to reduce friction during tablet compression. Such compounds include, by way of example and without limitation, calcium stearate, magnesium stearate, mineral oil, stearic acid, hydrogenated vegetable oil, benzoic acid, poly(ethylene glycol), NaCl, PRUV™, zinc stearate and the like.

As used herein, the term "tablet/capsule opaquant" is intended to mean a compound used to render a capsule or a tablet coating opaque. May be used alone or in combination with a colorant. Such compounds include, by way of example and without limitation, titanium dioxide and the like.

As used herein, the term "tablet polishing agent" is intended to mean a compound used to impart an attractive sheen to coated tablets. Such compounds include, by way of example and without limitation, carnauba wax, and white wax and the like.

The present formulation including therapeutic agent/SAE-CD physical mixtures have been found to be particularly suitable for therapeutic agents including simvastatin, cryptophycin, jaspamide, ambrosin, busulfan, propanolol, etoposide, taxol, brefeldin A, Brefeldin A prodrug (NSC#D656202), 9-Amino-20(S)-camptothecin, camptothecin, prednisolone acetate, prednisolone, pancreastatin, rhizoxin, bryostatin 1, taxotere $O_6$-benzylguanine, androstane, guanine, chloramphenicol, dapsone, sulfacone benclomethasone dipropionate, menadione, tamoxifen citrate, cholesterol, estrone, verapami 1 HCl, equilin, warfarin, indomethacin, phenytoin, cinnarizine, amiodarone HCl, naproxen, piroxicam, thiabendazole, papaverine, miconazole (free base), nifedipine, testosterone, progesterone, carbamazepine, methylprednisolone, dexamethasone, hydrocortisone and miconazole nitrate.

The foregoing will be better understood with reference to the following examples which detail certain procedures for the preparation of formulations according to the present invention. All references made to these examples are for the purposes of illustration. They are not to be considered limiting as to the scope and nature of the present invention.

EXAMPLE 1

Testosterone-(SBE)$_7$-β-CD

Sustained Release Formulation

The present example demonstrates the utility of the present invention for the preparation of sustained release formulations with pharmacologically active agent, testosterone providing an example of one such agent.

Phase Solubility Studies

Excess amounts of testosterone were added to 0.25 ml of (SBE)$_7$-βCD solutions ranging from 0.0 to 0.05 mol/l. The dispersions were allowed to equilibrate for a minimum of 24 hours in a shaking water bath (100 spm, 25° C.). The dispersions were centrifuged 10 min. at 2500 rpm, 20 µl of the supernatant were sampled with a gas-tight 100 µl syringe (Hamilton Co., NV), diluted with mobile phase and analyzed by HPLC for the testosterone concentration in solution. The testosterone-(SBE)$_7$-βCD binding constant $K_{1:1}$ was then determined by the method of Higuchi and Connors for an Type $A_L$ diagram.

Tablet Core Preparation

The tablet core was prepared with a 1/1 molar ratio of testosterone/(SBE)$_7$-β-CD. The tablet core consisted of either the testosterone-(SBE)$_7$-β-CD complex or the physical mixture of the two compounds. The complex was prepared by freeze-drying a testosterone-(SBE)$_7$-β-CD solution (5–15% in (SBE)$_{7m}$-β-CD). Non (SBE)$_7$-β-CD containing tablets were also prepared. They consisted of a 1/1 ratio of testosterone to a 50:50 (w/w) mixture of fructose and lactose (Fischer Scientific, NJ). The mixtures were ground in a mortar and sieved through a 200 mesh (75 µm) screen under low humidity conditions. The mixtures were stored in a desiccator when not used. Tablets of around 120 mg were compressed into the tablet die using a Carver Laboratory Press (Fred S. Carver Inc., NJ) at 1 ton during 1 min.

Semi-permeable Membrane Preparation The coating formulation was prepared by dissolving 1.0% of sorbitol (Sigma, MO) in 3.7% of double distilled water and 0.4% of PEG 400 (Sigma, MO). 2.0% of cellulose acetate (CA-398-10, Eastman Chemical Co., TN) were suspended in the solution; 55.7.% of methylene chloride and 37.2% of methanol were added to the mixture. The dispersion was shaken and sonicated until complete dissolution of the solid components. The coating solution was air sprayed (Airbrush, Paasche) on a stainless steel surface under constant air flow (40° C.). They were then left at room temperature during 24 hours. The membranes were peeled off the surface, checked for cracks and flaws under a light microscope (X70) and their thickness was measured using a Micrometer (Ames, Mass.). The membranes were then secured on the dissolution die containing the tablet, with the face which was sprayed on the steel in contact with the tablet surface.

In vitro Release Studies

The release studies were realized by placing the dissolution die in a USP dissolution apparatus II (Vanderkamp 600, VanKel Industries Inc.) containing 900 ml of water at 37° C., 100 rpm. Samples were collected at various time points. The 100% release was determined by removing the membrane from the die and allowing the drug dissolution to be complete. The samples were analyzed by HPLC for testosterone concentration.

Testosterone HPLC Detection

Testosterone was detected using a 15 cm ODS Hypersil column followed by UV detection at 238 mm (Shimadzu scientific Instruments, Inc., Japan). The mobile phase was composed of 60% acetonitrile and 40% double distilled water.

EXAMPLE 2

Dipyridamole-(SBE)$_7$-β-CD

Delayed Release Formulation

Analytical Procedures

Dipyridamole was analyzed using a 15 cm ODS Hypersil column. The sample volume was 20 µl and the UV detection wavelength was 285 mm (Shimadzu 6A, Shimadzu, Japan). A mobile phase consisting of 70% methanol and 30% ammonium phosphate buffer (pH 5.0) was passed through the column at a flow rate of 1.5 ml/min. $(SBE)_{7m}$-β-CD was detected by using a fluorimetric assay, 0.2 ml of a 1 mM solution of 2,6-toluidino-naphthalene-sulfonate to 0.8 ml of the sample. This solution was then excited at 325 nm and the emitted fluorescence detected at 455 nm using a Perkin Elmer (Perkin-Elmer, CT) Fluorescence detector.

Phase Solubility Experiments $(SBE)_7$-β-CD (0–0.1 M) solutions were made in different buffer solutions at pH values ranging from 4.0 to 7.0 (citrate for 4 & 5; phosphate for 6 & 7). Excess of dipyridamole was added to 0.25 ml of these solutions and were allowed to equilibrate for a minimum of 24 hours in a shaking water bath at 25° C. (Preliminary experiments indicated that the equilibrium solubility was attained within 24 hr.). The solutions were centrifuged for 10 min. at 2500 rpm. 20 µl of the supernatant was carefully sampled using a 100 µl gas-tight Hamilton Syringe (Hamilton, Nev.), diluted with mobile phase and analyzed by HPLC. The solubility data was then used to determine the binding constant using the method of Higuchi and Connors for AL-type phase behavior.

Physical Mixture Preparation:

Dipyridamole (SIGMA, MO), $(SBE)_7$-β-CD and citric acid (SIGMA, MO) (1:9:3 molar ratio) were physically mixed and ground manually using a mortar and pestle. The ground physical mixture was then sieved through a 200 mesh (75 µm) screen. This process was repeated twice. This mixture was always stored in a desiccator when not used.

Dissolution Die Description and Tablet Preparation:

The dissolution die consists of a cylindrical stainless steel center-piece, a stainless steel platform, a stainless steel top cover, two Teflon sheets (top and bottom) and Teflon inserts. The cylindrical center-piece has a hole (radius=7.5 mm) at the center in which the tablet is compressed. Both, the stainless steel top cover and top Teflon sheet have holes of same radius at the center. The center-piece was inverted and screwed onto the platform. Approximately, 120 mg of physical mixture containing drug, (SBE)7-β CD and citric acid was poured into the cylindrical hole and a punch was firmly placed in it. The tablet core was compressed with a force of one ton for one minute using Carver press (Fred Carver Inc., NJ). The punch was carefully removed from the center-piece.

Film Coatings
Polymeric Solutions Preparation

EUDRAGIT™ coatings were made by dissolving 5% (w/w) of EUDRAGIT™ R or S (Huls America, NJ), 5% of urea (SIGMA, MO) or polyethylene glycol (PEG 3350, SIGMA, MO) and 0.75% of triethyl Citrate (TEC, SIGMA, MO) in 89.25% ethanol. This was carried out until a clear solution was obtained. Cellulose acetate (CA-320S7 Eastman Chemical Co., TN) and hydroxypropyl methylcellulose phthalate (HPMCP, Eastman Chemical Co., TN) polymeric solutions were made by dissolving 5% of polymers and 1% of TEC in 94% of solvent containing equal amounts of methylene chloride and methanol. The ratio of CA to HPMCP was varied from 50:50 to 75:25 but the total amount of polymer was always maintained at 5%. The dissolution was carried out until clear solutions were obtained.

Tablet Coating

This coating solution was then air sprayed directly on the tablet surface under constant air flow (approx. 70° C.). The coated tablets were dried additionally for a period of 15 minutes under the same air flow. The tablets were additionally dried for a period of 12–16 hr. at room temperature. The thickness of the membrane was assumed to be the difference of thickness of the tablet after and before coating. The thickness measurements were carried out using a Screw-gauge micrometer.

In vitro Release Studies

The release studies for tablets coated with Eudragit L and CA: HPMCP were conducted by placing the dissolution die in a USP dissolution apparatus II (Vanderkamp 600, VanKel Industries Inc.) containing 450 ml of HCl (pH 1.5, 37° C. and 100 r.p.m.). After 2 hr., the die was carefully removed and placed in 450 ml phosphate buffer (pH 1.5, 37° C. and 100 r.p.m.) and the dissolution experiment was continued. 1.5 ml samples were collected periodically and equal amounts of dissolution medium was returned to the dissolution vessel. For the CA: HPMCP coated tablet, 100% release was determined by removing the membrane from the die and allowing the drug dissolution to be complete. The release experiments for tablets coated with Eudragit were conducted similarly in 450 ml of HCl for the first 2 hours, then placed in a phosphate buffer (pH 6.4) for additional 5 hr. and then placed in a phosphate buffer (pH 7.2). The release conditions and procedures were as described above.

0.5 ml of the sample was diluted by half in the mobile phase and the diluted samples were then analyzed using HPLC assay to determine drug concentrations as described in a later section. The rest of the sample was filtered through PVDF membrane (Fischer Scientific, NJ) and drug-free samples were then analyzed for $(SBE)_7$-β-CD by using the fluorimetric assay described below.

EXAMPLE 3

Methylprednisolone-$(SBE)_7$-β-CD

Sustained Release Formulation

Phase Solubility Studies

Excess amounts of methylprednisolone (MP) were added to 0.25 ml of $(SBE)_7$-β-CD solutions ranging from 0.0 to 0.2 mol/l. The dispersions were allowed to equilibrate for a minimum of 24 hours in a shaking water bath (100 rpm, 25° C.). The dispersions were centrifuged 10 min. at 2500 rpm, 20 µl of the supernatant were sampled with a gas-tight 100 µl syringe (Hamilton Co., Nev.), diluted with mobile phase and analyzed by HPLC for the methylprednisolone concentration in solution. The methylprednisolone-$(SBE)_7$-β-CD binding constant $K_{1:1}$ was then determined by the method of Higuchi and Connors for an Type $A_L$ diagram.

Tablet Core Preparation

The tablet core was prepared with a 1/7 molar ratio of methylprednisolone/$(SBE)_7$-β-CD. This ratio was calculated using the previously determined binding constant in order to have sufficient $(SBE)_7$-β-CD in the tablet core to solubilize all the methylprednisolone present. Tablet cores with 1/3 and 1/10 ratios were also prepared to study the influence of the methylprednisolone/(SBE)7-β-CD ratio on the release (cf. results 4). The tablet core consisted of either the methylprednisolone-(SBE)7-β-CD complex or the physical mixture of the two compounds. The complex was prepared by freeze drying a methylprednisolone-$(SBE)_7$-β-CD solution (5–15% in (SBE)7-β-CD). Non $(SBE)_7$-β-CD containing tablets were also prepared. They consisted of a 1/7 ratio of methylprednisolone to a 50:50 (w/w) mixture of fructose and lactose (Fischer Scientific, N.J.). The mixtures were ground in a mortar and sieved through a 200 mesh (75 µm) screen under low humidity conditions. The mixtures were stored in a dessicator when not used. Tablets of around 150 mg were compressed into the dissolution die using a Carver Laboratory Press (Fred S. Carver Inc., N.J.) at 1 ton during 1 min.

Semi-permeable Membrane Preparation

The coating formulation was prepared by mixing 4.5% of ethylcellulose (Ethocel Standard 10 Premium, Dow Chemicals, Mich.) with an equivalent amount of poly (ethylene glycol) 3350 (PEG 3350, Sigma, MO). 0.9% of PEG 400 (Sigma, MO) and 90.1% of absolute ethanol were added to the mixture. The dispersion was shaken and sonicated until complete dissolution of the solid components. The coating solution was air sprayed (Airbrush, Paasche) on a Teflon surface under constant air flow (40° C.). At the end of the spraying, the membranes were dried under the 40° C. air flow for 5 min. They were then left at room temperature during 24 hours. The membranes were peeled off the Teflon surface, checked for cracks and flaws under a light microscope (X70) and their thickness was measured using a micrometer (Ames, Mass.). The membranes were then secured on the dissolution die containing the tablet, with the face which was sprayed on the Teflon in contact with the tablet surface.

In vitro Release Studies

The release studies were realized by placing the dissolution die in a USP dissolution apparatus II (Vanderkamp 600, VanKel Industries Inc.) containing 350 ml of water at 37° C., 100 rpm. Samples were collected at various time points. The 100% release was determined by removing the membrane from the die and allowing the drug dissolution to be complete. The samples were analyzed by HPLC and fluorimetric assays for methylprednisolone and $(SBE)_7$-$\beta$-CD concentrations respectively.

Methylnrednisolone HPLC Detection

Methylprednisolone was detected using a 15 cm ODS Hypersil column followed by UV detection at 254 nm (LC-10AT, Shimadzu scientific Instruments, Inc., Japan). The mobile phase was composed of 30% acetonitrile and 70% of pH 4.7 acetate buffer.

$(SBE)_7$-$\beta$-CD fluorimetric detection $(SBE)_7$-$\beta$-CD was detected by adding 0.2 ml of a 1E-3 mol/l solution of 2,6-10 toluidinonaphthalene-sulfonate to 0.8 ml of the sample. The solution was excited at 325 nm and the emitted fluorescence detected at 455 nm (65040 Fluorescence Spectrophotometer, Perkin-Elmer, Conn.).

EXAMPLE 4

Tablet Comprising $SBE_7$-$\beta$-CD and a Therapeutic Agent

Tablet dosage forms according to the invention can generally be prepared as follows. A therapeutic agent and $SBE_7$-$\beta$-CD are dry blended for about 10 min. The remaining ingredients are added and the mixture is dry blended for about 10 min. The tablets are then compressed to a hardness of about 8–10 Kg. The following exemplary formulations are used to prepare the dosage forms of the invention.

| Indomethacin formulation | |
|---|---|
| Ingredient | Amount (mg) |
| 1:indomethacin | 25 |
| 1:$SBE_7$-$\beta$CD | 300 |
| 2:EMDEX ™ | 160 |
| 2:polyox-0.4 M (poly(ethylene oxide)) | 20 |
| 2:sucrose | 55 |
| 3:PRUV ™ (Sodium stearyl fumarate) | 12 |
| 3:magnesium stearate | 3 |

| -continued | |
|---|---|
| Indomethacin formulation | |
| Ingredient | Amount (mg) |
| 3:corn starch | 25 |
| Total | 600 |

The above ingredients are used to make a 600 mg tablet core having a rapid release profile. The numbers beside the ingredients indicates the general order of addition. After each group of ingredients is added, the mixture is dry blended for 5–10 min. The PRUV™, magnesium stearate and cornstarch are added in separately (step 3) from other ingredients and an additional 5 min. dry blend step is added to the general procedure.

| Dipyridamole formulation | |
|---|---|
| Ingredient | Amount (mg) |
| dipyridamole | 25 |
| 1:$SBE_7$-$\beta$CD | 300 |
| 2:citric acid | 53 |
| 2:PEG 3350 | 25 |
| 2:dextrose | 125 |
| 2:Cabosil M5P | 2 |
| 3:PRUV ™ | 10 |
| 3:magnesium stearate | 5 |
| 3:AC-Di-Sol ™ | 10 |
| Total | 555 |

The above ingredients are used to make a 555 mg tablet core having a rapid release profile. The numbers beside the ingredients indicates the general order of addition. After each group of ingredients is added, the mixture is dry blended for 5–10 min. The PRUV™, magnesium stearate, and Ac-Di-Sol™ are added in separately (step 3) from other ingredients and an additional 5 min. dry blend step is added to the general procedure.

| Piroxicam formulation | |
|---|---|
| Ingredient | Amount (mg) |
| 1:Piroxicam | 10 |
| 1:$SBE_4$-$\beta$CD | 77 |
| 2:sorbitol | 45 |
| 2:dextrose | 50 |
| 2:citric acid | 10 |
| 2:xylitol | 47.5 |
| 2:PEG 3350 | 9 |
| 3:magnesium stearate | 15 |
| 3:fumed silicon dioxide | 1.5 |
| 3:croscarmellose sodium | 5.5 |
| Total | 257 |

The above ingredients are used to make a 500 mg tablet core having a rapid release profile. The numbers beside the ingredients indicates the general order of addition. After each group of ingredients is added, the mixture is dry blended for 5–10 min. The magnesium stearate, fumed silicon dioxide (CABOSIL™ M5P) and croscarmellose sodium are added in separately (step 3) from other ingredients and an additional 5 min. dry blend step is added to the general procedure.

| Diltiazem formulation | |
|---|---|
| Ingredient | Amount (mg) |
| 1:diltiazem | 10 |
| 1:SBE$_7$-βCD | 270 |
| 2:citric acid | 19 |
| 2:PEG 6000 | 5 |
| 2:dextrose | 246 |
| 2:sorbitol | 40 |
| 3:PRUV ™ | 5 |
| 3:CABOSIL ™ M5P | 3 |
| 3:sodium starch glycolate | 2 |
| Total | 600 |

The above ingredients are used to make a 600 mg tablet having a rapid release profile. The numbers beside the ingredients indicates the general order of addition. After each group of ingredients is added, the mixture is dry blended for 5–10 min. The PRUV™, CABOSILT ™ M5P and sodium starch glycolate are added in separately (step 3) from other ingredients and an additional 5 min. dry blend step is added to the general procedure.

| Warfarin formulation | |
|---|---|
| Ingredient | Amount (mg) |
| 1:warfarin | 2 |
| 1:SBE$_7$-βCD | 150 |
| 2:EMDEX ™ | 138.5 |
| 2:NaHCO$_3$ | 20 |
| 2:sodium lauryl sulfate | 2.0 |
| 3:magnesium stearate | 2.5 |
| Total | 315 |

The above ingredients are used to make a 315 mg tablet core having a rapid release profile. The numbers beside the ingredients indicates the general order of addition. After each group of ingredients is added, the mixture is dry blended for 5–10 min. The magnesium stearate is added in separately (step 3) from other ingredients and an additional 5 min. dry blend step is added to the general procedure

| Methylprednisolone formulation:A | |
|---|---|
| Ingredient | Amount (mg) |
| 1:MP | 10 |
| 1:SBE$_4$-γCD | 200 |
| 2:xylitol | 151 |
| 2:pregelatinized starch | 150 |
| 2:sucrose | 33 |
| 3:CABOSIL ™ MSP | 4 |
| 3:PRUV ™ | 12 |
| Total | 560 |

The above ingredients are used to make a 560 mg tablet core having a rapid release profile. The numbers beside the ingredients indicates the general order of addition. After each group of ingredients is added, the mixture is dry blended for 5–10 min. The PRUV™ and CABOSIL™ M5P are added in separately (step 3) from other ingredients and an additional 5 min. dry blend step is added to the general procedure.

| Methyl Prednisolone Formulation:B | |
|---|---|
| Ingredient | Amount (mg) |
| MP | 4 |
| Spray-dried lactose monohydrate (SUPERTAB ™, FMC Corp.) | 96 |
| Microcrystalline cellulose (CEOLUS ™, FMC Corp.) | 32 |
| Sodium stearyl fumarate (PRUV ™, Mendell) | 2 |
| SBE$_7$-βCD (CAPTISOL ™, Cydex, Inc.) | 116 |
| Total | 250 |

The above formulation was prepared by first reducing the particle size of the SBE$_7$-βCD with a wedgewood mortar and pestle and then passing the powder through a 100 mesh screen. The sodium stearyl fumarate was also sieved through a 100 mesh screen prior to use. The SBE$_7$-βCD and MP were blended together geometrically in a glass mortar. The CEOLUS™, SUPERTAB™, PRUV™ components were then added in order in sequential steps while mixing. Tablets weighing approximately 250 mg each were compressed by hand on a Stokes B2 tablet press using 7 mm standard cup concave toolings. The tablets were compressed to a hardness of approximately 14 kp.

| Indomethacin minitablet-gelatin capsule formulation | |
|---|---|
| Ingredient | Amount (mg) |
| 1:indomethacin | 25 |
| 1:SBE$_7$-βCD | 300 |
| 2:EMDEX ™ | 155 |
| 2:polyox-0.4 M (poly(ethylene oxide)) | 20 |
| 2:sucrose | 55 |
| 3:PRUV ™ (Sodium stearyl fumarate) | 20 |
| 3:corn starch | 25 |
| Total | 600 |

The above ingredients are used to make a 600 mg hard gelatin capsule comprising 3×200 mg film coated mini-tablets according to the invention. The uncoated mini-tablet cores have rapid release profiles. The mini-tablets are made as follows. The numbers beside the ingredients indicates the general order of addition. After each group of ingredients is added, the mixture is dry blended for 5–10 min. The PRUV™ and cornstarch are added in separately (step 3) from other ingredients and an additional 5 min. dry blend step is added to the general procedure. The mixture is then divided into three equal parts and each part compressed into a mini-tablet. Following coating of the table core with a film forming agent of the invention according to the example below, the coated mini-tablets are placed within a hard gelatin capsule.

It should be noted that in several of the above examples, binders such as EMDEX™ and polyox-0.4 M are replaceable by release controlling agents, or release rate modifiers, such as HPMC, HPC, cellulose acetate butyrate, cellulose acetate propionate, cellulose propionate, carrageenan, cellulose acetate, cellulose nitrate, methylcellulose, hydroxyethyl cellulose, ethylcellulose, polyvinyl acetate, latex dispersions, acacia, tragacanth, guar gum, gelatin, and the like. Thus, uncoated tablet cores having a controlled or sustained release profile are prepared and optionally further coated with the film forming agents of the invention to provide a tablet formulation having a combination delayed and controlled or sustained release profile, i.e. upon reaching a predetermined part of the GI tract, the film of the tablet will become porous and permit the therapeutic agent to be released from the tablet core in a controlled or sustained release fashion. A sustained or controlled release tablet core will be suitable for tablet formulations comprising a very water soluble film forming agent, a very porous film, a large amount of osmotic or solubilizing agents and other such conditions.

Alternative methods for preparation of the tablet core include, for example, dry granulation, wet granulation, hot melt granulation, hot melt extrusion and compression-grinding-recompression. Accordingly, the dry granulation method can comprise preformation of a tablet or slugs with all tablet ingredients excluding the SAE-CD, grinding of the preformed tablet or slug, admixture of the ground material with an SAE-CD, and recompression of the mixture to form the desired tablet formulation.

| Indomethacin controlled or sustained release tablet core formulation | |
|---|---|
| Ingredient | Amount (mg) |
| 1:indomethacin | 25 |
| 1:SBE$_7$-βCD | 300 |
| 2:HPMC | 100 |
| 2:sucrose | 55 |
| 3:PRUV ™ (Sodium stearyl fumarate) | 20 |
| 3:corn starch | 25 |
| Total | 525 |

The above ingredients are used to make a 525 mg tablet core having a controlled or sustained release profile. The numbers beside the ingredients indicates the general order of addition. After each group of ingredients is added, the mixture is dry blended for 5–10 min. The PRUV™ and cornstarch are added in separately (step 3) from other ingredients and an additional 5 min. dry blend step is added to the general procedure.

| Prednisolone Controlled Release Tablet Core Formulation | |
|---|---|
| Ingredient | Amount (mg) |
| Prednisolone | 15 |
| SBE$_7$-βCD | 210 |
| HPMC K100M | 75 |
| Total | 300 |

The above ingredients are used to make a 300 mg tablet core having a controlled release profile. The ingredients were blended by hand and individual tablets were prepared on a carver press under a pressure of 1 ton for 7 seconds. The tablets were prepared using a 5/16″ standard cup concave tooling. The determination of the release profile by dissolution was conducted according to USP method 2 at 37°, 100 rpm with paddles in a 900 ml water bath. The amounts of prednisolone (PD) released was determined by HPLC, and the amount of SBE$_7$-βCD released was determined by TNS as described herein.

Additional controlled release tablet cores prepared according to the invention contain the below-described ingredients and corresponding amounts.

| Ingredient | Amount (mg) |
|---|---|
| Prednisolone | 5–30 |
| SBE$_7$-βCD | 50–210 |
| Lactose | 0–210 |
| HPMC K100M | 50–200 |

An uncoated core controlled release pharmaceutical formulation can comprise a therapeutic agent, an SAE-CD, a release rate modifier, and optionally one or more other pharmaceutical excipients.

EXAMPLE 5

Tablet Core Made from Granules Comprising

SBE$_7$-βCD and a Therapeutic Agent

Tablet dosage forms according to the invention can contain granules and be made by wet granulation generally as follows. The indicated percentages correspond to weight percentages based on the final formulation weight. This example is based upon a 10 mg dose of methylprednisolone (MP). The therapeutic agent (20%) and SBE$_7$-βCD are dry blended to form a physical mixture. Lactose (40%) and dextrose (8%) are wet granulated with PVP aqueous suspension (4%) until a 2% weight increase is obtained to form the desired granules. NaHCO$_3$ (3.5%), PRUV™ (4.5%), SiO$_2$ (0.5%) and xylitol (2%) are dry blended with the granules and the physical mixture, and the final mixture is compressed into tablets to a hardness of about 8–10 Kg.

EXAMPLE 6

Tablet Film Coatings

Tablet film coatings according to the invention are generally made using the following ingredients and conditions. The film coatings are generally aqueous, aqueous/solvent and/or solvent, e.g. alcohol, based. Generally, the film forming agent is dissolved or suspended in about ½ the volume of the projected solution volume, and the other ingredients are added. The mixture is then brought to final volume by further addition of water or solvent as desired. The resulting solution or suspension is used according to Example 7 to coat the tablet cores prepared as described above. The film compositions detailed below are based upon a 100 ml final solution or suspension volume.

| EUDRAGIT ™ RS 30D film formulation: | |
|---|---|
| Ingredient | Amount (g) |
| EUDRAGIT ™ RS 30D | 15 (dry weight) |
| triethyl citrate (TEC) | 3 |
| Talc | 7.5 |

The EUDRAGIT™ RS 30D is obtained as a 30% wt. aqueous latex dispersion from the manufacturer. EUDRAGIT™ RS 30D (film forming agent) is dispersed in water (50 ml) while stirring and the TEC, talc and HPMC (pore former) are subsequently added. The final solution volume is brought to 100 ml by the addition of more water. Other pore formers and film forming agents will generally be useful.

| EUDRAGIT ™ RL 100 film formulation: | |
| --- | --- |
| Ingredient | Amount (g) |
| EUDRAGIT ™ RL 100 | 15 (dry weight) |
| TEC | 3 |
| Talc | 7.5 |
| HPC | 1.5 |

The EUDRAGIT™ RL 100 are formulated in isopropanol (IPA). EUDRAGI™ RL 100 is dissolved in IPA (50 ml) while stirring and the TEC, talc and HPC are subsequently added. The final solution volume is brought to 100 ml by the addition of more IPA.

| EUDRAGIT ™ RS 30D/EUDRAGIT ™ RL 30D film formulation: | |
| --- | --- |
| Ingredient | Amount (g) |
| EUDRAGIT ™ RS 30D | 13.5 (dry weight) |
| EUDRAGIT ™ RL 30D | 1.5 (dry weight) |
| TEC | 3 |
| Talc | 7.5 |
| HPC | 1.5 |

The EUDRAGIT™ RL 30D and EUDRAGIT™ RS 30D are diluted in water while stirring and the TEC, talc and HPC are subsequently added. The final volume is adjusted as desired by the addition of more water. The EUDRAGIT™ RL 30D serves to improve the water permeability of the EUDRAGIT™ film.

| Ethylcellulose film formulation | |
| --- | --- |
| Ingredient | Amount (g) |
| ethylcellulose | 15 (dry weight) |
| dibutyl sebacate | 4.5 |
| talc | 8.0 |
| HPMC E5 | 1.5 |

The ethylcellulose is dissolved in isopropanol while stirring and the dibutyl sebacate, talc and HPMC E5 are subsequently added. The final volume is adjusted as desired by the addition of more isopropanol. This same procedure is conducted using HPC in place of the HPMC E5.

| Cellulose acetate film formulation: | |
| --- | --- |
| Ingredient | Amount (g) |
| cellulose acetate | 12 (dry weight) |
| TEC | 5 |
| talc | 7.5 |
| lactose | 1.5 |

The cellulose acetate is placed in isopropanol while stirring and the TEC, talc and lactose are subsequently added. The final volume is adjusted as desired by the addition of more solvent. When using this film formulation, it may be necessary to operate the Hi-Coater at 45° C. or higher.

| EUDRAGIT ™ RS 30D and EUDRAGIT ™ L 100 film formulation: | |
| --- | --- |
| Ingredient | Amount (g) |
| EUDRAGIT ™ RS 30D | 15 (dry weight) |
| micronized EUDRAGIT ™ L 100 | 1 (dry weight) |
| triethyl citrate (TEC) | 3 |
| Talc | 7.5 |

The TEC and talc are added to the EUDRAGIT™ RS 30D dispersion while stirring. The micronized EUDRAGIT™ L 100 powder is added with agitation and the dispersion volume is adjusted as desired to final volume by the addition of more water. Other film forming agents such as cellulose acetate and HPMCP will generally be useful in these combination film formulations.

| EUDRAGIT ™ L 100 film formulation | |
| --- | --- |
| Ingredient | Amount (g) |
| EUDRAGIT ™ L 100 | 15 (dry weight) |
| triethyl citrate (TEC) | 3 |
| Talc | 7.5 |

The EUDRAGIT™ L 100 is dissolved or suspended in isopropanol or water, respectively, while stirring and the TEC and talc are subsequently added. The final volume is adjusted as desired by the addition of more solvent or water. In some embodiments, this film will be used to provide an enteric release tablet formulation or used to coat tablets already coated with other film coatings of the invention. The resulting tablet formulation will provide a formulation having a delayed controlled or sustained release of a therapeutic agent from the tablet core.

| EUDRAGIT ™ RS30D and EUDRAGIT ™ RL30D Film Formulation: | |
| --- | --- |
| Ingredient | Amount (g) |
| EUDRAGIT ™ RS30D | 15.0 (dry weight) |
| EUDRAGIT ™ RL30D | 1.67 (dry weight) |
| Plasticizer (Triethyl citrate) | 2.8 |
| Antiadherent (glyceryl monostearate, Imwittor ™ 900) | 1.5 |
| Deionized water | q.s. |

The water, triethyl citrate and Imwittor™ 900 were combined in a beaker to form a dispersion which was homogenized using a Powergen™ blender until the temperature was less than 35° C. The dispersion was then sieved through a 60 mesh screen, recovered and stirred until the temperature was less than 30° C. The EUDRAGIT™ dispersions which included EUDRAGIT™ $RS_{30}D$ (30% by wt. aqueous dispersion) and EUDRAGIT™ RL30D (30% by wt. aqueous dispersion) were passed through a 60 mesh screen, then combined with the first dispersion and allowed to equilibrate for 30 minutes prior to spraying of the final dispersion onto the tablet cores. This particular formulation provided a semi-permeable membrane containing no pore forming agent.

EUDRAGIT ™ RS30D and EUDRAGIT ™
RL30D Film Formulation:

| Ingredient | Amount (% Wt) |
| --- | --- |
| EUDRAGIT ™ RS30D | 40 |
| EUDRAGIT ™ RL30D | 3 |
| Plasticizer (Triethyl citrate) | 2.5 |
| Talc | 6 |
| Deionized water | q.s. 100 |

This film formulation does not contain a pore former but nonetheless allows moisture to permeate into the tablet core. The dispersions are plasticized with the TEC for 1 hour before spraying onto tablet cores.

| AQUACOAT ™ Film Formulation | |
| --- | --- |
| Ingredient | Amount (% Wt) |
| AQUACOAT ™ ECD | 50 |
| Dibutyl sebacate (DBS) | 3 |
| Water | q.s. 100 |

These dispersions are plasticized with the DBS for at least 8 hours prior to spraying onto tablet cores.

Other ethylcellulose dispersions such as the SURELEASE™ products from Colorcon are also suitable film coatings for controlled release.

EXAMPLE 7

Coating of Tablet Core with Film Forming Agents

A film coated tablet formulation will generally be made generally as follows. Other equivalent conditions and equipment, as are known to the skilled artisan, will generally be useful in the preparation of the present formulations.

A Vector Hi-Coater (perforated pan tablet coater) is used under the following conditions:

| | |
| --- | --- |
| inlet temperature: | 45–75° C. |
| outlet temperature: | 28–38° C. |
| spray rate: | 2–3 g/min |
| tablet load: | 300 g |
| rotation speed: | 20 rpm. |

Following preparation of a solution or suspension containing the film forming agent and other ingredients (according to Example 6), tablet cores are placed inside the Hi-Coater and the film coat done until an about 100–125 µm thick film is formed. The coated tablets are dried at about 40° C. overnight. The tablet thickness and film composition are varied as desired. The present method is generally used on aqueous or solvent based film coating compositions.

EXAMPLE 8

Multilayered Tablets

Bilayered and multi-layered tablets containing the physical mix and the preformed complex of a drug and the $SBE_7$-$\beta$-CD in a retardant matrix formulation, are manufactured on a Stoke's D press or similar equipment.
Method A: Bi-layered Tablet.

An immediate release layer comprising a physical mixture of indomethacin and $SBE_7$-$\beta$-CD complex is prepared according to Example 4. Specifically, 240 mg of granulate containing 10 mg of the indomethacin is compressed in a Stoke's D press to form the immediate release layer.

A controlled release layer is made by mixing the following ingredients, wherein the indomethacin and the cyclodextrin are present as a physical mix:

| | |
| --- | --- |
| Indomethacin | 15 mg |
| $SBE_7$-$\beta$-CD | 180 mg |
| HPMC K15M | 80 mg |
| Spray Dried Lactose | 85 mg |
| MCC PH 101 | 48 mg |
| Magnesium stearate | 2 mg |

The indomethacin and $SBE_7$-$\beta$-CD are combined into a physical mixture and added to the HPMC, spray dried lactose, and MCC, and blended for 15 minutes in a Twin Shell blender. Magnesium stearate is then added to the powder and blended for an additional 5 minutes. This mixture is then compressed onto the immediate release layer. Tablets weighing 650 mg are compressed to approximately 10 kg hardness. The tablets can then be coated with a readily water soluble polymer such as HPMC E5 or with enteric or controlled release coatings.
Method B: Three-layered Tablet.

A first immediate release composition is prepared as just described except that the indomethacin is complexed with the $SBE_7$-$\beta$-CD using well known conditions to form a drug/SAE-CD complex which is included in the immediate release composition in place of the corresponding physical mixture. The first immediate release composition is compressed to form a first immediate release layer. A controlled release composition is prepared as described in Method A and compressed onto one side of the first immediate release layer to form a controlled release layer. A second immediate release composition is prepared according to the method used to prepare the first immediate release composition. The second immediate release composition is then compressed onto the controlled release layer on a surface opposite the first immediate release layer. In this exemplary embodiment, the indomethacin is distributed between the three layers of the formulation as follows: 25% wt. of the drug is present in each of the first and second immediate release layers, and the remaining 50% wt. of the drug is present in the controlled release layer. The tablet can then be coated with a readily water soluble polymer such as HPMC E5 or with enteric or controlled release coatings.

EXAMPLE 9

Tablets Comprising a Controlled Release Core with a Compression Coating

Tablet cores containing a physical mix of indomethacin with the cyclodextrin in the presence of the HPMC K15M and other excipients, as described in the previous example, may be compressed into slow release matrix tablets. Using suitable tableting equipment as known in the art, an immediate release granulation containing the preformed complex is compressed onto the slow release cores. The rapid disintegration of the granulation in the compressed coating will release the preformed complex into the dissolution medium or into the GI fluids to allow rapid dissolution of the indomethacin. Slow erosion and hydration of the tablet core coated by the physical mix, will promote drug-cyclodextrin complex formation and control the release of the complex into the surrounding milieu.

EXAMPLE 10

Granulations prepared by melt techniques

Granulations containing a physical blend of drug, cyclodextrin, and hydrophilic polymers along with the other functional excipients may be prepared by melt granulation or hot melt extrusion. A physical blend is made from the following ingredients:

| Diltiazem | 10 mg |
|---|---|
| SBE$_7$-β-CD | 270 mg |
| Citric acid | 19 mg |
| PEG 6000 | 42 mg |
| HPMC K15M | 50 mg |
| Total | 400 mg |

This material is then passed through an extruder at 60° C. or melt granulated at the same temperature to form granules which are then sized through a #20 screen and blended with 75 mg MCC PH101, 10 mg magnesium stearate, and 15 mg talc to prepared tablets weighing 500 mg. These tablets containing drug in the form of a physical blend will hydrate in a dissolution medium or in the gastrointestinal tract to slowly release the diltiazem by diffusion and erosion mechanisms.

EXAMPLE 11

Osmotic Pumps with Diffusionally and Osmotically Controlled Delivery of Drug

For the preparation of cores, physical mixtures of TS with (SBE)$_{7m}$-β-CD, HP-β-CD or sugar (physical mixture of lactose and fructose, 1/1) each containing 10 mg TS were compressed at 1 ton/cm$^2$ for 60 sec using a Carver™ Laboratory Press with a 6.35 mm flat faced punch. The molar ratios of TS to (SBE)$_{7m}$-β-CD in the physical mixtures ranged from 1:1 to 1:1.43 and that in the physical mixture with HP-β-CD ranged from 1:1 to 1:1.79. The physical mixtures of TS with the β-CD derivatives or sugar were prepared using a mortar and a pestle. The compressed tablet core was placed in a tablet die as described above.

A semipermeable membrane was prepared by mixing 59.3% cellulose acetate, 29.6% sorbitol and 11.1 % of PEG or talc in dichloromethane/methanol/water (3/2/0.2 as weight ratio). The final concentration of solids in the solution was 3.34% w/w. The membranes were reproducibly prepared on the base of the osmotic pump device by film coating using an air brush at a spray rate of 1.7 g/min with coincident drying by blowing heated air from a dryer fixed 30 cm above the die. The membranes were then peeled from the base surface of the osmotic pump device and placed on the release side of the device. The membrane was held in place by a TEFLON™ seal and a stainless steel washer.

The dissolution and release rates of TS from core tablets (no membrane covering) or the osmotic pump devices (core tablets covered by a semipermeable membrane) were measured using a USP apparatus utilizing the paddle method. The medium was nine hundred milliliters of distilled water or various KCl solutions at 37° C. with the paddle stirring speeds ranging from 0 to 100 rpm. The device was placed in the vessel with the release side up. Bulk solution TS samples were assayed by the HPLC method described earlier for the phase-solubility studies. Measurement of osmotic pump agents released from the devices. The amount of each osmotic pump agent, (SBE)$_{7m}$-β-CD, HP-β-CD and sugar, released from the OPT was calculated by difference from the weight of the total ingredients released and the weight of the remaining released components at each sampling time in the study. The weight of the remaining components at each sampling time is the summation of testosterone quantitated by HPLC and sorbitol and PEG content was determined gravimetrically from osmotic pumps which did not contain osmotic agents. The weight of the released osmotic agent was measured as a residual weight after evaporating and vacuum drying a 200 ml solution sample for 12 hr at 60° C. Because of their high water solubility, it was assumed that sorbitol and PEG were immediately and completely released from the membrane of the osmotic pump after it being dipped into the test solution.

The above is a detailed description of particular embodiments of the invention. Those of ordinary skill in the art should, in light of the present disclosure, appreciate that obvious modifications of the embodiments disclosed herein can be made without departing from the spirit and scope of the invention. All of the embodiments disclosed and claimed herein can be made and executed without undue experimentation in light of the present disclosure. The full scope of the invention is set out in the claims that follow and their equivalents. Accordingly, the claims and specification should not be construed to unduly narrow the full scope of protection to which the present invention is entitled.

What is claimed is:

1. A controlled release solid pharmaceutical formulation consisting of a core comprising a first composition comprising a physical mixture of:
    a therapeutic agent;
    at least one sulfoalkyl ether cyclodextrin; and
    at least one release rate modifier;
    wherein,
        a major portion of the therapeutic agent is not complexed with the sulfoalkyl ether cyclodextrin; and
        the therapeutic agent of the first composition is released from the core at a controlled rate in the absence of a release rate modifying coat surrounding the core.

2. The controlled release solid pharmaceutical formulation of claim 1 wherein decreasing the viscosity of said release rate modifier decreases a rate of release of said therapeutic agent and increases a rate of release of said sulfoalkyl ether cyclodextrin from said formulation.

3. The controlled release solid pharmaceutical formulation of claim 1 wherein said release rate modifier is present in an amount sufficient to render a first rate of release of said therapeutic agent and a second rate of release of said sulfoalkyl ether cyclodextrin independent of a viscosity of said release rate modifier.

4. The controlled release solid pharmaceutical formulation of claim 3 wherein said release rate modifier is present in excess of said therapeutic agent and said sulfoalkyl ether cyclodextrin on a weight basis.

5. The controlled release solid pharmaceutical formulation of claim 3 wherein a ratio of said release rate modifier to said sulfoalkyl ether cyclodextrin is about 1:1 to about 20:1 on a weight basis.

6. The controlled release solid pharmaceutical formulation of claim 1 wherein said release rate modifier is present in an amount sufficient to render a first rate of release of said therapeutic agent and a second rate of release of said sulfoalkyl ether cyclodextrin is dependent upon a viscosity of said release rate modifier.

7. The controlled release solid pharmaceutical formulation of claim 6 wherein said sulfoalkyl ether cyclodextrin is present in excess of said therapeutic agent and said release rate modifier on a weight basis.

8. The controlled release solid pharmaceutical formulation of claim 6 wherein a ratio of said release rate modifier to said sulfoalkyl ether cyclodextrin is about 1:1 to about 1:20 on a weight basis.

9. The controlled release solid pharmaceutical formulation of claim 6 wherein said release rate modifier is swellable in an environment of use.

10. The controlled release solid pharmaceutical formulation of claim 1 wherein release of said sulfoalkyl ether cyclodextrin from said formulation is independent of a ratio of an amount of said therapeutic agent to an amount of said sulfoalkyl ether cyclodextrin.

11. The controlled release solid pharmaceutical formulation of claim 1 wherein release of said therapeutic agent from said formulation approximates release of said therapeutic agent from a second formulation similar to said pharmaceutical formulation except that in said second formulation all of said therapeutic agent is complexed with said sulfoalkyl ether cyclodextrin.

12. The controlled release solid pharmaceutical formulation of claim 1 wherein increasing an amount of said release rate modifier with respect to an amount of said therapeutic agent will effect a decrease in a rate of release of said therapeutic agent and a decrease in a rate of release of said sulfoalkyl ether cyclodextrin.

13. The controlled release solid pharmaceutical formulation of claim 1 wherein increasing an amount of said therapeutic agent with respect to an amount of said sulfoalkyl ether cyclodextrin will effect a decrease in a rate of release of said therapeutic agent.

14. The controlled release solid pharmaceutical formulation of claim 1, wherein said core further comprises a different second composition comprising a preformed therapeutic agent/sulfoalkyl ether cyclodextrin inclusion complex, wherein said therapeutic agent of said second composition is released from the core at a rapid rate.

15. The controlled release solid pharmaceutical formulation of claim 1, wherein a molar ratio of said therapeutic agent to said sulfoalkyl ether cyclodextrin is in the range of about 2:1 to about 1:10.

16. The controlled release solid pharmaceutical formulation of claim 1 wherein said sulfoalkyl ether is a compound or mixture of compounds of the formula (I):

Formula I

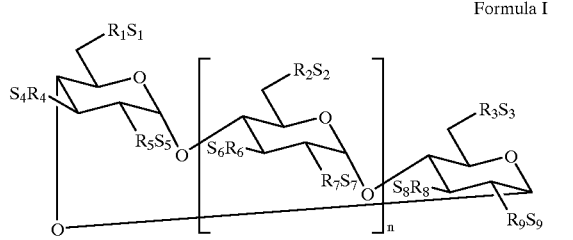

wherein: n is 4, 5 or 6;

$R_1$, $R_2$, $R_3$, $R_4$, $R_5$, $R_6$, $R_7$, $R_8$ and $R_9$ are each, independently, —O— or —O—(C2–C6 alkylene)—$SO_3$—, wherein at least one of $R_1$ and $R_2$ is independently —O—(C2–C6 alkylene)—$SO_3$—; and $S_1$, $S_2$, $S_3$, $S_4$, $S_5$, $S_6$, $S_7$, $S_8$ and $S_9$ are each, independently, a pharmaceutically acceptable cation.

17. A controlled release solid pharmaceutical formulation comprising:

a core comprising a first composition comprising a physical mixture of a therapeutic agent and at least one sulfoalkyl ether cyclodextrin, wherein a major portion of the therapeutic agent is not complexed with the sulfoalkyl ether cyclodextrin; and a coating surrounding said core and consisting of a film forming agent;

wherein, said therapeutic agent of the first composition is released from the core at a controlled rate in the absence of a pore forming agent in the coating.

18. The controlled release solid pharmaceutical formulation of claim 17 wherein said coating is a semipermeable membrane having a passageway therethrough.

19. The controlled release solid pharmaceutical formulation of claim 17 wherein said core further comprises a release rate modifier.

20. The controlled release solid pharmaceutical formulation of claim 17 wherein release of said therapeutic agent from said formulation approximates release of said therapeutic agent from a second formulation substantially similar to said pharmaceutical formulation except that in said second formulation of said therapeutic agent is complexed with said sulfoalkyl ether cyclodextrin.

21. The controlled release solid pharmaceutical formulation of claim 17, wherein said core further comprises a different second composition comprising a preformed therapeutic agent/sulfoalkyl ether cyclodextrin inclusion complex, wherein said therapeutic agent of said second composition is released from the core at a rapid rate.

22. The controlled release solid pharmaceutical formulation of claim 17 wherein said sulfoalkyl ether is a compound or mixture of compounds of the formula (I):

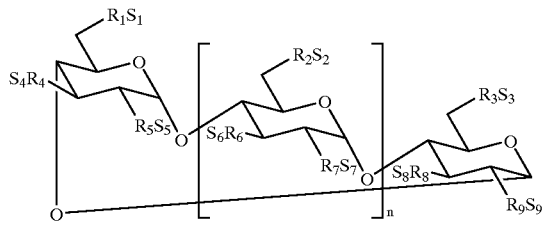

wherein: n is 4, 5 or 6;

$R_1$, $R_2$, $R_3$, $R_4$, $R_5$, $R_6$, $R_7$, $R_8$ and $R_9$ are each, independently, —O— or —O—(C2–C6 alkylene)—$SO_3$—, wherein at least one of $R_1$ and $R_2$ is independently —O—(C2–C6 alkylene)—$SO_3$—; and $S_1$, $S_2$, $S_3$, $S_4$, $S_5$, $S_6$, $S_7$, $S_8$ and $S_9$ are each, independently, a pharmaceutically acceptable cation.

23. A multi-layered controlled release solid pharmaceutical formulation comprising:

at least one first layer comprising a physical mixture of a therapeutic agent and a sulfoalkyl ether cyclodextrin; and at least one second layer comprising a release rate modifier;

wherein,
said first and second layers are juxtaposed;
said therapeutic agent is released from said core at a controlled rate; and
a major portion of said therapeutic agent is not complexed with said sulfoalkyl ether cyclodextrin.

24. The multi-layered controlled release solid pharmaceutical formulation of claim 23 wherein said sulfoalkyl ether is a compound or mixture of compounds of the formula (I):

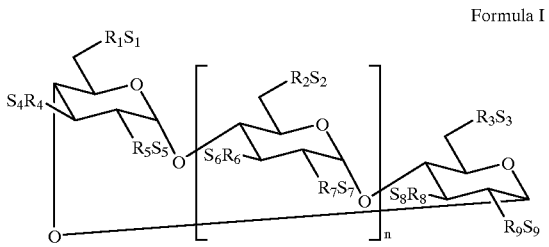

Formula I wherein: n is 4, 5 or 6;

$R_1$, $R_2$, $R_3$, $R_4$, $R_5$, $R_6$, $R_7$, $R_8$ and $R_9$ are each, independently, —O— or —O—(C2–C6 alkylene)
—SO$_3$—, wherein at least one of $R_1$ and $R_2$ is independently —O—(C2–C6 alkylene)—SO$_3$—; and $S_1$, $S_2$, $S_3$, $S_4$, $S_5$, $S_6$, $S_7$, $S_8$ and $S_9$ are each, independently, a pharmaceutically acceptable cation.

25. The multi-layered controlled release solid pharmaceutical formulation of claim 23 wherein said pharmaceutical composition is surrounded by a coating comprising a film forming agent.

26. The multi-layered controlled release solid pharmaceutical formulation of claim 23 wherein said first layer surrounds said second layer.

27. The multi-layered controlled release solid pharmaceutical formulation of claim 23 wherein said first layer independently further comprises a release rate modifier.

28. The multi-layered controlled release solid pharmaceutical formulation of claim 23 wherein said formulation is a tablet, minitablet, granule, pellet or micropellet.

29. A multi-layered combined rapid and controlled release solid pharmaceutical formulation comprising:

at least one controlled release first layer comprising a physical mixture of a first therapeutic agent, a release rate modifier and a sulfoalkyl ether cyclodextrin for releasing said first therapeutic agent at a controlled rate into a first environment of use; and at least one rapid release second layer comprising a preformed complex of a second therapeutic agent and a sulfoalkyl ether cyclodextrin for releasing said second therapeutic agent rapidly into a second environment of use;

wherein,
said first and second layers are juxtaposed;
a major portion of said first therapeutic agent is not complexed with said sulfoalkyl ether cyclodextrin.

30. The multi-layered combined rapid and controlled release solid pharmaceutical formulation of claim 29 wherein said sulfoalkyl ether is a compound or mixture of compounds of the formula (I).

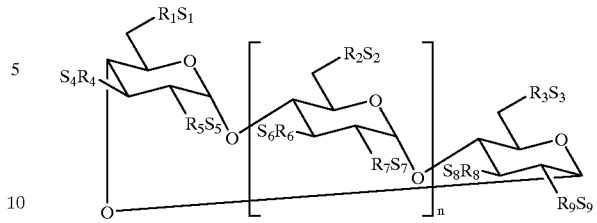

Formula I wherein: n is 4, 5 or 6;

$R_1$, $R_2$, $R_3$, $R_4$, $R_5$, $R_6$, $R_7$, $R_8$ and $R_9$ are each, independently —O— or —O—(C2–C6 alkylene)
—SO$_3$—, wherein at least one of $R_1$ and $R_2$ is independently —O—(C2–C6 alkylene)—SO$_3$—; and $S_1$, $S_2$, $S_3$, $S_4$, $S_5$, $S_6$, $S_7$, $S_8$ and $S_9$ are each, independently, a pharmaceutically acceptable cation.

31. The multi-layered combined rapid and controlled release solid pharmaceutical formulation of claim 29 wherein said pharmaceutical composition is surrounded by a coating comprising a film forming agent.

32. The multi-layered combined rapid and controlled release solid pharmaceutical formulation of claim 29 wherein said at least one rapid release second layer surrounds said at least one controlled release first layer.

33. The multi-layered combined rapid and controlled release solid pharmaceutical formulation of claim 29 wherein said formulation is a tablet, minitablet, granule, pellet or micropellet.

34. A multi-layered combined rapid and controlled release solid pharmaceutical formulation comprising:

at least one controlled release first layer comprising a physical mixture of a first therapeutic agent, a release rate modifier and a sulfoalkyl ether cyclodextrin for releasing said first therapeutic agent at a controlled rate into a first environment of use; and at least one rapid release second layer comprising a physical mixture of a second therapeutic agent and a sulfoalkyl ether cyclodextrin for releasing said second therapeutic agent rapidly into a second environment of use;

wherein,
said first and second layers are juxtaposed; and
major portions of each of said first and second therapeutic agents are not complexed with said sulfoalkyl ether cyclodextrin.

35. The multi-layered combined rapid and controlled release solid pharmaceutical formulation of claim 34 wherein said sulfoalkyl ether is a compound or mixture of compounds of the formula (I).

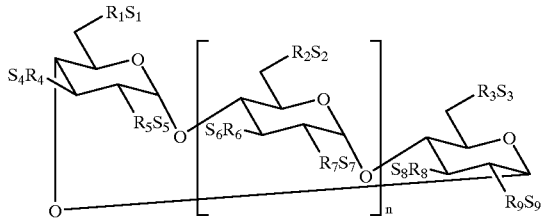

Formula I

—SO$_3$—, wherein at least one of R$_1$ and R$_2$ is independently —O—(C2–C6 alkylene)—SO$_3$—; and S$_1$, S$_2$, S$_3$, S$_4$, S$_5$, S$_6$, S$_7$, S$_8$ and S$_9$ are each, independently, a pharmaceutically acceptable cation.

36. The multi-layered combined rapid and controlled release solid pharmaceutical formulation of claim 34 wherein said pharmaceutical composition is surrounded by a coating comprising a film forming agent.

37. The multi-layered combined rapid and controlled release solid pharmaceutical formulation of claim 34 wherein said at least one rapid release second layer surrounds said at least one controlled release first layer.

38. The multi-layered combined rapid and controlled release solid pharmaceutical formulation of claim 34 wherein said formulation is a tablet, minitablet, granule, pellet or micropellet.

39. The multi-layered combined rapid and controlled release solid pharmaceutical formulation of claim 34 comprising:
one controlled release first layer comprising a physical mixture of a first therapeutic agent, a release rate modifier and a sulfoalkyl ether cyclodextrin for releasing said first therapeutic agent at a controlled rate into a first environment of use; and
two rapid release second layers each comprising a physical mixture of a second therapeutic agent and a sulfoalkyl ether cyclodextrin for releasing said second therapeutic agent rapidly into a second environment of use;
wherein,
said controlled release first layer is disposed between said two rapid release second layers.

40. An osmotic solid pharmaceutical formulation for the controlled diffusional and osmotic delivery of a therapeutic agent to an environment of use comprising:
a core comprising a physical mixture of a sulfoalkyl ether cyclodextrin, a therapeutic agent and a pharmaceutically acceptable carrier; and
a membrane surrounding said core and comprising a film forming agent and a pore forming agent, said membrane having a passageway therethrough for communicating said core to an environment of use;
wherein,
a first portion of said therapeuic agent diffuses through said membrane and a second portion of said therapeutic agent passes through said passageway; and
a major portion of said therapeutic agent is not complexed with said sulfoalkyl ether cyclodextrin.

41. The osmotic solid pharmaceutical formulation of claim 40, wherein said membrane is at least one of semipermeable and microporous.

42. The osmotic solid pharmaceutical formulation of claim 40, wherein said membrane has a thickness and composition such that said therapeutic agent is primarily delivered through said passageway.

43. The osmotic solid pharmaceutical formulation a of claim 40, wherein said membrane has a thickness and composition such that said therapeutic agent is primarily delivered through said membrane by diffusion.

44. The osmotic solid pharmaceutical formulation of claim 40, wherein said core further comprises an osmagent.

45. The osmotic solid pharmaceutical formulation of claim 40, wherein said core further comprises a separate composition comprising an inclusion complex of said therapeutic agent and said sulfoalkyl ether cyclodextrin.

46. The osmotic solid pharmaceutical formulation of claim 40, wherein about 5%–75% of said therapeutic agent is released within about 6 hours.

47. The osmotic solid pharmaceutical formulation of claim 40, wherein more than 75% of said therapeutic agent is not complexed with said sulfoalkyl ether cyclodextrin.

48. The controlled release solid pharmaceutical formulation of claim 1, wherein about 5%–75% of said therapeutic agent is released within about 6 hours.

49. The controlled release solid pharmaceutical formulation of claim 1, wherein more than 75% of said therapeutic agent is not complexed with said sulfoalkyl ether cyclodextrin.

50. The controlled release solid pharmaceutical formulation of claim 17, wherein about 5%–75% of said therapeutic agent is released within about 6 hours.

51. The controlled release solid pharmaceutical formulation of claim 17, wherein more than 75% of said therapeutic agent is not complexed with said sulfoalkyl ether cyclodextrin.

52. The multi-layered controlled release solid pharmaceutical formulation of claim 23, wherein about 5%–75% of said therapeutic agent is released within about 6 hours.

53. The multi-layered controlled release solid pharmaceutical formulation of claim 23, wherein more than 75% of said therapeutic agent is not complexed with said sulfoalkyl ether cyclodextrin.

54. The multi-layered combined rapid and controlled release solid pharmaceutical formulation of claim 29, wherein about 5%–75% of said therapeutic agent is released within about 6 hours.

55. The multi-layered combined rapid and controlled release solid pharmaceutical formulation of claim 29, wherein more than 75% of said therapeutic agent is not complexed with said sulfoalkyl ether cyclodextrin.

56. The multi-layered combined rapid and controlled release solid pharmaceutical formulation of claim 34, wherein about 5%–75% of said therapeutic agent is released within about 6 hours.

57. The multi-layered combined rapid and controlled release solid pharmaceutical formulation of claim 34, wherein more than 75% of said therapeutic agent is not complexed with said sulfoalkyl ether cyclodextrin.

58. A combination rapid and controlled release solid pharmaceutical formulation comprising a physical mixture of:
a first group of particles comprising a physical mixture of a first therapeutic agent, a release rate modifier and a sulfoalkyl ether cyclodextrin for releasing said first therapeutic agent at a controlled rate into a first environment of use; and
a second group of particles comprising an inclusion complex of a second therapeutic agent and a sulfoalkyl ether cyclodextrin for releasing said second therapeutic agent rapidly into a second environment of use.

59. The combination rapid and controlled release solid pharmaceutical formulation of claim 58, wherein said sulfoalkyl ether is a compound or mixture of compounds of the formula (I):

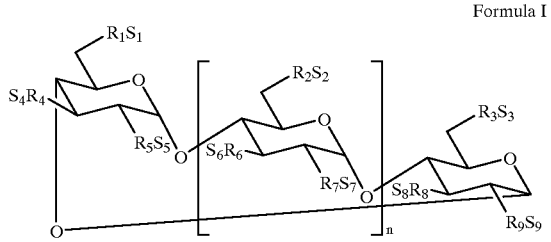

Formula I wherein: n is 4, 5 or 6;

$R_1$, $R_2$, $R_3$, $R_4$, $R_5$, $R_6$, $R_7$, $R_8$ and $R_9$ are each, independently, —O— or —O—(C2–C6 alkylene)—$SO_3$—, wherein at least one of $R_1$ and $R_2$ is independently —O—(C2–C6 alkylene)—$SO_3$—; and $S_1$, $S_2$, $S_3$, $S_4$, $S_5$, $S_6$, $S_7$, $S_8$ and $S_9$ are each, independently, a pharmaceutically acceptable cation.

60. The combination rapid and controlled release solid pharmaceutical formulation of claim 58, wherein said formulation is a tablet, capsule, microcapsule, or minitablet.

61. The combination rapid and controlled release solid pharmaceutical formulation of claim 58, wherein in said first group of particles said release rate modifier is present in excess of said therapeutic agent and said sulfoalkyl ether cyclodextrin on a weight basis.

62. The combination rapid and controlled release solid pharmaceutical formulation of claim 58, wherein in said first group of particles said release rate modifier is present in an amount sufficient to render a first rate of release of said therapeutic agent and a second rate of release of said sulfoalkyl ether cyclodextrin is independent of a viscosity of said release rate modifier.

63. The combination rapid and controlled release solid pharmaceutical formulation of claim 58, wherein in said first group of particles decreasing a viscosity of said release rate modifier decreases a rate of release of said therapeutic agent and increases a rate of release of said sulfoalkyl ether cyclodextrin from said formulation.

64. The combination rapid and controlled release solid pharmaceutical formulation of claim 58, wherein in said first group of particles said release rate modifier is present in an amount sufficient to render a first rate of release of said therapeutic agent and a second rate of release of said sulfoalkyl ether cyclodextrin is dependent upon a viscosity of said release rate modifier.

65. The combination rapid and controlled release solid pharmaceutical formulation of claim 64, wherein in said first group of particles said sulfoalkyl ether cyclodextrin is present in excess of said therapeutic agent and said release rate modifier on a weight basis.

66. The combination rapid and controlled release solid pharmaceutical formulation of claim 58, wherein in said first group of particles release of said sulfoalkyl ether cyclodextrin from said formulation is independent of a ratio of an amount of said therapeutic agent to an amount of said sulfoalkyl ether cyclodextrin.

67. The combination rapid and controlled release solid pharmaceutical formulation of claim 58, wherein in said first group of particles release of said therapeutic agent from said formulation approximates release of said therapeutic agent from a second formulation similar to said pharmaceutical formulation except that in said second formulation of said therapeutic agent is complexed with said sulfoalkyl ether cyclodextrin.

68. The combination rapid and controlled release solid pharmaceutical formulation of claim 58, wherein in said first group of particles increasing an amount of said release rate modifier with respect to an amount of said therapeutic agent will effect a decrease in a rate of release of said therapeutic agent and a decrease in a rate of release of said sulfoalkyl ether cyclodextrin.

69. The combination rapid and controlled release solid pharmaceutical formulation of claim 58, wherein in said first group of particles increasing an amount of said therapeutic agent with respect to an amount of said sulfoalkyl ether cyclodextrin will effect a decrease in a rate of release of said therapeutic agent.

70. The combination rapid and controlled release solid pharmaceutical formulation of claim 58, wherein said physical mixture in said first group of particles is present in excess of said inclusion complex in said second group of particles on a weight basis.

71. The combination rapid and controlled release solid pharmaceutical formulation of claim 58, wherein said inclusion complex in said second group of particles is present in excess of said physical mixture in said first group of particles on a weight basis.

72. The combination rapid and controlled release solid pharmaceutical formulation of claim 58, wherein said first and second environments of use are about the same.

73. The combination rapid and controlled release solid pharmaceutical formulation of claim 58, wherein said first and second therapeutic agents are the same.

74. The combination rapid and controlled release solid pharmaceutical formulation of claim 58, wherein said first and second therapeutic agents are different.

75. The combination rapid and controlled release solid pharmaceutical formulation of claim 58, wherein said first and second environments of use are different.

76. The combination rapid and controlled release solid pharmaceutical formulation of claim 58, wherein particles in one or more of said first and second groups of particles are coated with a membrane comprising a film-forming agent.

77. The combination rapid and controlled release solid pharmaceutical formulation of claim 76, wherein said membrane further comprises a pore forming agent.

78. The controlled release solid pharmaceutical formulation of claim 21, wherein said physical mixture is present in excess of said inclusion complex on a weight basis.

79. The controlled release solid pharmaceutical formulation of claim 21, wherein said inclusion complex is present in excess of said physical mixture on a weight basis.

80. The controlled release solid pharmaceutical formulation of claim 21, wherein said therapeutic agent in said inclusion complex is the same as said therapeutic agent in said physical mixture.

81. The controlled release solid pharmaceutical formulation of claim 21, wherein said therapeutic agent in said inclusion complex is different than said therapeutic agent in said physical mixture.

82. The multi-layered combined rapid and controlled release solid pharmaceutical formulation of claim 29, wherein said physical mixture in said first layer is present in excess of said inclusion complex in said second layer on a weight basis.

83. The multi-layered combined rapid and controlled release solid pharmaceutical formulation of claim 29, wherein said inclusion complex in said second layer is present in excess of said physical mixture in said first layer on a weight basis.

84. The multi-layered combined rapid and controlled release solid pharmaceutical formulation of claim 29, wherein said first and second environments of use are the same.

85. The multi-layered combined rapid and controlled release solid pharmaceutical formulation of claim 29, wherein said first and second environments of use are different.

86. The multi-layered combined rapid and controlled release solid pharmaceutical formulation of claim 29, wherein said first and second therapeutic agents are the same.

87. The multi-layered combined rapid and controlled release solid pharmaceutical formulation of claim 29, wherein said first and second therapeutic agents are different.

88. The multi-layered combined rapid and controlled release solid pharmaceutical formulation of claim 34, wherein said physical mixture in said first layer is present in excess of said physical mixture in said second layer on a weight basis.

89. The multi-layered combined rapid and controlled release solid pharmaceutical formulation of claim 34, wherein said physical mixture in said second layer is present in excess of said physical mixture in said first layer on a weight basis.

90. The multi-layered combined rapid and controlled release solid pharmaceutical formulation of claim 34, wherein said first and second environments of use are the same.

91. The multi-layered combined rapid and controlled release solid pharmaceutical formulation of claim 34, wherein said first and second environments of use are different.

92. The multi-layered combined rapid and controlled release solid pharmaceutical formulation of claim 34, wherein said first and second therapeutic agents are substantially the same.

93. The multi-layered combined rapid and controlled release solid pharmaceutical formulation of claim 34, wherein said first and second therapeutic agents are different.

94. The controlled release solid pharmaceutical formulation of claim 1 wherein release of said sulfoalkyl ether cyclodextrin from said formulation is dependent on a ratio of an amount of said therapeutic agent to an amount of said sulfoalkyl ether cyclodextrin.

95. The combination rapid and controlled release solid pharmaceutical formulation of claim 58, wherein in said first group of particles release of said sulfoalkyl ether cyclodextrin from said formulation is dependent on a ratio of an amount of said therapeutic agent to an amount of said sulfoalkyl ether cyclodextrin.

* * * * *